US011915795B2

(12) United States Patent
Fraley et al.

(10) Patent No.: US 11,915,795 B2
(45) Date of Patent: Feb. 27, 2024

(54) METHOD AND DEVICE FOR DIGITAL HIGH RESOLUTION MELT

(71) Applicant: The Regents of the University of California, La Jolla, CA (US)

(72) Inventors: Stephanie I. Fraley, San Diego, CA (US); Sinead Charpentier, San Juan Capistrano, CA (US); Daniel Ortiz Velez, San Diego, CA (US); Mridu Sinha, Milpitas, CA (US); Benjamin Albert Yang, Ann Arbor, MI (US)

(73) Assignee: The Regents of the University of California, Oakland, CA (US)

( * ) Notice: Subject to any disclaimer, the term of this patent is extended or adjusted under 35 U.S.C. 154(b) by 226 days.

(21) Appl. No.: 16/472,734

(22) PCT Filed: Dec. 22, 2017

(86) PCT No.: PCT/US2017/068313
§ 371 (c)(1),
(2) Date: Jun. 21, 2019

(87) PCT Pub. No.: WO2018/119443
PCT Pub. Date: Jun. 28, 2018

(65) Prior Publication Data
US 2021/0241857 A1   Aug. 5, 2021

Related U.S. Application Data

(60) Provisional application No. 62/438,660, filed on Dec. 23, 2016.

(51) Int. Cl.
*G16B 40/10* (2019.01)
*C12Q 1/686* (2018.01)
*G16B 30/00* (2019.01)
*G16B 25/00* (2019.01)
*G16B 25/20* (2019.01)

(52) U.S. Cl.
CPC ............ *G16B 40/10* (2019.02); *C12Q 1/686* (2013.01); *G16B 25/00* (2019.02); *G16B 25/20* (2019.02); *G16B 30/00* (2019.02)

(58) Field of Classification Search
None
See application file for complete search history.

(56) References Cited

U.S. PATENT DOCUMENTS

| | | | | |
|---|---|---|---|---|
| 6,941,287 B1 * | 9/2005 | Vaidyanathan | ........ | G06N 3/126 |
| | | | | 706/14 |
| 9,393,566 B2 | 7/2016 | Hasson et al. | | |
| 2002/0150900 A1 * | 10/2002 | Marshall | .............. | C12Q 1/6827 |
| | | | | 435/6.12 |
| 2008/0003593 A1 * | 1/2008 | Hasson | .................. | G06T 7/0012 |
| | | | | 435/6.16 |
| 2010/0173394 A1 * | 7/2010 | Colston, Jr. | ............. | B01L 7/525 |
| | | | | 422/68.1 |
| 2011/0105345 A1 | 5/2011 | Cheng et al. | | |
| 2014/0038189 A1 * | 2/2014 | Igata | .................... | C12Q 1/6844 |
| | | | | 435/6.12 |
| 2014/0038195 A1 * | 2/2014 | Malik | .................. | C12Q 1/6851 |
| | | | | 435/6.12 |
| 2014/0039802 A1 * | 2/2014 | Kanderian | ............. | G16B 20/20 |
| | | | | 702/19 |
| 2014/0278126 A1 | 9/2014 | Adelman et al. | | |
| 2014/0302503 A1 * | 10/2014 | Lowe | .................. | C12Q 1/6851 |
| | | | | 435/6.12 |
| 2015/0024953 A1 | 1/2015 | Yang et al. | | |
| 2015/0086581 A1 * | 3/2015 | Li | .......................... | C12Q 1/689 |
| | | | | 424/234.1 |
| 2015/0307919 A1 * | 10/2015 | Ness | .................. | G01N 21/6486 |
| | | | | 506/9 |
| 2015/0368646 A1 * | 12/2015 | Hingorani | .............. | A61K 45/06 |
| | | | | 536/24.5 |
| 2016/0310949 A1 | 10/2016 | Kwang | | |
| 2017/0088879 A1 * | 3/2017 | Keys | .................... | C12Q 1/6851 |
| 2017/0321257 A1 | 11/2017 | Andini et al. | | |
| 2017/0335378 A1 * | 11/2017 | Mancebo | ............. | C12Q 1/6827 |

FOREIGN PATENT DOCUMENTS

| | | | | |
|---|---|---|---|---|
| WO | WO2000066777 A2 * | 11/2000 | ............... | C12Q 1/68 |
| WO | WO 2015/023616 | 2/2015 | | |
| WO | WO 2015/104797 | 7/2015 | | |
| WO | WO 2017/025589 | 2/2017 | | |

OTHER PUBLICATIONS

Heyries et al. Megapixel digital PCR. Nature Methods 8(8):649-651. (Year: 2011).*
Athamanolap et al., "Droplet Array Platform for High Resolution Melt Analysis of DNA Methylation Density," Journal of laboratory automation, 2013, 19:304-312.
Athamanolap et al., "Trainable high resolution melt curve machine learning classifier for large-scale reliable genotyping of sequence variants," PLoS One, 2014, 9:e109094.
Blainey et al., "The future is now: single-cell genomics of bacteria and archaea," FEMS microbiology reviews, 2013, 37(3):407-427.
Candiloro et al., "A Rapid analysis of heterogeneously methylated DNA using digital methylation-sensitive high resolution melting: application to the CDKN2B (p15) gene," Epigenetics & chromatin, 2008, 1(1):7.

(Continued)

*Primary Examiner* — Samuel C Woolwine

(74) *Attorney, Agent, or Firm* — Fish & Richardson P.C.

(57) ABSTRACT

Methods are provided for nucleic acid analysis via a platform which incorporates a digital sample partitioning platform such as a microfluidic chip or digital droplet platform and instrumentation to accomplish universal amplification, High Resolution Melting (HRM), and machine learning within reactions simultaneously.

20 Claims, 29 Drawing Sheets

Specification includes a Sequence Listing.

(56) References Cited

OTHER PUBLICATIONS

Castresana et al., "Detection of methylation in promoter sequences by melting curve analysis-based semiquantitative real time PCR," Bmc, 2008, 8(1).
Chakravorty et al., "A detailed analysis of 16S ribosomal RNA gene segments for the diagnosis of pathogenic bacteria," Journal of Microbiologial Methods, 2007, 69:330-339.
Chakravorty et al., "Genotypic susceptibility testing of Mycobacterium tuberculosis isolates for amikacin and kanamycin resistance by use of a rapid sloppy molecular beacon-based assay identifies more cases of low-level drug resistance than phenotypic Lowenstein-Jensen testing," J Clin Aficrobiol, 2015, 53:43-51.
Dellinger et al., "Surviving Sepsis Campaign: international guidelines for management of severe sepsis and septic shock: 2008," Critical care medicine, 2008, 36(1):296-327.
Den Dunnen et al., "A High-Resolution Melting Analysis (HRMA)-More Than Just Sequence Variant Screening," Hum Mutat, 2009, 30:860-866.
Dietzman et al., "Neonatal *Escherichia coli* septicemia—bacterial counts in blood," The Journal of pediatrics, 1974, 85:128-130.
Drukker et al., "Model simulations of DNA denaturation dynamics," J Chem. Phys., 2011, 114:579.
Dwight et al., "uMELT: prediction of high-resolution melting curves and dynamic melting profiles of PCR products in a rich web application," Bioinformatics, 2011, 27(7):1019-1020.
El-Hajj et al., "Use of sloppy molecular beacon probes for identification of mycobacterial species," J Clin Microbiol, 2009, 47:1190-1198.
Erali et al., "SNP genotyping by unlabeled probe melting analysis," Methods in molecular biology, 2008, 429:199-206.
Fan et al., "Highly parallel genomic assays," Nat Rev Genet, 2006, 7:632-644.
Fraley et al., "Nested Machine Learning Facilitates Increased Sequence Content for Large-Scale Automated High Resolution Melt Genotyping," Sci Rep, 2016, 6(1):19218.
Fraley et al., "Universal digital high-resolution melt: a novel approach to broad-based profiling of heterogeneous biological samples," Nucleic Acids Research, 2013, 41:e175.
Frey et al., "Comparison of three next-generation sequencing platforms for metagenomic sequencing and identification of pathogens in blood, " BMC genomics, 2014, 15:96.
Gundry et al., "Base-pair neutral homozygotes can be discriminated by calibrated high-resolution melting of small amplicons, " Nucleic Acids Res., 2008, 36:3401-3408.
Gurtler et al., "A novel method for simultaneous Enterococcus species identification/typing and van genotyping by high resolution melt analysis," Journal of Mcrobiological Methods, 2012, 90:167-181.
Hardick et al., "Identification of Bacterial Pathogens in Ascitic Fluids from Patients with Suspected Spontaneous Bacterial Peritonitis by Use of BroadRange Pcr (16S Pcr) Coupled with High-Resolution Melt Analysis," Journal of Clinical Aficrobiology, 2012, 50:2428-2432.
Herrmann et al., "Amplicon DNA Melting Analysis for Mutation Scanning and Genotyping: Cross-Platform Comparison of Instruments and Dyes," Clin. Chem., 2006, 52(3)494-503.
Hjelmso et al., "High Resolution Melt analysis for rapid comparison of bacterial community composition," Applied and Environmental Microbiology, 2014, 80(12):3568-3575.
International Preliminary Report on Patentability in International Appln. No. PCT/US2017/068313, dated Jun. 25, 2019, 8 pages.
International Search Report and Written Opinion in International Appln. No. PCT/US2017/068313, dated Apr. 12, 2018, 8 pages.
James et al., "Use of a high resolution melting assay to analyze HIV diversity in HIV-infected Ugandan children." Pediatr. Infect. Dis. J., 2012, 31:e222-8.
Jeng et al., "Application of a 16S rRNAPCR-High-Resolution Melt Analysis Assay for Rapid Detection of Salmonella Bacteremia, " Journal of Clinical Microbiology, 2012, 50:1122-1124.

Kellogg et al., "Frequency of low level bacteremia in infants from birth to two months of age," Pediatr Infect Dis J, 1997, 16:381-385.
Li et al., "Genotyping Accuracy of High Resolution DNA Melting Instruments, " Clin. Chem., 2014, 60.
Lisboa et al., "We should be measuring genomic bacterial load and virulence factors," Critical care medicine, 2010, 38:S656-662.
Mallona et al., "pcrEfficiency: a Web tool for PCR amplification efficiency prediction," BMC Bioinformatics, 2011, 12:404.
Mao et al., "Characterization of EvaGreen and the implication of its physicochemical properties for qPCR applications," BAIC Biotechnol., 2007, 7:76.
Masek et al., "Sensitive detection and serovar differentiation of typhoidal and nontyphoidal *Salmonella enterica* species using 1 6S rRNA Gene PCR coupled with high-resolution melt analysis," J Mol Diagn, 2014, 16:261-266.
McGowan et al., "Outpatient pediatric blood cultures: time to positivity," Pediatrics, 2000, 106:251-255.
Mohamed Suhaimi al., "Non-invasive sensitive detection of KRAS and BRAF mutation in circulating tumor cells of colorectal cancer patients," Molecular oncology, 2015, 9:850-860.
Mohammadi et al., "Optimization of Real-Time PCR Assay for Rapid and Sensitive Detection of Eubacterial 16S Ribosomal DNA in Platelet Concentrates," J Clin Microbial, 2003, 41:4796-4 98.
Morrison et al., "Sensitive fluorescence-based thermodynamic and kinetic measurements of DNA hybridization in solution, " Biochemistry, 1993, 32:3095-104.
Nixon et al., "Comparative study of sensitivity, linearity, and resistance to inhibition of digital and nondigital polymerase chain reaction and loop mediated isothermal amplification assays for quantification of human cytomegalovirus," Anal Chem, 2014, 86:4387-4394.
Opota et al., "Blood culture-based diagnosis of bacteraemia: state of the art," Clinical Microbiology and Infectious Diseases, 2015, 21:313-322.
Ouldridge et al., "DNA hybridization kinetics: zippering, internal displacement and sequence dependence," Nucleic Acids Res., 2013, 41:8886-95.
Panjkovich et al., "Comparison of different melting temperature calculation methods for short DNA sequences," Bioinformatics, 2005, 21:711-722.
Pasic et al., "Genomic medicine: new frontiers and new challenges," Clin Chem, 2013, 59:158-167.
Patel, "MALDI-TOF MS for the diagnosis of infectious diseases," Clin Chem, 2015, 61:100-111.
Pfaffl et al., "Data analysis software," Realtime PCR Curr. Technol. Appl. Caister Acad. Press Norfolk, 2009, UK 65-83.
Pritchard et al., "MicroRNA profiling: approaches and considerations," Nat Rev Genet, 2012, 13:358-369.
Pritt et al., "Identification of a novel pathogenic *Borrelia* species causing Lyme borreliosis with unusually high spirochaetaemia: a descriptive study," Lancet Infect Dis, 2016, 16(5):556-564.
Reed et al., "Sensitivity and Specificity of Single-Nucleotide Polymorphism Scanning by High-Resolution Melting Analysis," Clinical Chemistry, 2004, 50:1748-1754.
Ririe et al., "Product Differentiation by Analysis of DNA Melting Curves during the Polymerase Chain Reaction," Anal. Biochem., 1997, 245:154-160.
Rothfuss et al., "Analysis of differential DNA damage in the mitochondrial genome employing a semi-long run real-time PCR approach," Nucleic Acids Res, 2010, 38:e24.
Rothman et al., "Detection of bacteremia in emergency department patients at risk for infective endocarditis using universal 16S rRNA primers in a decontaminated polymerase chain reaction assay, " J Infect Dis, 2002, 186(11):1677-1681.
Salter et al., "Reagent and laboratory contamination can critically impact sequence-based microbiome analyses, " BMC Biol, 2014, 12:87.
Schildkraut et al., "Dependence of the melting temperature of DNA on salt concentration," Biopolymers, 1965, 3:195-208.
Simonsen et al., "Early onset neonatal sepsis," Clinical microbiology reviews, 2014, 27(1):21-47.

(56) References Cited

OTHER PUBLICATIONS

Song et al., "Direct detection of bacterial genomic DNA at sub-femtomolar concentrations using single molecule arrays," Anal Chem, 2013, 85(3): 1932-1939.
Spangler et al., "Optimizing Taq polymerase concentration for improved signal-to-noise in the broad range detection of low abundance bacteria," PLoS One, 2009, 4:e7010.
Velez et al., "Massively parallel digital high resolution melt for rapid and absolutely quantitative sequence profiling," Nature Scientific Reports, 2017, 7:1-14.
Von Ahsen et al., "Oligonucleotide Melting Temperatures under PCR Conditions: Nearest-Neighbor Corrections for Mg2+, Deoxynucleotide Triphosphate, and Dimethyl Sulfoxide Concentrations with Comparison to Alternative Empirical Formulas," Clin. Chem., 2001, 47:1956-9161.
Wetmur, "DNA Probes: Applications of the Principles of Nucleic Acid Hybridization," Crit. Rev. Biochem. Mol. Biol., 1991, 26(3/4):227-259.
Yang et al., "Rapid identification of biothreat and other clinically relevantbacterial species by use of universal PCR coupled with high-resolution melting analysis," J Clin Microbiol, 2009, 47(7):2252-2255.
Zou et al., "High detection rates of colorectal neoplasia by stool DNA testing with a novel digital melt curve assay," Gastroenterology, 2009, 136:459-470.
Supplementary Partial European Search Report in EP Appln. No. 17882857, dated Aug. 18, 2020, 12 pages.
Extended European Search Report in EP Appln. No. 17882857, dated Nov. 19, 2020, 15 Pages.

\* cited by examiner

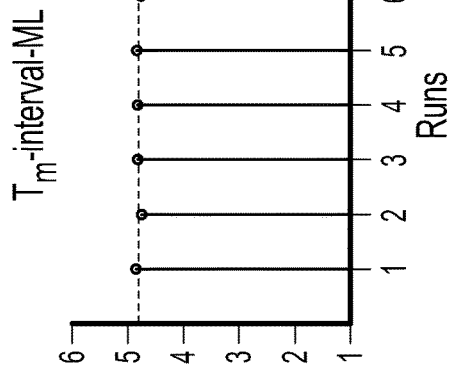
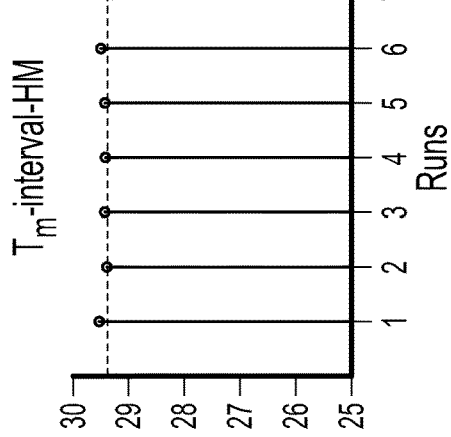
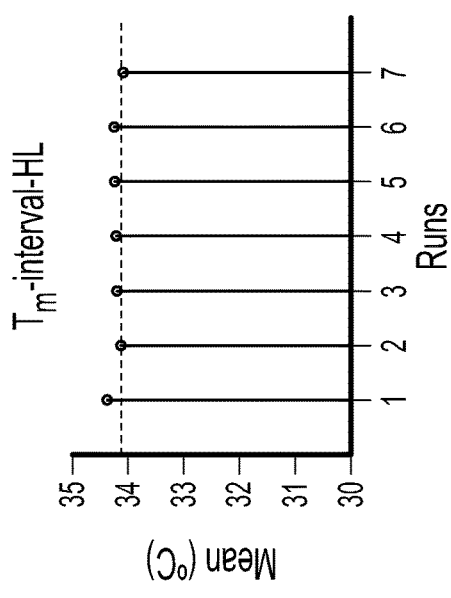
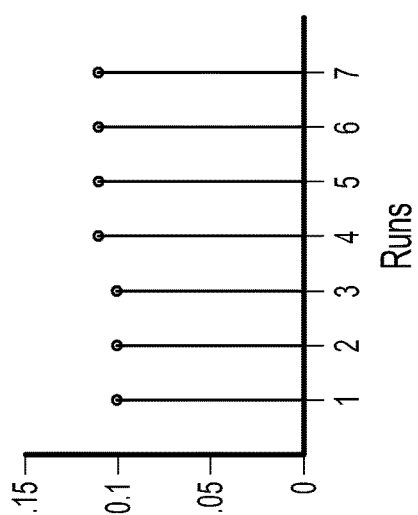
FIG. 13B
FIG. 13C

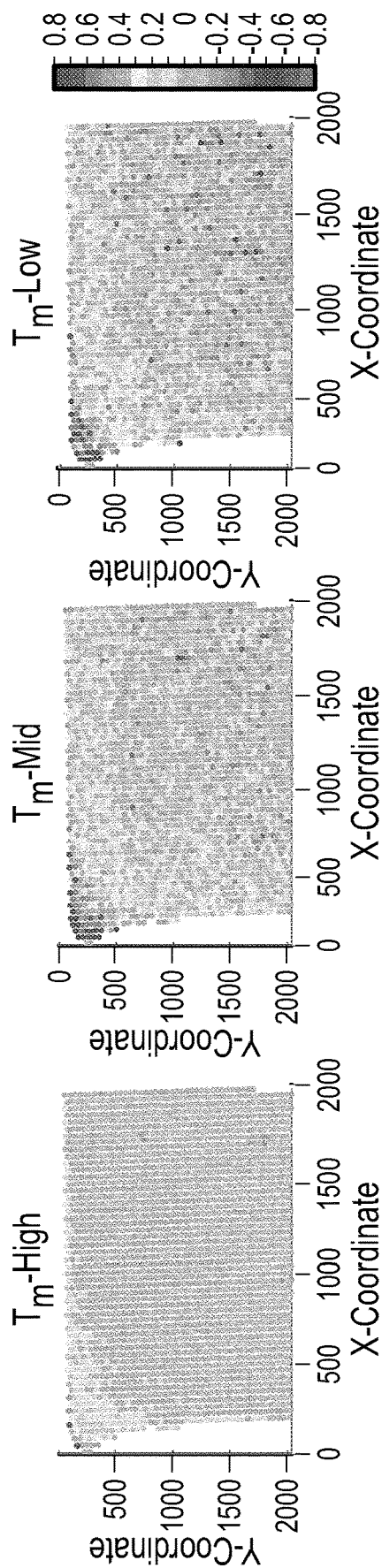
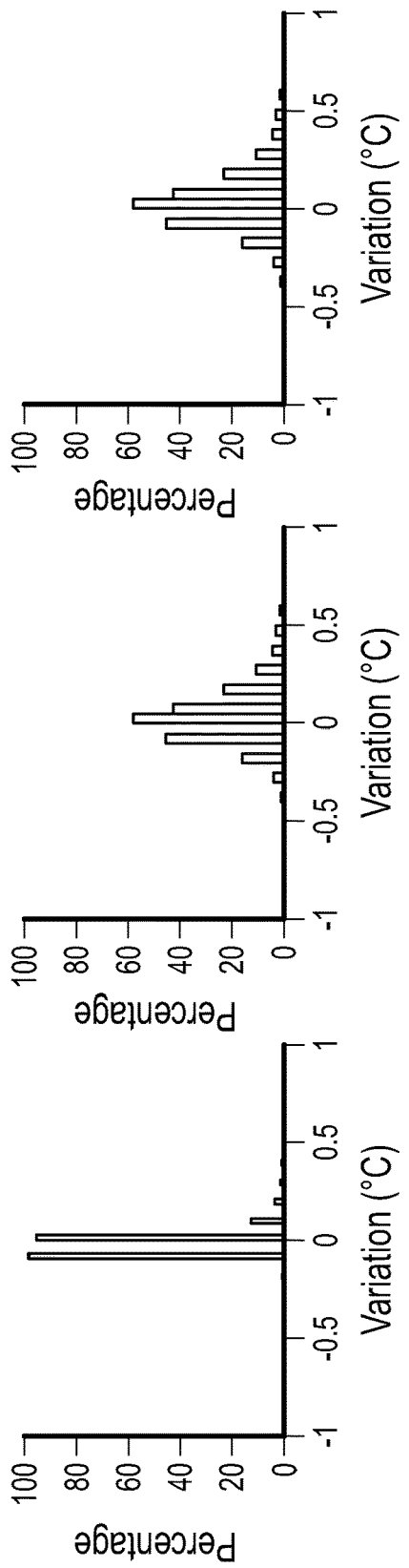
FIG. 14C
FIG. 14D

SEQUENCE LISTING

<160> NUMBER OF SEQ ID NOS: 5

<210> SEQ ID NO 1
<211> LENGTH: 50
<212> TYPE: DNA
<213> ORGANISM: Artificial Sequence
<220> FEATURE:
<223> OTHER INFORMATION: synthetic primer

<400> SEQUENCE: 1
ttaaattata aaatatttat aatattaatt atatatatat aaatataata          50

<210> SEQ ID NO 2
<211> LENGTH: 59
<212> TYPE: DNA
<213> ORGANISM: Artificial Sequence
<220> FEATURE:
<223> OTHER INFORMATION: synthetic primer

<400> SEQUENCE: 2
gcgcggccgg cacccgagac tctgagcggc tgctggaggt gcggaagcgg aggggcggg          59

<210> SEQ ID NO 3
<211> LENGTH: 50
<212> TYPE: DNA
<213> ORGANISM: Artificial Sequence
<220> FEATURE:
<223> OTHER INFORMATION: synthetic primer

<400> SEQUENCE: 3
ttaattataa aggtatttat aatattgaat tatacatatc taatataatc          50

<210> SEQ ID NO 4
<211> LENGTH: 19
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<223> OTHER INFORMATION: n = a, c, g, or t
<220> FEATURE:
<221> NAME/KEY: misc_feature
<222> LOCATION: (7)..(7)
<223> OTHER INFORMATION: n is a, c, g, or t

<400> SEQUENCE: 4
gyggcgnacg ggtgagtaa          19

<210> SEQ ID NO 5
<211> LENGTH: 19
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<223> OTHER INFORMATION: n = a, c, g, or t
<220> FEATURE:
<221> NAME/KEY: misc_feature
<222> LOCATION: (12)..(12)
<223> OTHER INFORMATION: n = a, c, g, or t

<400> SEQUENCE: 5
agctgacgac anccatgca          19

METHOD AND DEVICE FOR DIGITAL HIGH RESOLUTION MELT

CROSS-REFERENCE TO RELATED APPLICATIONS

This application is a 371 U.S. National Phase Application of PCT/US2017/068313, filed on Dec. 22, 2017, which claims priority to U.S. Application Ser. No. 62/438,660, filed on Dec. 23, 2016. The disclosure of the prior application is considered part of the disclosure of this application, and is incorporated in its entirety into this application.

TECHNICAL FIELD

The present invention relates to systems and related methods for the quantification and identification of nucleic acid target sequences in a heterogeneous sample after performing a universal nucleic acid amplification and, in particular, relates to the analysis of universal polymerase chain reactions using High Resolution Melting (HRM), and machine learning.

BACKGROUND

In clinical diagnostics and pathogen detection, profiling of complex samples for low-level genotypes represents a significant challenge. Advances in speed, sensitivity, and extent of multiplexing of molecular pathogen detection assays are needed to improve patient care.

The rapid and accurate profiling of pathogen genotypes in complex samples remains a challenge for existing molecular detection technologies. Currently, the identification of bacterial infections relies primarily on culture-based detection and phenotypic identification processes that require several days to weeks to complete. The practical application of molecular profiling technology is limited by several factors. To replace culture, molecular approaches must capture an equally wide array of pathogens while also providing specific and sensitive identification in a turnaround time fast enough to impact clinical decision making[1-3]. Studies also suggest that quantification of pathogen load may offer added benefits beyond what culture can offer[4]. However, the number of microbial genomes present in a clinical sample may be extremely low and/or the sample may be comprised of several different microbes. Current bacteria-targeted rapid screening technologies suffer from non-specific hybridization (e.g. microarrays, FISH), non-specific protein signals (e.g. protein mass spectrometry), or limited resolution of species (e.g. nucleotide mass spectrometry)[5-7]. Sequencing with conserved primers targeting the 16S or rpoB genes is the most useful molecular approach for detecting a wide range of bacteria with broad sensitivity, but is a time-consuming process that requires non-trivial technical expertise, computational resources, and analysis time. Moreover, recent studies report that several NGS platforms for microbial detection approach the analytical sensitivity of standard qPCR assays[3]. For applications where turnaround time is critical, high-level multiplexing of PCR-based identification strategies remain an active area of research.

Detection of microbial DNA in clinical samples like blood poses unique challenges. In this case, human DNA often vastly outnumbers that of the infecting microbe, necessitating targeted microbial DNA amplification. Since a vast array of pathogens can cause infection, a broad-based approach for amplifying all microbial DNA and a high level of specificity in post PCR sequence characterization techniques are required. Highly related organisms may have few DNA sequence differences, requiring single nucleotide specificity. Moreover, the number of microbial genomes present in the sample may be extremely low and/or the sample may be comprised of several different microbes, a polymicrobial infection, necessitating single cell level analysis. These requirements challenge the abilities of current molecular detection technologies, including next generation sequencing (NGS).

SUMMARY

In one aspect, the disclosure provides a method comprising combining a sample comprising a target nucleic acid sequence with universal amplification primers, one more DNA intercalating dye and an amplification mixture to form a reaction mixture; partitioning the reaction mixture into 10,000 or greater partitions (e.g., 10,000 or greater partitions, 20,000 or greater partitions, 50,000 or greater partitions, 100,000 or greater partitions, or 1,000,000 or greater partitions; amplifying the target nucleic acid sequence; detecting the amplified nucleic acid by simultaneously heating and imaging the partitioned reactions; and performing melt curve analysis using machine learning.

In one aspect, a method of profiling the sequence of a target nucleic acid in a sample is provided, the method including combining a sample including a target nucleic acid with one or more universal amplification primers, one or more DNA intercalating dyes, and reagents for amplifying a target nucleic acid to form a reaction mixture; partitioning the reaction mixture into 10,000 or greater partitions; amplifying the target nucleic acid sequence to produce an amplicon; performing melt analysis of the amplicon by simultaneously heating and imaging the partitions, whereby a melt curve for the amplicon is produced; and profiling the sequence of the target nucleic acid by comparing the melt curve for the amplicon to a plurality of melt curves from different nucleic acid sequences.

In some embodiments, the method can optionally include one or more of the following features. The reaction mixture can further include a reference dye. The method can further include detecting the reference dye and excluding noise values based on the detection of the reference dye. The reaction mixture can include a surfactant in an amount of from about 0.01% to about 0.8% v/v. The reagents for amplifying a target nucleic acid can include a high fidelity polymerase. Performing a melt curve analysis can include excluding melt curves below a threshold melt temperature. The reaction mixture can include at least two, at least three, at least five, at least ten unique universal amplification primers, or between two and six unique universal amplification primers. The one or more universal amplification primers can be selected from bacterial primers, fungal primers, viral primers, and combinations thereof. The target nucleic acid sequence can have an amplicon having a size greater than 1000 base pairs.

In some embodiments, the heating can be performed at a heating rate of 0.005° C./s to 0.5° C./s. Performing melt analysis of the amplicon by simultaneously heating and imaging the partitions can include performing imaging at an imaging rate that is synchronized with the heating rate. The imaging rate can be synchronized with the heating rate to maintain a resolution of from about 0.005° C. to about 0.1° C.

In some embodiments, the intercalating dye can be a fluorescent dye selected from the group consisting of EvaGreen SYBR Green I, LC Green, LC Green Plus, ResoLight, Chromofy and SYTO 9. In some embodiments, the reference dye is not an intercalating dye. The reference dye can be ROX.

In some embodiments, the amplicon originates from less than two target nucleic acid molecules in the sample. In some embodiments, the amplicon originates from a single target nucleic acid in the sample.

In some embodiments, the method can optionally include one or more of the following features. A plurality of melt curves can include at least one reference melt curve from a known nucleic acid sequence. Profiling the sequence of a target nucleic acid can be automated by use of a computer model or algorithm that classifies the target nucleic acid based on the comparison to the reference melt curve. Profiling the sequence of the target nucleic acid can include comparing the melt curve for the amplicon to a plurality of melt curves from different nucleic acid sequences. The computer model algorithm can be a machine learning algorithm for automated melt curve identification classification. In some embodiments, the algorithm can identify a target sequence versus junk, identify a novel pathogen, or classify a known sequence. The machine learning algorithm can use a probabilistic model for detection of nucleic acid signatures and for classification into a known pathogen or a novel pathogen unknown to the database. The classification model selected from a generative classifier and a discriminative classifier. The generative classifier can be a Naïve Bayes classifier. The discriminative classifier can be a Support Vector Machine (SVM) or Logistics Regression. In some embodiments, the detection of unknown pathogen can use Dynamic Time Warping. Profiling the sequence of the target nucleic acid can include comparing melt curve shape or melting temperature (Tm) of the amplicon. In some embodiments, profiling of nucleic acid can also be associated with a confidence score, such as, e.g., a confidence score generated using entropy measures.

In some embodiments, partitioning the reaction mixture can include fractionating the sample to contain zero to one nucleic acid molecules prior to the combining step. In some embodiments, the sample can include mammalian DNA.

In some embodiments, the method can include subjecting the sample to a first heating rate to obtain a first melt curve signature; subjecting the sample to a second heating rate to obtain a second melt curve signature; and performing a heating rate-dependent melt curve analysis using a computer model or algorithm that classifies the target nucleic acid based on the comparison to the reference melt curve. The computer model algorithm can optionally be a machine learning algorithm for automated melt curve classification. The machine learning algorithm can optionally use a probabilistic classification model selected from a generative classifier and a discriminative classifier.

In some embodiments, the method can further include identifying a pathogen or pathogen marker present in the sample, wherein the pathogen or pathogen marker has a known nucleic acid melt-curve signature. In some embodiments, the method can further include identifying a pathogen or pathogen marker present in the sample, wherein the pathogen or pathogen marker has an unknown nucleic acid melt-curve signature. In some embodiments, identifying a pathogen or pathogen marker present in the sample can have an error rate of less than 0.2%.

In some embodiments, the method can further include assigning confidence scores to sequence profiles obtained from profiling the sequence of the target nucleic acid. In some embodiments the machine learning algorithm can use a probabilistic model to assign confidence scores on classification. In some embodiments the algorithm can use an entropy measure, such as, e.g., Shannon entropy.

In some embodiments, partitioning the reaction mixture includes loading the reaction mixture onto a digital PCR chip. The method can further optionally include controlling a temperature difference between any two points on the chip during heating to 0.6° C. or less when performing melt analysis of the amplicon.

In some embodiments, partitioning the reaction mixture can include fractionating the reaction mixture into droplets using a ddPCR platform.

In some embodiments, the method further includes partitioning the reaction mixture into 20,000 or greater partitions, into 50,000 or greater partitions, into 100,000 or greater partitions, or into 1,000,000 or greater partitions.

In another aspect, a method of treating a patient suspected of having sepsis is provided, the method including identifying one or more pathogens having a high probability of mediating the patient's sepsis by performing the methods described herein; and administering to the patient one or more antimicrobials effective against the one or more identified pathogens.

In another aspect, a system is provided, including a digital sample partitioning platform; a thermoelectric heating device; one or more temperature feedback sensors; a temperature controller configured to control the thermoelectric heating device based on temperature feedback from at least one of the one or more temperature sensors; an imaging device; and a device including a processor configured to perform machine learning for automated melt curve classification.

In some embodiments, the system can optionally further include one or more of the following features. The digital sample partitioning platform can include a reaction mixture including one or more nucleic acids and a high fidelity polymerase. The reaction mixture can further include a reference dye. The reaction mixture can further include a surfactant in an amount of from about 0.01% to about 0.8% v/v. The reaction mixture can include at least two, at least three, at least five, or at least ten unique universal amplification primers. The reaction mixture can include between two and six unique universal amplification primers. The one or more universal amplification primers can be selected from bacterial primers, fungal primers, viral primers, and combinations thereof. The target nucleic acid sequence can have an amplicon having a size greater than 1000 base pairs. The temperature controller can be a proportional-integral-derivative (PID) controller. The system can further include a conductive plate positioned between the digital sample partitioning platform and the heating device. The conductive plate can have a thickness of from about 0.02 mm to about 6 mm. The system can further include a thermal paste positioned between the digital sample partitioning platform and the conductive plate. The system can further include thermal paste positioned between the thermoelectric heating device and the conductive plate. The system can further include a heat sink. The system can further include a fan. The imaging device can have a high numerical aperture, a low magnification, and a large field of view. The imaging device can include a multi bandpass filter.

In some embodiments of the system, the digital sample partitioning platform can be a digital PCR chip. In some embodiments of the system, the digital sample partitioning platform can be a digital droplet PCR platform.

In some embodiments, the universal PCR primers are designed to bind to conserved regions within the sequences of interest. Variable regions within the targeted sequences are required to generate unique melt curves.

In some embodiments, the PCR amplification mix is an optimized PCR master mix. The reaction mixture is loaded onto a digital PCR chip by smearing the reaction mixture across the chip and allowing hydrophobic/hydrophilic interactions to draw the reaction mix into the wells.

In some embodiments, amplification of the target nucleic acid sequence is performed by placing digital PCR chip on flatbed thermocycler and cycling reaction temperature using a standard 3-step PCR cycle. This amplifies the signal given by the DNA dye intercalated within the double-stranded DNA.

In some embodiments, simultaneously heating and imaging the digital PCR chip is performed. The chip is heated in a controlled manner using a Peltier element. The control system can, in some embodiments, use a feedback system to provide temperature feedback to control the heating or cooling of the system. Simultaneously a microscope with a powerful LED and highly sensitive CMOS sensor continuously images the fluorescence of the chip.

The images from the microscope are analyzed using code that automatically reads the intensity from each well and relates it to the temperature of the chip, generating the high resolution melt curves. After normalizing the curves they are identified using a supervised machine-learning code based on the shape and temperature of the melt curves.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 are graphs and schematics demonstrating massively Parallel Digital FIRM Device. (A) Poisson distribution of gDNA in a 96-well plate versus a 20,000 well digital PCR chip, showing the distribution of molecules per well. (B) Schematic of the digital HRM platform. (C) Image of the actual dHRM platform. (D) Fluorescent image of a small portion of chip where background dye (red) and intercalating dye (green) are overlaid. 3D intensity plot of the green channel is shown in inset.

FIG. 2 demonstrates On-Chip dHRM Characterization and Optimization. (A) Image of a portion of the chip, which has been saturated with synthetic DNA such that nearly all wells exhibit green fluorescence of intercalating dye. Upon controlled heating, fluorescence is lost as the DNA denatures. (B) Melting of three synthetic temperature calibrator sequences containing different GC content at optimized ramp rate on-chip compared to bulk qPCR HRM. The mean and standard deviation of the calibration sequence melt curves are shown. (C) A plot of the relationship between voltage and temperature for 5 runs, showing it to remain linear throughout the range of our temperature profile. The standard deviation has a maximum of 1.22° C. at 91.6° C.

FIG. 3 are graphs demonstrating Sampling and Ramp Rate Optimization on the dHRM Chip. (A),(B) *L. monocytogenes* melt curves generated with a low sampling rate on qPCR and dPCR platforms respectively. (C),(D) *L. monocytogenes* melt generated using a high sampling rate on qPCR and dPCR platforms respectively. The synthetic temperature calibrator sequence melting temperature mean and standard deviation are shown in all. Black circle highlights key melt curve shape feature unique to *L. monocytogenes* 16S sequence that dependent on sampling rate.

FIG. 4 are graphs demonstrating OVO SVM Classification of *L. monocytogenes* and *S. pneumoniae*. (A) Two-thousand normalized *S. pneumoniae* (top) and *L. monocytogenes* (bottom) U-dHRM melt curves aligned to 0.1-dF/dT, respectively. These curves were used to train the OVO SVM to classify each bacteria. (B) Histogram of fluorescence intensity values of digital reaction wells with PDF overlay and the intensity value chosen to classify positive from negative marked by dotted line (top). Histogram showing the Tm of each digital reaction with PDF overlay and the Tm value chosen to classify positive from negative marked by dotted line (bottom). Both graphs correspond to a concentration of 458 genomes of *L. monocytogenes* per chip. (C) U-dHRM dilution series of *L. monocytogenes* with U-dHRM measured values plotted against spectrometer measured values for DNA content. The sample mean and sample standard deviation are shown. (D) In blue: qPCR melt curve generated from a 1:1 mix of 20 ng total DNA input of *S. pneumoniae* and *L. monocytogenes*. In red: qPCR melt curve generated from a 1:1 mix of 0.02 ng total DNA input of *S. pneumoniae* and *L. monocytogenes*. This concentration and reaction mixture is similar to that used for digital chip experiments. In grey: qPCR melt curve generated from a negative template control (NTC) with no bacterial DNA added. (E) U-dHRM and OVO SVM classification of *L. monocytogenes* and *S. pneumoniae* in two distinct mixture compositions, demonstrating polymicrobial detection capability. Table 2 shows enumeration of detected curves in panel E.

FIG. 5 are graphs demonstrating identification of *L. monocytogenes* in mock blood sample. (A) Histogram showing the Tm of each digital reaction with PDF overlay and the calculated Tm threshold (dotted line) used to classify true positive from off-target amplification. (B) Bacterial DNA melt curves from reactions identified as positive using the Tm and peak height thresholds adjusted for human DNA background. (C) Melt curves from reactions identified as negative using thresholds specific for human DNA background. This plot highlights the high background noise associated with the addition of human DNA to our sample (D) *L. monocytogenes* melt curves from panel B normalized and aligned to 0.1-dF/dT.

FIG. 6 are graphs demonstrating DHRM melt curves for polymicrobial mixtures from experiment 2 in Table 2. (a) All melt curves. (b) Melt curves that were automatically identified as bacterial using our U-dHRM Tm enumeration algorithm. (c) Melt curves that were automatically identified as background/non-specific using our U-dHRM Tm enumeration algorithm.

FIG. 7 are graphs demonstrating QPCR dilution series standard curves. (a) *S. pneumoniae* DNA (b) *L. monocytogenes* DNA. Slope of linear regime indicates primer efficiency. Red circle marks the condition used in the complimentary U-dHRM experiments.

FIG. 8 is an image of a gel electrophoresis of qPCR amplification products corresponding to FIG. 4(D). L: DNA ladder markers. 1: High concentration template multiplexed with calibrator sequence. 16S target amplicon appears as a band at 1000 bp. Calibrator sequence appears as a band at 60 bp. 2: NTC with calibrator sequence, showing a faint off-target amplification band at approximately 150 bp, just above the calibrator sequences. 3: High concentration template without calibrator sequence included. 4: NTC without calibrator sequence, showing a faint off-target amplification band at approximately 150 bp.

Figure 1A:
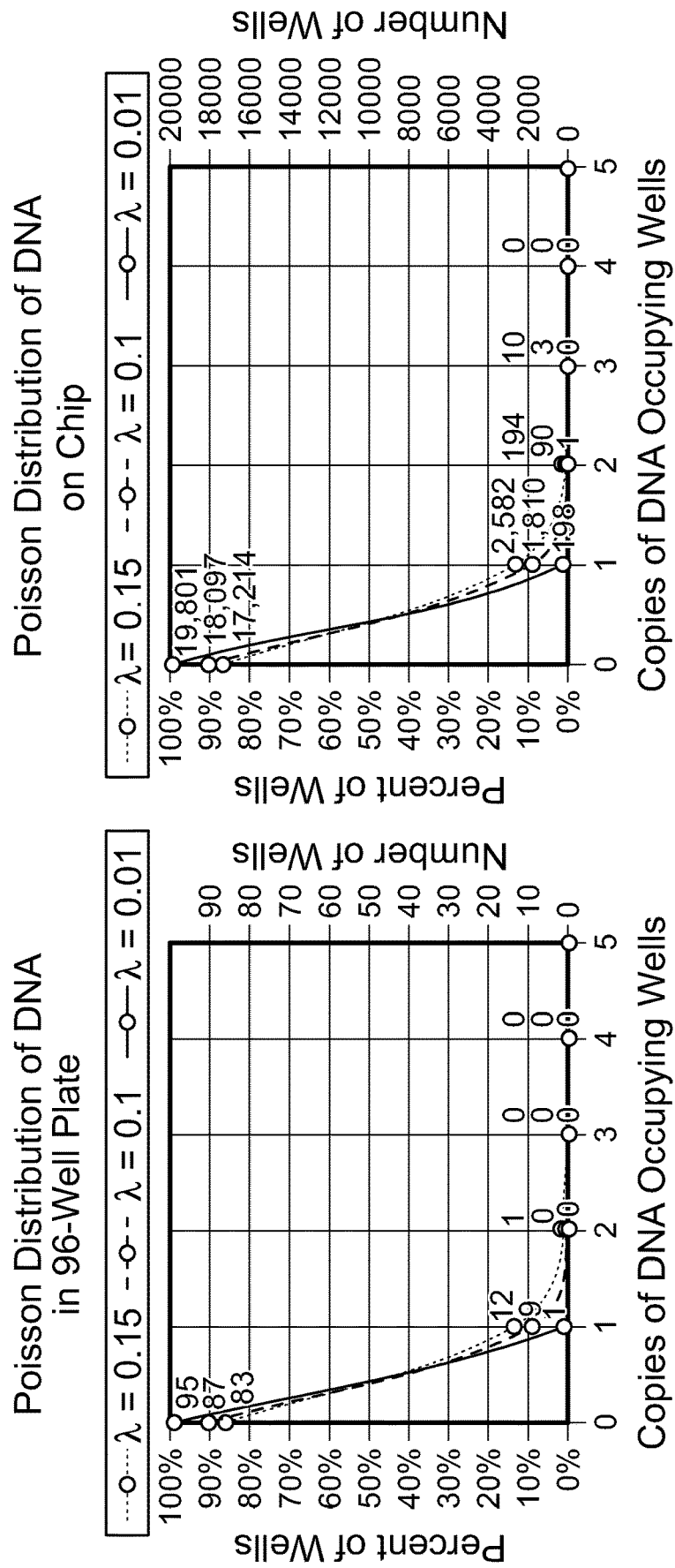

FIG. 11 are graphs of controller performance in the U-dHRM platform described in Example 2. (A) Box plot of error (observed−expected temperature) for the conductive (copper) block across all runs with temperature calibrator at a ramp rate of 0.1° C./s. Red crosses denote outliers that are larger than the 75th percentile plus 1.5×the interquartile range or smaller than the 25th percentile minus 1.5×the interquartile range. This corresponds to approximately ±2.7a and 99.3% coverage assuming normal distribution of the data. At least 2000 wells were chip were used per run. (B) Table with slope and root mean square error for each run shows the highly reproducible ramp rate of 0.1° C./s across runs with average root mean squared error of 0.001° C.

FIG. 12 are graphs of surrogate chip behavior in the U-dHRM platform described in Example 2. (A) Slope and RMSE of fitted thermocouple temperature for each run. The slope of entire run is close to the slope for data in three sections, justifying the use of straight-line fit. Root mean squared error was calculated by comparing the polynomial fit with degree 1 and observed data. (B) Instantaneous ramp rate of acquired thermocouple measurements.

FIG. 13 are graphs of controller performance using three temperature calibrators with known melting temperatures in the U-dHRM platform described in Example 2. (A) Negative derivative of melt (EvaGreen normalized by ROX) with respect to temperature for temperature calibrator sequence. The figure shows difference between $T_m$-interval and their denotation. (B) Mean of difference in $T_m$-intervals are shown. (left) Difference between $T_m$-High and $T_m$-Low ($T_m$-interval-HL) (middle) $T_m$-High and $T_m$-Mid ($T_m$-interval-HM), (right) $T_m$-Mid and $T_m$-Low ($T_m$-interval-ML). (C) Intra-run variability associated with each run. Median absolute deviation (MAD) for (left) $T_m$-interval-HL (middle) $T_m$-interval-HM, (right) $T_m$-interval-ML. The MAD varied from 0.1 to 0.11, 0.09 to 0.12 and from 0.11 to 0.14 for $T_m$-interval-HL, $T_m$-interval-HM, and $T_m$-interval-ML, respectively.

FIG. 14 are graphs depicting intra-run variability in the U-dHRM platform described in Example 2. (A) Variation in (left) $T_m$-High (middle) $T_m$-Mid (right) $T_m$-Low. Variation was calculated as difference in $T_m$ for each well about the mean $T_m$ of the chip. Red crosses denote outliers that are larger than the 75th percentile plus 1.5× the interquartile range or smaller than the 25th percentile minus 1.5× the interquartile range. This corresponds to approximately ±2.76 and 99.3% coverage assuming normal distribution of the data. At least 2,000 wells were chip were used per run. (B) Variation in $T_m$-Mid plotted against variation in $T_m$-High. Figure shows a greater variation in $T_m$-Mid as compared to $T_m$-High (C) Variability in (left) $T_m$-High, (middle) $T_m$-Mid and (right) $T_m$-Low with respect to spatial location of wells on the chip for a characteristic run. Absolute temperature difference about the mean $T_m$ of the chip is shown in false color as indicated in the key to the right. (D) Histogram of temperature difference about the mean $T_m$ of the chip for (left) $T_m$-High, (middle) $T_m$-Mid and (right) $T_m$-Low.

FIG. 15 are graphs of rate dependence of melt curves in bacteria with one or more melt transitions in the U-dHRM platform described in Example 2. (A) Negative first order derivative of melt with respect to temperature for *Acinetobacter baumanii*. (B) Second order derivative of melt with respect to temperature. (C) Negative first order derivative of melt with respect to temperature for *Moraxella catarrhalis*. (D) Second order derivative of melt with respect to temperature. (E) Negative first order derivative of melt with respect to temperature for *Salmonella enterica* serovar Heidelberg. (F) Second order derivative of melt with respect to temperature. The melt curves generated at different rates were aligned to their $T_m$ to compare the shapes across different melt rates.

Figure 14A:
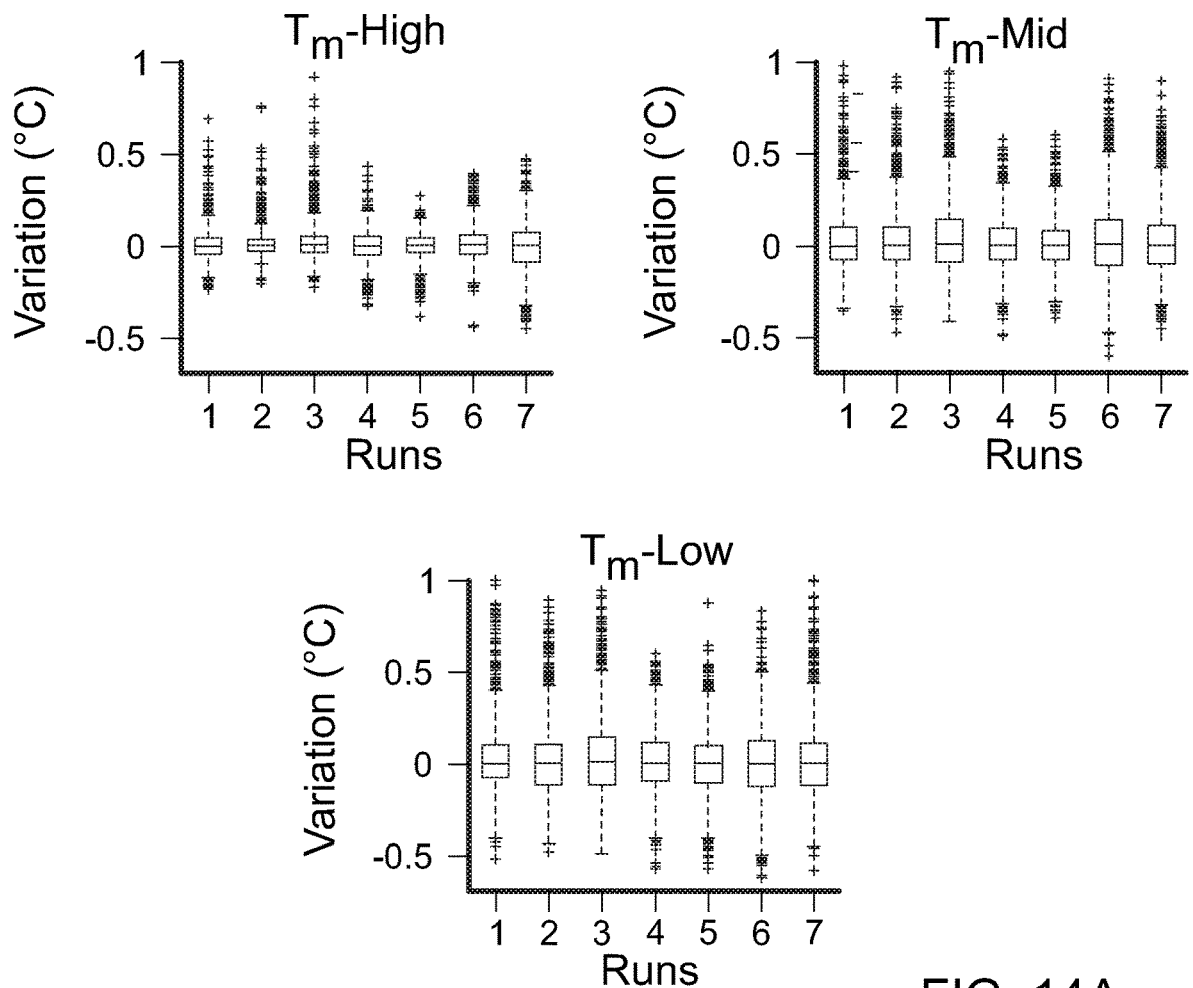
Figure 14B:
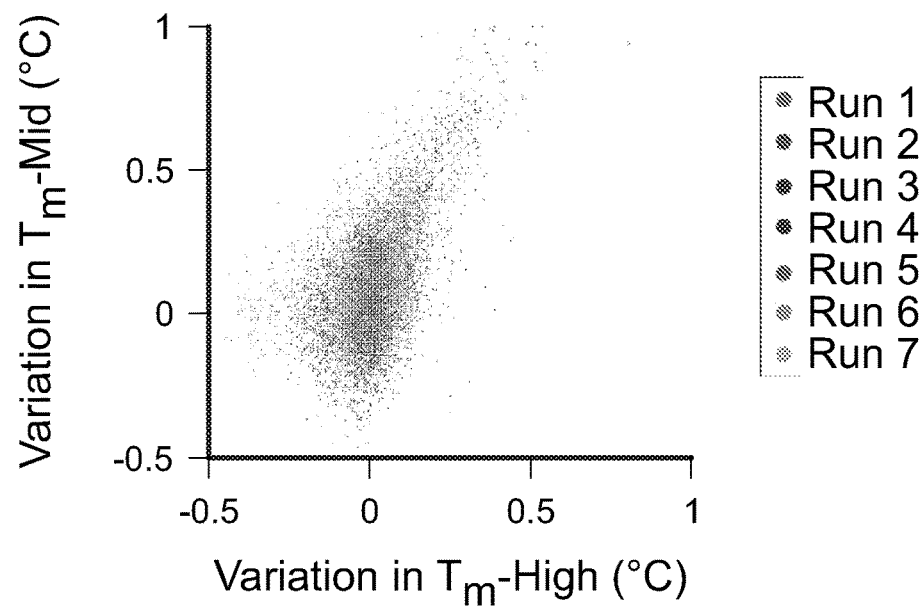
Figure 16A:
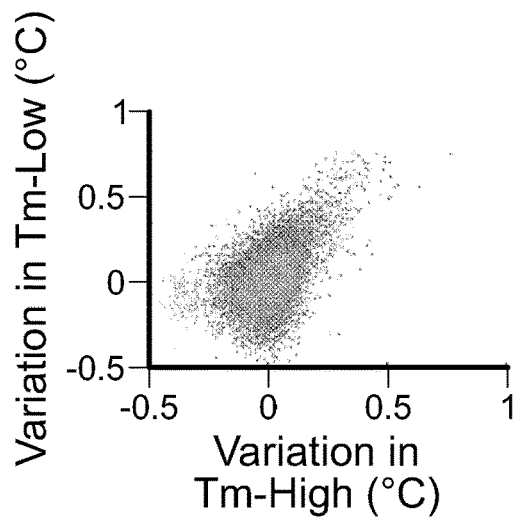
Figure 16B:
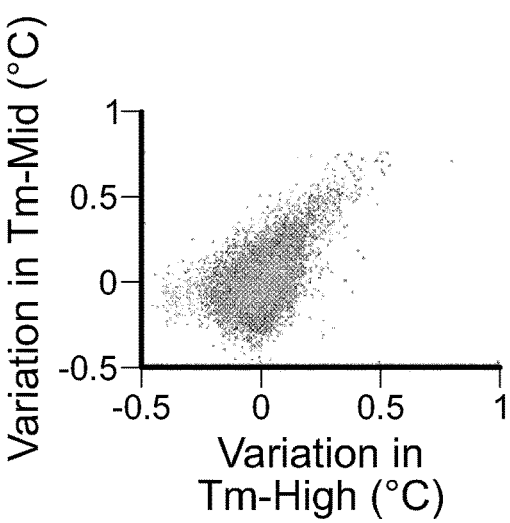
Figure 16C:
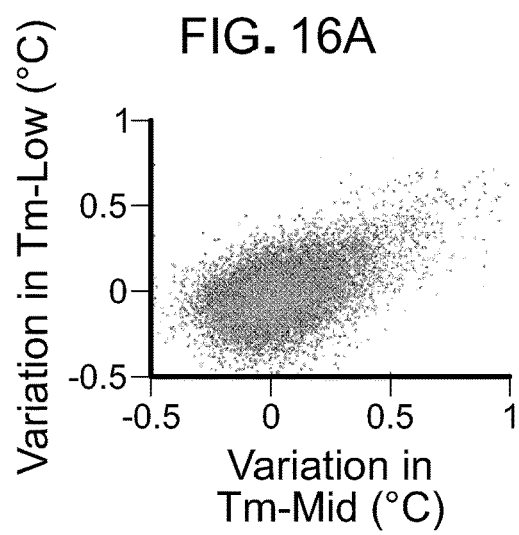

FIG. 16 are graphs of Variation in $T_m$-High, $T_m$-Mid and $T_m$-Low with respect to each other corresponding to FIG. 14B. (A) Variation in $T_m$-Low plotted against variation in $T_m$-High. (B) Variation in $T_m$-Mid plotted against variation in $T_m$-High. (C) Variation in $T_m$-Low plotted against variation in $T_m$-Mid.

Figure 17:
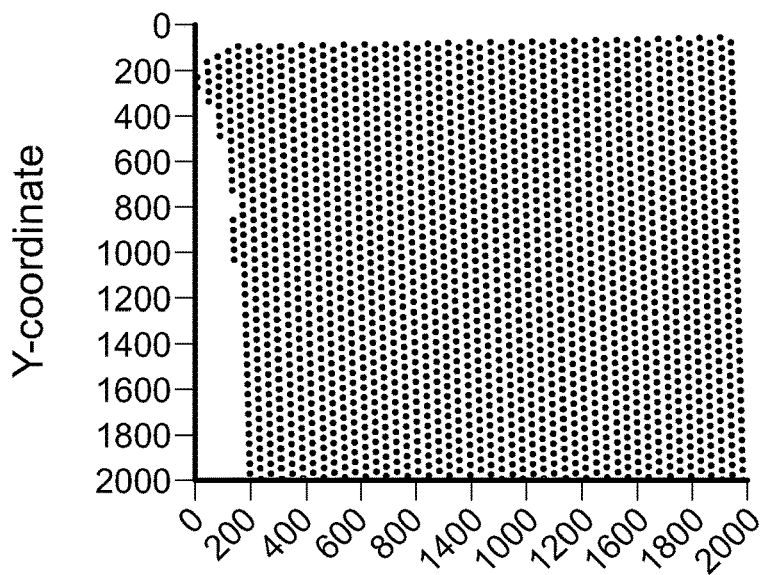

FIG. 17 is a plot of spatial representation of behavior of ROX fluorescence for a characteristic run corresponding to FIG. 14C.

Figure 18:
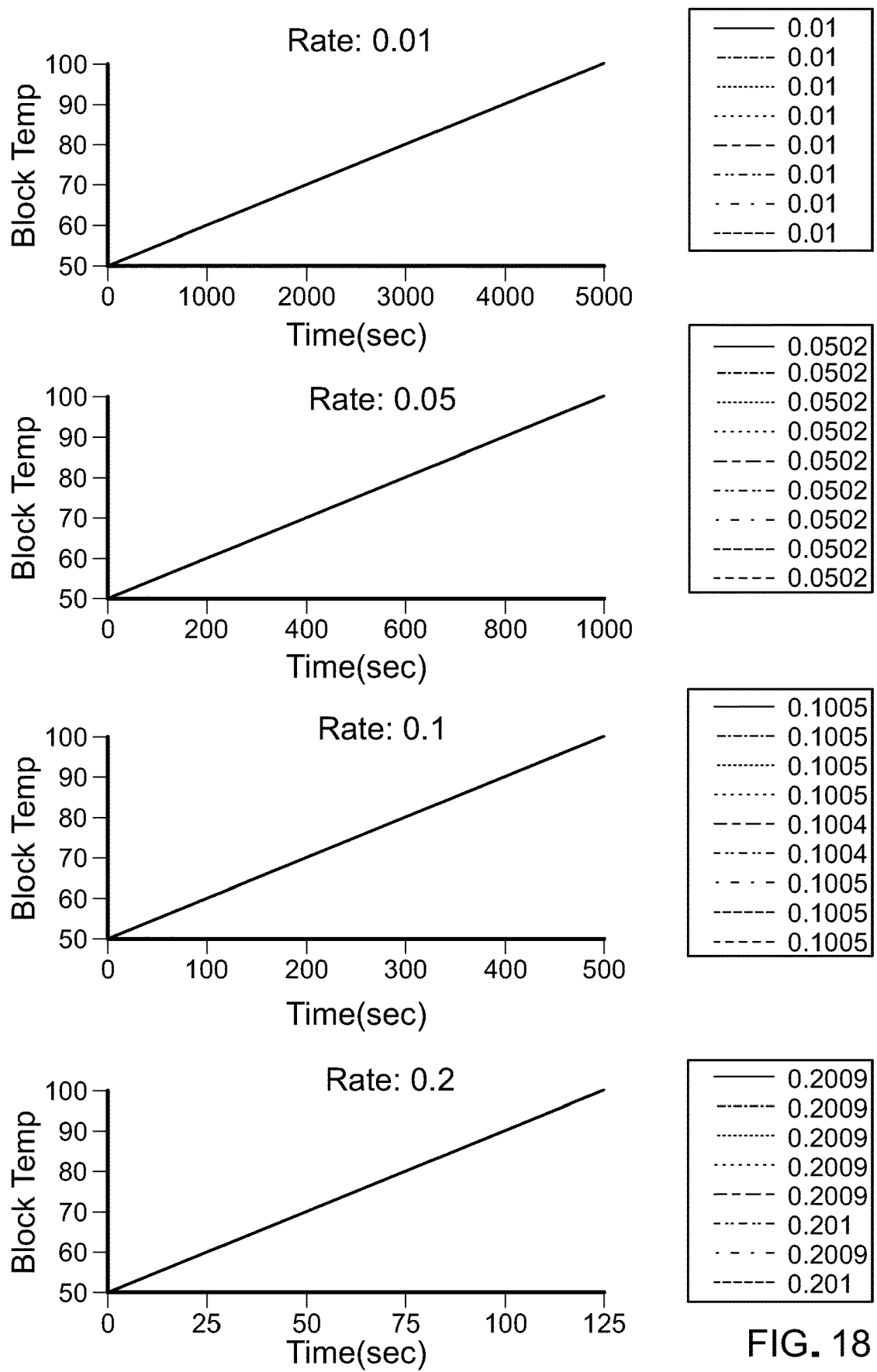

FIG. 18 are graphs of controller performance for different ramp rates. Box plot of error (observed−expected temperature) for the conductive (copper) block across all runs with temperature calibrator at a ramp rate of 0.01° C./s, 0.05° C./s, 0.1° C./s, 0.2° C./s. Slope of straight line fit for RTD temperature for each run.

Figure 19:
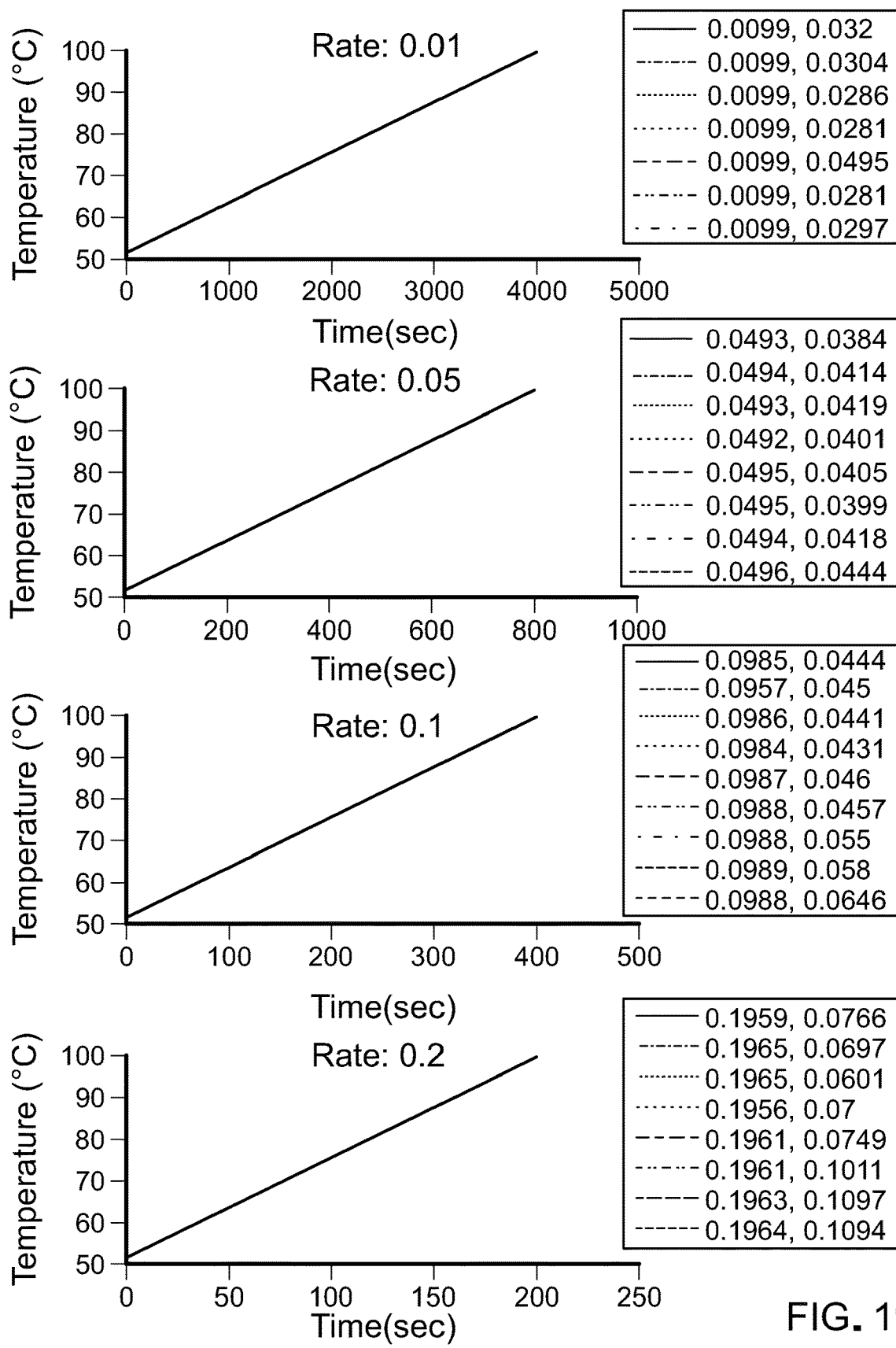

FIG. 19 are graphs of surrogate chip behavior at different rates. Slope and RMSE of fitted thermocouple temperature for each run. The thermocouple data was fitted to a 1-degree polynomial.

Figure 20:
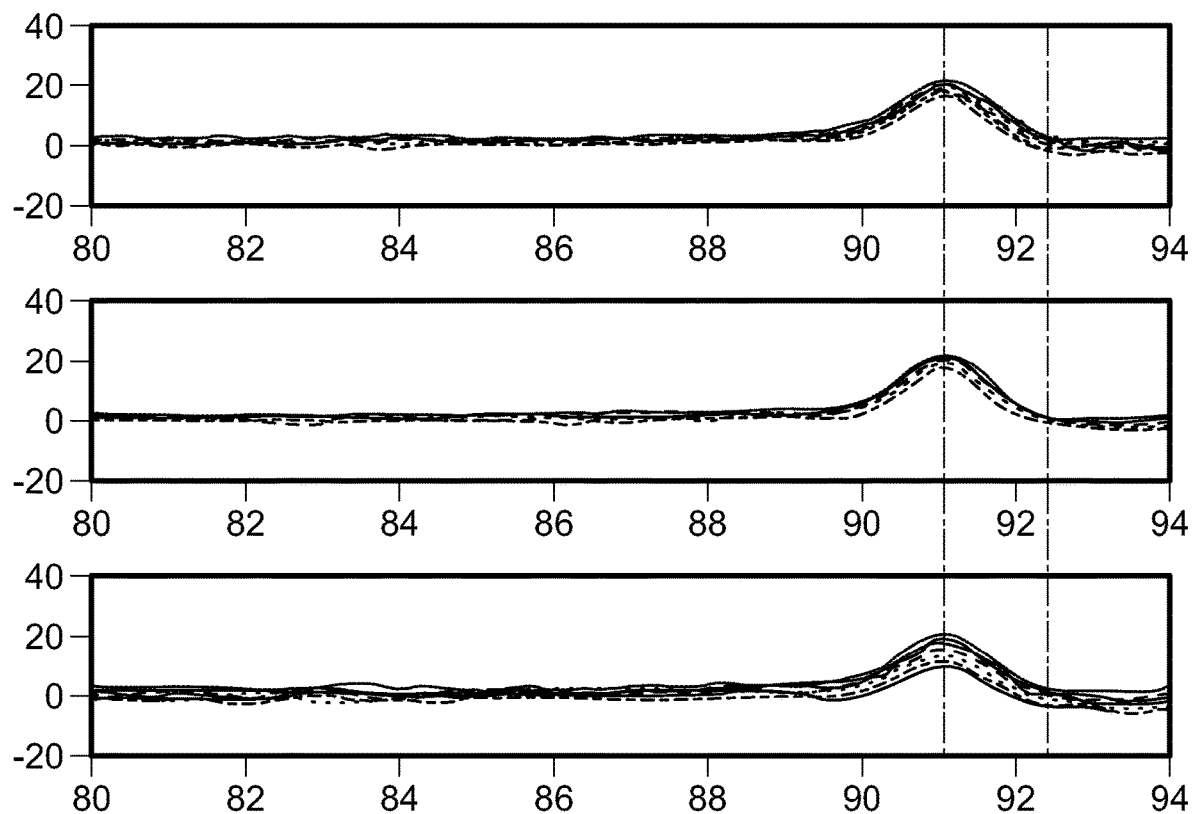

FIG. 20 are graphs of rate dependence of melt curves in bacteria with one melt transition corresponding to FIG. 15. Negative derivative of melt with respect to temperature for *Salmonella enterica* serovars or *Enteritidis Typhimurium*.

Figure 21:
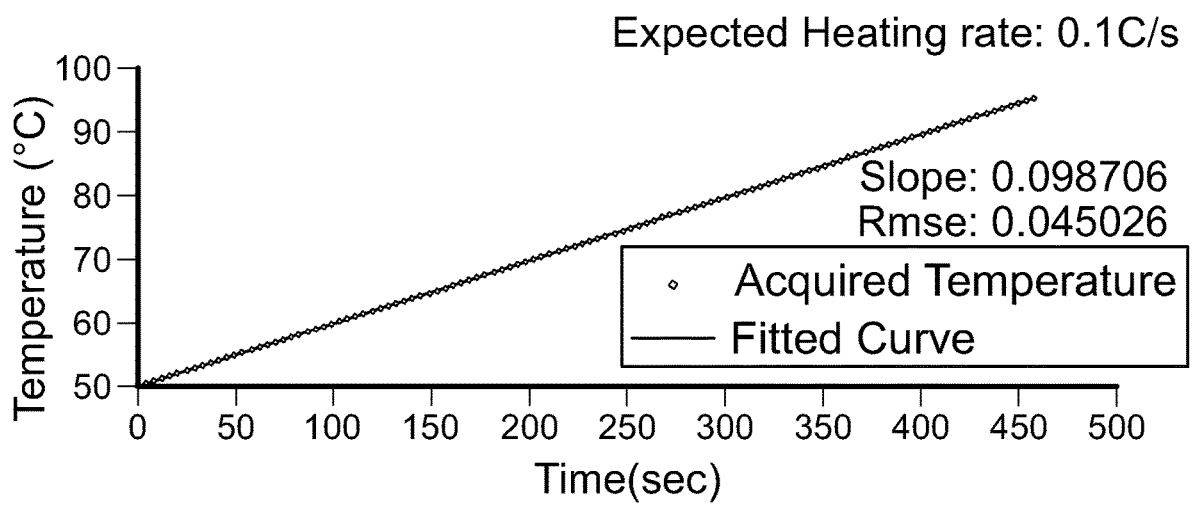

FIG. 21 is a graph showing line fitting to estimate chip temperature. Asterisk shows unique temperature-time pairs acquired by the MS-Elements software. Solid line shows estimated temperature using line fitting for a characteristic run.

DETAILED DESCRIPTION

The present disclosure is based in part of the development of an integrated platform enabling the identification of nucleic acid sequences, such as, e.g., bacterial, viral, or fungal pathogen DNA or RNA sequences, in complex samples, in some cases in less than four hours. In some aspects, the platform incorporates a microfluidic chip or digital droplet platform and instrumentation to accomplish universal nucleic acid amplification, High Resolution Melting (HRM), and machine learning (e.g., profiling of the resultant melt curves with a machine learning-assisted classification algorithm) within at least 20,000 picoliter scale reactions simultaneously. Clinically relevant concentrations of pathogen nucleic acid molecules (e.g., bacterial DNA molecules) are separated by digitization across 20,000 or more reactions and amplified with universal primers. Amplification is followed by HRM sequence fingerprinting in all reactions simultaneously. The resulting pathogen-specific melt curves are identified by one or more machine learning-assisted classification algorithms (e.g., by Support Vector Machine (SVM) learning), and individual pathogen loads can be quantified.

As used herein "nucleic acid amplification" or "amplification" are used interchangeably and refer to reaction in which replication of a nucleic acid sequence occurs repeatedly over time to form multiple copies of at least one segment of a template nucleic acid molecule. Amplification may generate an exponential or linear increase in the number of copies as amplification proceeds. Typical amplifications produce a greater than 1,000-fold increase in copy number and/or signal. Exemplary amplification reactions for the assays disclosed herein may include the polymerase chain reaction (PCR) or ligase chain reaction (LCR), each of which is driven by thermal cycling. Thermal cycling generally involves cycles of heating and cooling a reaction mixture to perform successive rounds of denaturation (melting), annealing, and extension.

Amplification may be performed with any suitable reagents. Amplification may be performed, or tested for its occurrence, in an amplification mixture, which is any composition capable of generating multiple copies of a nucleic acid target molecule, if present, in the composition. An amplification mixture may include any combination of at least one primer or primer pair, at least one probe, at least one replication enzyme (e.g., at least one polymerase, such as at least one DNA and/or RNA polymerase, and/or at least one ligase), and/or deoxynucleotide (and/or nucleotide) triphosphates (dNTPs and/or NTPs), among others.

As used herein, the term "amplicon" refers to a product of an amplification reaction. An amplicon may be single-stranded or double-stranded, or a combination thereof. An amplicon corresponds to a segment or the entire length of a nucleic acid target molecule.

The disclosed platform combines the ability of digital PCR to quantitatively determine sample concentration with the sequence identification of high resolution melt curves enabling counting and analysis of specific sequences within a mixed sample. In a first part of one assay embodiment, the sample is spread across 20,000 PCR reaction wells within a digital PCR chip. All sequences of interest are amplified using universal primers. The high resolution melt curves are generated by heating the amplified sequences in the presence of a DNA intercalating dye and simultaneously imaging the chip to determine fluorescence loss as a function of temperature. Using a machine-learning algorithm the sequences are identified and counted based on their fingerprint melt curves.

High resolution melt alone is capable of sequence identification based on fingerprint melt, but does not provide any quantitative information. Digital PCR is unable to provide quantitative information about mixed samples and is limited by the requirements put in place by TaqMan probes. Sequencing can provide sequence-specific quantitative information, but is limited by short sequence reads making it inappropriate for studying alternative splice variants and by the necessity for a large starting amount of material to give accurate reads.

The platform provides several advantages including, for example, reducing reaction volumes by 99.995% and achieving a greater than 200-fold increase in dynamic range of detection compared to traditional PCR HRM approaches. Type I and II error rates are reduced by 99% and 100% respectively compared to intercalating dye-based digital PCR (dPCR) methods. The platforms described herein reduce errors resulting from temperature gradients across sample plates. The platform allows for sensitive melt curve analysis, including heating-rate-dependent analysis. With the platforms described herein, identification and quantification of multiple species and even multiple variants within same species organisms can be achieved from heterogeneous samples, including samples contaminated with host or other non-target DNA and RNA. Thus, the methods and systems disclosed herein impact a number of quantitative profiling applications, especially infectious disease diagnostics. Additionally, some embodiments of the platform provide improved uniformity and linearity of thermal control during melting analysis in general.

The combined capabilities of universal dHRM offer significant advantages over qPCR, microarray, and even NGS profiling approaches, especially for infectious disease detection where breadth of detection, timing, and cost are critical factors. The ability to quantify even low level organisms in polymicrobial samples within hours significantly impacts clinical microbiology diagnostic practice, where patients suspected of bloodstream infection suffer from an hourly increase in mortality risk due to lack of diagnostic information and inaccurate treatments. Moreover, retrospective studies suggest that absolute quantification of bacterial genomic load in patients may useful to assess severity of infection and to predict prognosis in sepsis cases.

The term "high resolution melt" or "HRM" refers to a technique for determining a sequence variation in a nucleic acid by analyzing a melting curve of the nucleic acid. The nucleic acid can be double-stranded or single-stranded. In some embodiments, a signal representing a double-stranded nucleic acid can be measured in real time. In some embodiments, real time measurement (Ct) of the PCR can be used as a quality control value for melt analysis such as HRM analysis. In some embodiments, end point analysis can be employed. In some embodiments, single-stranded nucleic acids can be analyzed, for instance, single-stranded nucleic acids can fold to form duplexes or other higher ordered structures that can then be analyzed. Herein, the term "high resolution melt" or "HRM" can also refer to a technique for determining sequence variations between two different nucleic acids by analyzing the shape of the melting curve including the melting temperature and the slope.

HRM has been validated as a rapid, inexpensive, closed-tube DNA sequence characterization technique. Precisely heating and unwinding post-PCR DNA amplicons in the presence of a fluorescent intercalating dye[8-10] or sloppy molecular probes[11,12] loss-of-fluorescence melt curves are generated, providing unique DNA sequence signatures. The expansion of HRM into a broad-based profiling technology by preceding it with universal PCR 13 has been proposed. Priming conserved DNA regions flanking genetic variation sites or mutations, genetic locus sequence differences can be identified by changes in the gene amplicon melt curve signature. This universal HRM technique replaces the need for targeted primers or probes and relies only on the intrinsic melting properties of the amplified sequence. Universal HRM methods have been developed for several applications, including identification of oncogenic mutations[14], gene methylation patterns[15,16], and bacterial identification[17-22]. The inventors previously advanced universal HRM to enable single nucleotide specificity for the discrimination of microRNA in the Lethal-7 family and for species-level identification of bacteria using the 16S gene[23,24]. However, if multiple sequence variants are present, as often occurs in clinical samples, individual sequences cannot be identified in the conventional universal HRM format consisting of a single bulk reaction[13,25]. Likewise, although generally reproducible melt curves are obtained, in-run template standards are typically required to overcome run-to-run variability and enable curve matching by user intensive curve identification procedures. These shortcomings have restricted the application of universal HRM to primarily pure homogeneous samples, constrained the breadth of profiling to only a few sequence variants, and limited the technique's specificity, since single nucleotide changes often manifest as very slight temperature or curve shape changes.

The inventors previously developed an approach called universal digital high resolution melt (U-dHRM) by integrating universal amplification strategies and temperature calibrated HRM with limiting dilution digital PCR (dPCR) in a 96-well plate format[23]. The inventors demonstrated that this approach, in principle, could overcome many limitations of current profiling technologies to achieve single nucleotide specificity, broad-based detection, single molecule sensitivity, and absolute quantification simultaneously. Separately, the inventors developed machine learning approaches using nested, linear kernel, One Versus One Support Vector Machines (OVO SVM) to automatically identify sequences by their melt curve signatures despite inherent experimental variability[24,26]. Through these approaches, the inventors have shown that U-dHRM is capable of automatically identifying multiple distinct genotypes in a mixture with single molecule sensitivity and single nucleotide specificity. Others have also demonstrated the ability of U-dHRM to sensitively detect rare mutants/variants[27,28] and also novel variants[29]. These findings suggest that U-dHRM has the potential to offer desirable features for several profiling applications that require a combination of speed, sensitivity, quantitative power, and broad profiling ability. However, no platform exists for accomplishing U-dHRM in a high-content format required to reach a clinically relevant dynamic range of detection.

The sensitivity and quantification power of U-dHRM profiling relies on full digitization of the sample, i.e. spreading the sequence mixture across many reactions so each target molecule is isolated from others. Since the process of loading DNA into wells is stochastic at limiting dilutions, the dynamic range of single molecule detection follows a Poisson distribution, requiring the total number of reactions to be approximately 10 to 100 times the number of sequence molecules. That is, the average occupancy ($\lambda$) across all reactions must be 0.1 to 0.01 copies of DNA per well. The probability of DNA occupancy in any well, i.e. the fraction of wells having 1, 2, 3, etc. copies, is given by the Poisson probability distribution $P=(e^{-\lambda}*\lambda^n)/n!$, where n is the total number of wells. U-dHRM is currently performed in traditional PCR multi-well plates using FIRM enabled qPCR machines. In this format, only about 9 molecules in a sample can be profiled at the single molecule level per 96-well plate (FIG. 1(A), left). Therefore, a major challenge to the advancement of HRM-based profiling is the need for an exponential increase in the number of reactions to achieve scalability for realistic sample concentrations. To this end, a microfluidic U-dHRM system could offer the necessary scalability. Although several reports have documented the use of microfluidic chambers or droplets for dPCR, these platforms cannot accomplish U-dHRM. Microvalve-based dPCR devices (e.g. Fluidigm's qdPCR) do not have high resolution heating blocks necessary for high resolution melt curve generation and moreover are not programmed to capture fluorescence during heat ramping or identify sequence-specific curve signatures. Microfluidic droplet-based digital PCR devices (e.g. Bio-Rad's ddPCR) perform endpoint PCR detection in a continuous flow format without temperature control, one droplet at a time, which prevents in-situ, real-time monitoring of fluorescence in droplets, as is needed by U-dHRM. To address these challenges, we developed a platform that accomplishes massively parallelized microfluidic U-dHRM and integrated this platform with the inventors' machine learning curve identification algorithm. The inventors' technology achieves single molecule sensitive detection and absolute quantification of thousands of bacterial DNA molecules in polymicrobial samples in less than four hours. The inventors show proof of principle in mock blood samples that highly sensitive, specific, and quantitative bacterial identification is achieved in samples containing a high background of human DNA.

In one aspect, the present disclosure provides a digital melt analysis platform that integrates sample partitioning, along with heating and imaging components. The sample can include one or more target nucleid acid sequences. In some embodiments, the sample can be a heterogeneous sample. In some embodiments, the sample can include mammalian DNA, bacterial DNA or RNA, viral DNA or RNA, fungal DNA or RNA, or combinations thereof. The methods, systems, and devices of the present disclosure can perform highly sensitive high throughput, multi-dimensional, DNA melting analysis to achieve nucleic acid sequence fingerprinting, screening, and anomaly detection with single molecule sensitivity. The methods, systems, and devices of the present disclosure achieve simultaneous high sensitivity imaging and precisely controlled heating of arrayed, small volume, low thermal mass, single molecule nucleic acid amplification reactions partitioned according to a digital assay platform, such as digital PCR (dPCR) or droplet digital (ddPCR). The methods, systems, and devices can include pairing the integrated platform with classification systems (e.g., machine learning algorithms) to correct for errors and analyze the melt curves for identification and quantification.

In one aspect of the methods, assays, and systems described herein, a sample, e.g., a heterogeneous sample, is fractionated or partitioned into many small volume PCR reactions, such that each reaction contains two or fewer target molecules, or zero target molecules, or one target molecule. Thus, amplicons resulting from each reaction will, in some cases originate from two or fewer target nucleic acid molecules in the sample, less than two target nucleic acid molecules in the sample, or one or fewer target nucleic acid molecules in the sample. Each partitioned reaction can have a discrete volume that is the same or different from other reactions originating from the same sample. In some embodiments, the partitioned reactions are contained within, for example, a droplet in a ddPCR platform or a well on a dPCR chip. Each reaction can have a volume of one nanoliter or less, one picoliter or less, or less than about one picoliter. dPCR chips are microfluidic devices that allow partitioning and manipulation of small volumes or droplets of samples and/or reaction mixtures using electrowetting or electrophoresis. ddPCR platforms divide reaction mixtures into water-in-oil droplets using a combination of microfluidics surfactant or detergent.

In some embodiments, partitioning a sample or reaction mixture includes partitioning the sample or reaction mixture into at least 10,000 partitions, droplets, or wells. In some embodiments, partitioning a sample or reaction mixture includes partitioning the sample or reaction mixture into at least 20,000, at least 50,000, at least 100,000, at least 200,000, at least 500,000, or at least 1,000,000 partitions, droplets, or wells. Partitioning platforms useful in the methods and systems described herein include droplet digital platforms and digital microfluidic chips.

The term "droplet" refers to a volume of liquid. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, combinations of such shapes, and various shapes formed during droplet operations, such as merging or splitting or formed as a result of contact of such shapes with one or more surfaces of a droplet actuator (i.e., a device for manipulating droplets). Moreover, a droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids.

In some embodiments, the sample or reaction mixture is partitioned on a microfluidic chip platform, including chips having an array of reactions configured such that the reactions can fit into a single field of view for imaging. For example, in some embodiments, a dPCR chip may be used. Exemplary dPCR chips can include, for example, a silicon substrate etched with nano-scale or smaller reaction wells. In some embodiments, a dPCR chip has a low thermal mass. For example, the chip may be constructed of thin, highly conductive materials that do not store heat energy. In some embodiments, a dPCR chip has a surface area of from about 50 mm$^2$ to about 150 mm$^2$. In some embodiments a dPCR chip has a surface area of about 100 mm$^2$. Limiting the surface area can allow for greater uniformity of heating of the chip during melt analysis and a reduction in run-to-run variation in the melt cure analysis, a reduction in errors in melt curve generation, and increased discrimination of melt curves in the analysis.

In some embodiments, the sample or reaction mixture is partitioned in a droplet digital platform such as ddPCR. Continuous-flow droplet systems can, in some embodiments, provide enhanced processing speed through limiting heat inertia mostly to the droplet sample's thermal mass.

The inventors have discovered that, in some embodiments, smaller reaction volumes can enable improved sensitivity as compared to typical PCR volume formats by, e.g., reducing the effective level of background DNA and inhibitors that interfere with nucleic acid amplification and DNA melt analysis for successful amplification and HRM from single molecules. It has further been discovered that smaller reaction volumes allows for a higher packing density of reactions such that all reactions can be imaged simultaneously using a large field of view camera. Imaging all reactions simultaneously includes collecting all melt curves for individual target sequences simultaneously, resulting in faster throughput of HRM and more efficient error reduction. Additionally, it has been discovered that increasing the number of reactions analyzed enables a higher dynamic range of detection and higher throughput of HRM.

One or more samples having a target nucleic acid are combined with other components to generate a reaction mixture. Reaction mixture components can include, in addition to the sample, e.g., one or more universal amplification primers, one or more DNA intercalating dyes, and reagents for amplifying a target nucleic acid. In some embodiments, the reaction mixture can be generated prior to loading the sample contained in the reaction mixture onto the dPCR chip or ddPCR platform. In some embodiments, the sample can be loaded onto the chip or ddPCR platform and partitioned prior to mixing in the remaining components of the reaction mixture. In some embodiments, different components of the reaction mixture can be added at different times or stages. For example, any of the reaction mixture components described herein can be added simultaneously before or after partitioning. In another exemplary embodiment, some reaction mixture components may be added to the sample prior to partitioning, while other components may be added later, such as after partitioning.

The reaction mixture can include one or more universal amplification primers. Exemplary universal amplification primers useful in the methods and systems described herein include bacterial primers, fungal primers, viral primers, and combinations thereof. Some examples of useful primers include universal primers targeting the bacterial 16S gene, Flavivirus NS1, NS3, NS5, and 3' NC gene regions, and fungal internal transcribed spacer 1 (ITS1), internal transcribed spacer 2 (ITS2), 5.8 s rDNA, 18S, and 28S gene regions may be targeted. In some embodiments, the reaction mixture can include combinations of at least two, at least three at least five, or at least ten unique universal amplification primers. In some embodiments, the reaction mixture can include between two and six unique universal amplification primers. In some embodiments, combinations of primers allow multiplexing for broad-based detection of multiple taxonomic units of organisms in a single sample.

In some embodiments, detection of bacterial, fungal, and viral pathogens can utilize different fluorescence channels. For example, a well-characterized universal fungal primer set targeting the ITS-1 region can be redesigned with a FRET quenched blue fluorophore (LUX primer technology, Thermo Fisher) such that upon incorporation into an amplicon, blue fluorescence will be generated. Similarly, a primer set targeting the HSV I and II DNA polymerase gene can be labeled with a Cy5 probe. Reactions positive for only green fluorescence can be analyzed according to the bacterial and resistance gene databases, while reactions positive for blue and green fluorescence will be identified as fungal and reactions positive for Cy5 fluorescence can be identified as HSV. Such multiplexed system can allow sorting of fungal and viral melt curves from bacterial and resistance melt curves, and can, in some embodiments, effectively triple the temperature range of melt curve output. In some multiplex embodiments, melt curve can be generated in a single fluorescence channel for all DNA, while fluorescence in other channels determines which database will be used for pathogen identification.

In some aspects, the amplification reactions described herein amplify an amplicon having a size greater than 500 base pairs, 750 base pairs, 1000 base pairs or 1500 base pairs in length. While not being bound by theory, it is believed that an amplicon having a size greater than 500 base pairs, 750 base pairs, 1000 base pairs or 1500 base pairs in length allows for improved sequence discrimination and/or identification, thus minimizing background detection of degraded environmental/non-relevant DNA, which is shorter in length.

The reaction mixture can include reagents for amplifying a target nucleic acid, such as one or more polymerases. In some embodiments, the polymerase is a high fidelity polymerase, such as a Phusion or similar high fidelity polymerase. The use of high fidelity polymerase can improve yield and allow for reduced reaction volume, as well an ensure accuracy of amplification to result in more accurate melt curve analysis.

The reaction mixture can also include one or more buffers. In some embodiments, the buffer is a high fidelity buffer. In some embodiments, buffer hydrophilicity is optimized by addition of detergents or surfactants to enable reliable loading of master-mix into reactions on a digital PCR chip or in droplet digital PCR reactions. One or more detergents or surfactants can be present at a concentration of from about 0.005% to about 0.85% v/v, or from about 0.01% to about 0.8% v/v. In an exemplary embodiments, from about 0.01% to about 0.8% v/v Brij L4 can be included in the reaction mixture.

The reaction mixture can include one or more DNA intercalating dyes. During melt the fluorescence of the DNA intercalating dye is lost as a function of temperature, allowing for imaging and measurement of the melt curve of the amplicon. In some embodiments, low-inhibitory DNA intercalating dyes can be used. For example, in some embodiments, EvaGreen dye (Biotium) can be included in the reaction mixture. Other exemplary dyes useful in the methods and systems described herein include SYBR Green, Chai Green, LC Green, BoBo, ToTo, and the like.

In some embodiments, the reaction mixture can include one or more reference dyes. Reference dyes are non-DNA-interchalating dyes that allow for excluding noise values in the melt curve analysis. In some embodiments, the reference dye is used to normalize the melt dye (DNA interchalating dye) at each temperature point. Any passive water soluble dye that does not interfere with PCR or melt analysis can be used. Some exemplary reference dyes useful in the methods and systems described herein include Tamra, TexasRed, AlexaFluor, Rox, and the like.

Following loading of the reaction mixture onto a dPCR chip or ddPCR platform, universal PCR is conducted, then a melt analysis is conducted for all reactions simultaneously. Since each reaction amplifies from a single target molecule, each digital melt curve is a sequence fingerprint of only one sequence within a given heterogeneous sample. Some methods and systems described herein use an integrated dPCR chip or ddPCR platform, heating device, and imaging device.

Figure 1B:
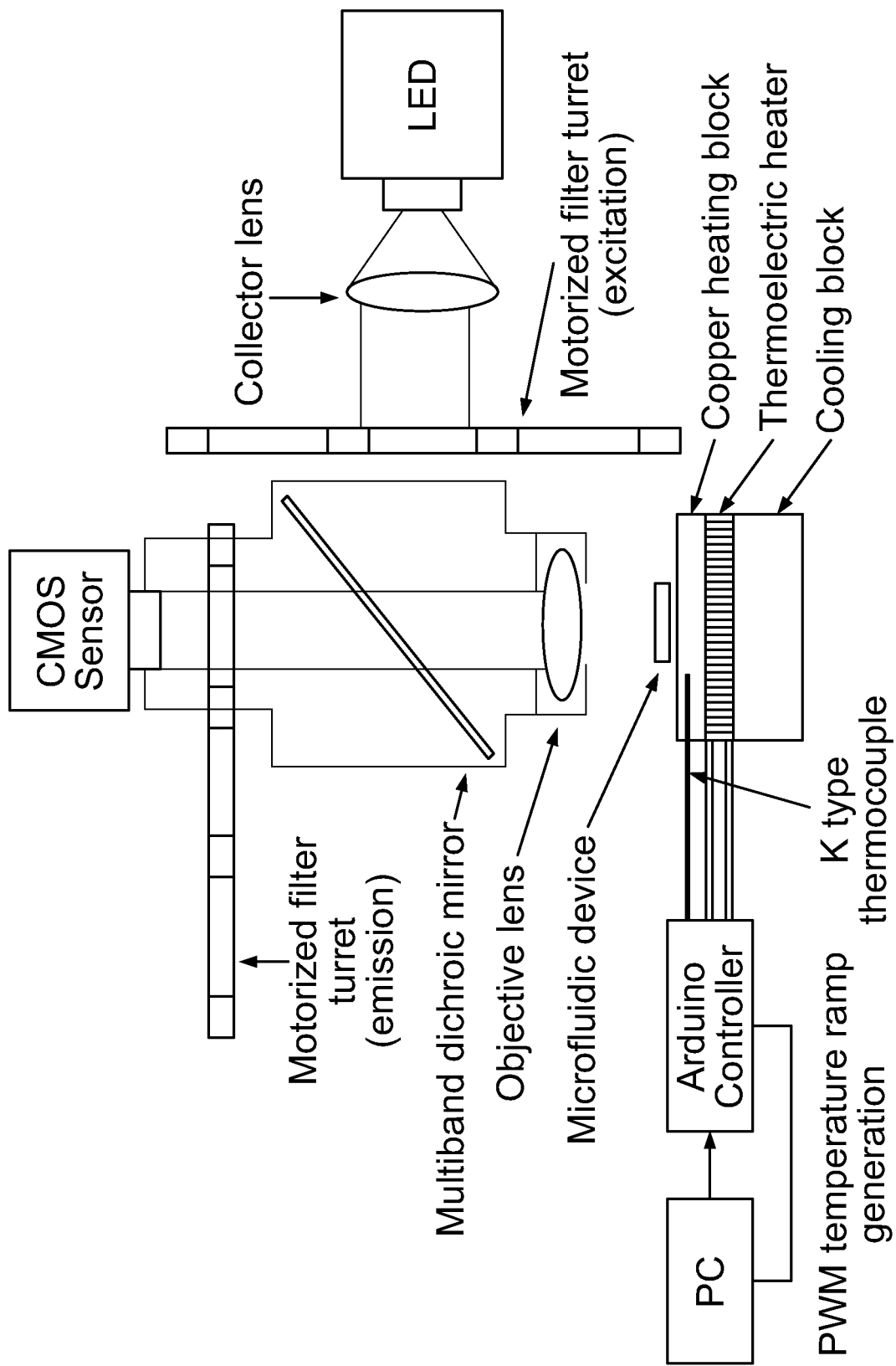

One exemplary embodiment of a system described herein and useful in the methods described herein is shown in FIG. 1B. The PCR reactions are performed on a microfluidic device or dPCR chip, which is supported on a conductive (e.g., gold, silver, copper) heating block. A thermoelectric heater is controlled by a temperature controller, for example an Arduino controller, to heat the microfluidic device or dPCR chip for melt curve analysis of the reactions. An imaging device captures the loss of fluorescence of the DNA interchalating dye during the melt procedure to determine melt curves for the individual reactions.

Figure 9:
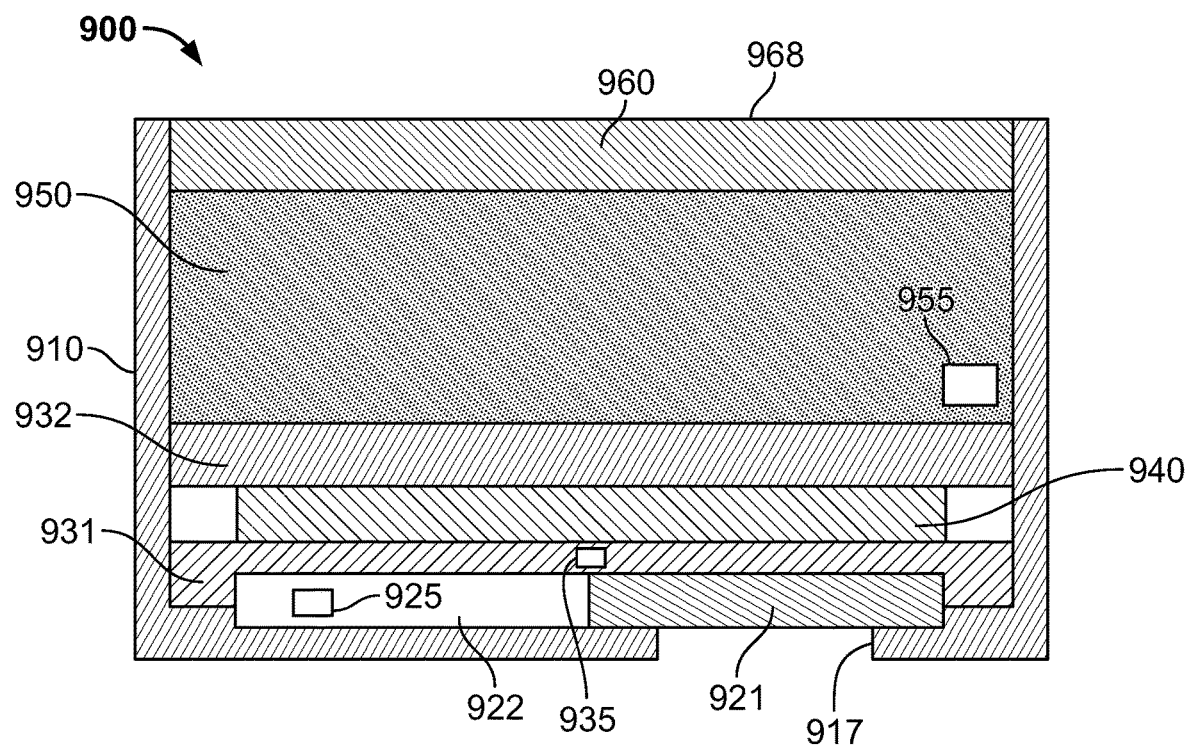
FIG. 9 is a cross sectional view of a portion of an exemplary system embodiment of a U-dHRM platform described herein.

An embodiment of a reaction and heating portion 900 of an exemplary system described herein and useful in the methods described herein is shown in FIG. 9. Enclosure 910 holds a heating portion and dPCR chip reaction portion within a larger system that includes, e.g., an imaging device (not shown), and one or more devices (not shown) configured to, e.g., control the thermoelectric device and perform melt curve analyses of the images captured by the imaging device. Enclosure 910 can act as a stage adaptor to securely mount the chip-heating device assembly on or near a microscope or other imaging device.

A dPCR reaction chip 921 holds the reaction mixture adjacent to an opening 917 in the enclosure 910 for imaging the reactions with an imaging device. In some embodiments, a surrogate dPCR chip 922 may also be present within the enclosure. The surrogate chip 922 can, in some embodiments, include a temperature feedback device or sensor 925 (e.g., a thermocouple or a resistance temperature detector (RTD)) to provide data for estimating the temperature inside the reaction dPCR chip and determining when the dPCR chip reaches the target temperature. In some embodiments, a temperature feedback device or sensor (e.g., a thermocouple or a resistance temperature detector (RTD)) can be placed within the dPCR reaction chip rather than a surrogate chip. In some embodiments the temperature feedback sensor can be situated in the center of a dPCR chip.

The one or more dPCR chips 921, 922 are positioned adjacent, or embedded in a first conductive block or plate 931. The conductive block or plate can be any conductive material, such as, for example, gold, silver, copper, copper polished with gold, or any other material that allows for efficient heat transfer. In some embodiments, the first copper block can have a thickness of between about 1 mm and about 10 mm, about 2 mm and about 8 mm, or between about 0.02 mm and about 6 mm. In some embodiments, the conductive block can be u-shaped, with side walls ranging from about 1 mm to about 5 mm in thickness and a base ranging from about 1 mm to about 10 mm in thickness. In some embodiments, a thin conductive film can be used. The conductive block 931 is position between the one or more dPCR chips 921, 922 and a thermoelectric device 940. The thermoelectric device 940 is used to heat the dPCR chip to melt target nucleic acid molecules for melt curve analysis.

The thermoelectric device 940 can be controlled by a controller (not shown), such as, e.g., a proportional, integral, derivative (PID) controller. The controller can also control optional fan 960, such as by turning the fan on or off and/or controlling fan speed. Fan 960 that has a surface 968 exposed to air at room temperature. In some embodiments, the controller receives feedback from one or more sensors, such as, e.g. a sensor 935 embedded in the conductive block 931, or sensor 955 embedded in heat sink 950. Control of the fan can be based on, e.g., data from one or more sensors such as the heat sink sensor 955. In some embodiments, sensor 935 is embedded in the center of conductive block 931. In some embodiments, sensor 955 is embedded in the center of heat sink 950. The heat sink 950 and fan 960 can provide enhanced and controllable heat dissipation, allow for minimization of between-run times, and improve the ability to heat precisely to higher temperatures.

The sensors can provide temperature feedback to the temperature controller to allow for fast and sensitive control of the system temperatures through control of the thermoelectric device 940 and the fan 960. Sensors useful in the system include, e.g., RTD sensors, negative temperature coefficient (NTC) thermistors, and the like. In some embodiments, a second conductive block or plate 932 is positioned between the thermoelectric device 940 and heat sink 950. Sensors can provide feedback control of the heating and cooling system. In some embodiments, thermal paste or thermal grease (not shown) may be present at an interface between the dPCR reaction chip and the first conductive block, the dPCR surrogate chip and the first conductive block, the thermoelectric device and the first conductive block, the thermoelectric device and the second conductive block, or combinations thereof. Thermal paste can improve heat transfer between the various components of the system, e.g., between the conductive block and the dPCR chip. Exemplary thermal pastes or greases that can be used include, e.g., Arctic Silver 5 Thermal Compound and OmegaTherm 201. In some embodiments, the inclusion of sensors and/or thermal paste can allow for repeatable heating between runs, limit instantaneous error and fluctuations, and reduce the need for visual inspection of the melt curve data or curve shifting based on between-run heating fluctuations. In some embodiments, temperature of the first conductive block can be controlled precisely with a maximum error of 0.004 C difference between the expected temperature and the actual temperature.

The exemplary embodiment of FIG. 9 depicts use of a dPCR chip, however, a one skilled in the art would recognize that a similar systems can be created utilizing a ddPCR platform.

The systems can further include an imaging device for imaging the loss of fluorescence of the DNA interchalating dye during heating of the platform to conduct melt curve analysis. In some embodiments, the imaging device can include a microscope. The imaging device can, in some embodiments, have a high numerical aperture, low magnification, a large field of view, or combinations thereof. The imaging device is configured to simultaneously capture all wells/melt curves without compromising signal quality. In some embodiments, the imaging device is configured to simultaneously image a dPCR chip having a size of 10 mm by 10 mm and containing 20,000 reactions in a single field of view (FOV). In some embodiments, the imaging device can provide fast triggering of the fluorescent light source. In some embodiments, the imaging device includes a polychroic or multi bandpass filter. In some embodiments, the imaging device is configured to enables near simultaneous imaging of DNA interchalating dye and reference dye in two channels (e.g., red and green fluorescence) while maintaining a rapid heating and imaging rate. In some embodiments, the imaging device is configured to maintain high temperature resolution in the generated melt curves (images of the melt dye captured per degree rise in temp). In some embodiments, the imaging device is configured to capture two fluorescent channels at each temperature point by triggering the light source at from about 50 cycles per second to about 100 cycles per second (about 50 Hz to about 100 Hz. In some embodiments, the imaging device is configured to trigger the light source at from about 50 cycles per second to about 100 cycles per second (about 50 Hz to about 100 Hz) when the target heating rate of the dPCR chip or ddPCR platform is from about 0.25 C to about 1° C. per second such that the heating and imaging are synchronized.

In some embodiments, the imaging device is configured to simultaneously image in multiple light channels while the dPCR chip or ddPCR platform is being heated. In some embodiments, the system can achieve multiple channel fluorescence (i.e., a two-channel fluorescence, a four-channel fluorescence, a six-channel fluorescence, etc.) necessary for bacterial, fungal, and viral detection in a simplified and rapidly-triggered optical configuration. In some embodiments, a motorized filter wheel may be used. In some embodiments, a filter slider can be used host a single custom exciter-emitter filter cube, which can be multibandpass with a polychroic mirror (Chroma) to reflect 2, 3, 4, 5, 6, 10, or more excitation spectra and allow the respective number of emission spectra to pas through. For example, a custom filter slider can be used to enable simultaneous imaging of EvaGreen melt curves in FITC channel, ROX loading control in TRITC channel, and LUX primers in DAPI and Cy5 channels while avoiding slow motorization speeds of a filter wheel.

The systems can further include an analysis device having a processor configured to perform machine learning for automated melt curve classification. In performing the melt analysis of the amplicon by simultaneously heating and imaging the digital PCR chip or ddPCR platform, a melt curve for the amplicon is produced. The analysis device processor can be configured to profile the sequence of the target nucleic acid by comparing the melt curve for the amplicon to a plurality of melt curves from different nucleic acid sequences. The plurality of melt curves can include at least one reference melt curve from a known nucleic acid sequence. The analysis device processor can be configured to automate profiling of the sequence of a target nucleic acid by use of a computer model or algorithm that classifies the target nucleic acid based on the comparison to the reference melt curve. The computer model algorithm can be a machine learning algorithm for automated melt curve classification. In some embodiments, the machine learning classification algorithm can use a Naive Bayes classifier. In some embodiments, the analysis device processor can be configure to profile the sequence of a target nucleic acid is performed using a Support Vector Machine (SVM). The analysis device processor can be configured to compare the melt curve for the amplicon to a plurality of melt curves from different nucleic acid sequences to profile the sequence of a target nucleic acid. The analysis device processor can be configured to exclude melt curves below a threshold melt temperature to profile the sequence of a target nucleic acid. In some embodiments, exclusion of melt curves below a threshold melt temperature can improve type I and II errors by correcting for short non-specific amplification products that melt at a lower temperature than the target amplicon. The analysis device processor can be configured to compare melt curve shape or melting temperature ($T_m$) of the amplicon.

In addition to standard chip formats (e.g., dPCR chip platforms described above), droplet-based systems, e.g., droplet high resolution melt platforms (ddPCR platforms), may be utilized to allow for continuous analysis of 1,000,000 or more droplets or reactions. The imaging components used in the droplet based systems can be the same as those described above for the dPCR chip platforms. For heating, droplet based systems can utilize PID controlled stable temperature gradients. The heating rate can be controlled by flow speed of droplets and steepness of the temperature gradient, which allows for varying the heating rate. The flow rate can determine how many droplets are analyzed per second. Since the droplet system can be operated continuously, the number of reactions analyzed is limited only by the number of droplets that are made. Droplet generation could be made to run continuously as well and a PCR cycling region could be added to the heating apparatus and fluidic chip to make a completely continuous system from sample prep, droplet making, thermal cycling for amplification, and HRM melting for sequence identification.

The systems and devices described herein can be used in the methods and assays described herein. In one aspect, a method of profiling the sequence of a target nucleic acid in a sample is provided, the method including combining a sample including a target nucleic acid with one or more universal amplification primers, one or more DNA intercalating dyes, and reagents for amplifying a target nucleic acid to form a reaction mixture; partitioning the reaction mixture into 10,000 or greater partitions; amplifying the target nucleic acid sequence to produce an amplicon; performing melt analysis of the amplicon by simultaneously heating and imaging the partitions, whereby a melt curve for the amplicon is produced; and profiling the sequence of the target nucleic acid by comparing the melt curve for the amplicon to a melt curve from different nucleic acid sequences.

In some embodiments, the method can include controlling a temperature difference between any two points on the chip or platform during heating to 0.6° C. or less when performing melt analysis of the amplicon. In some embodiments, differences in the high temperature calibrator melt temperature on the chip or platform vary from 0.22° C. to 0.6° C., after excluding the outliers due to evaporation at the corners and edges of the chips or platforms. In some embodiments, with evaporation outliers included, median absolute deviation ranging from 0.05° C. to 0.1° C. and standard deviation of 0.06° C. to 0.13° C. occur across the chip or platform. As compared to conventional PCR, the smaller reaction volumes of dPCR could, in some embodiments, lead to larger variations in melt temperature ($T_m$) due to evaporation. However, in some embodiments, the small form factor of the digital chip or platform may maintain a more uniform thermal gradient across the chip or platform, leading to smaller variations in $T_m$. A previously published study reported $T_m$ differences ranging from 0.35° C. to 1.24° C. across 32-96 well plate melt instruments with standard deviations of 0.018° C. to 0.274° C.[44] Performance could be improved by optimizing for loading errors and evaporation. For example, the application of oil onto the loaded reaction wells could be sensitive to timing and amount deposited, and automation would ensure that the corner wells are covered as quickly as the central wells to minimize evaporation.

In some embodiments, the heating of the dPCR chip or ddPCR platform is performed at a heating rate of from about 0.002° C./s to about 1° C./s or from about 0.005° C./s to about 0.5° C./s. The melt analysis of the amplicon can be performed by simultaneously heating and imaging the digital PCR chip or ddPCR platform is performed at a rate that is synchronized with the heating rate. For example, heating of the conductive block can be independently controlled by standalone software, while the proxy temperature measurement from the surrogate chip or platform can be synchronized with fluorescent imaging by the microscope control software (e.g., NIS-Elements). Synchronizing imaging with temperature measurement can be accomplished with, for example, the use of an MS-Elements compatible temperature acquisition system (Tokai Hit Co., Japan) using a K-type thermocouple probe. However, in some instances, such acquisition systems only provide limited resolution of temperature measurement to 0.1° C. with a temperature sampling rate of ~0.2 Hz irrespective of the imaging rate. To compensate, the conductive block temperature can be precisely controlled, a repeatable relationship between the conductive block-embedded RTD and the surrogate chip-embedded or platform-embedded thermocouple established, and integrated thermocouple temperature data and fluorescence imaging data can be used to plot melting curves.

In some embodiments, the methods can further include performing automated melt curve classification with an analysis device having a processor configured to perform machine learning. The melt analysis of the amplicon can be performed, in some embodiments, by simultaneously heating and imaging the partitions to produce a melt curve for the amplicon. The method can include profiling the sequence of the target nucleic acid by comparing the melt curve for the amplicon to a plurality of melt curves from different nucleic acid sequences. The plurality of melt curves can include at least one reference melt curve from a known nucleic acid sequence. The method can include automated profiling of the sequence of a target nucleic acid by use of a computer model or algorithm that classifies the target nucleic acid based on the comparison to the reference melt curve. The computer model algorithm can be a machine learning algorithm for automated melt curve classification. In some embodiments, the machine learning classification algorithm can use a Naive Bayes classifier. In some embodiments, the method can include profiling the sequence of a target nucleic acid by using a Support Vector Machine (SVM). The method can include comparing the melt curve for the amplicon to a plurality of melt curves from different nucleic acid sequences to profile the sequence of a target nucleic acid. In some embodiments, the method can involve excluding melt curves below a threshold melt temperature to profile the sequence of a target nucleic acid. The method can include comparing melt curve shape or $T_m$ of the amplicon. Probability based classification models useful in the methods and systems described herein include Gaussian Naïve Bayes (NB), multinomial Logistic regression (LR), and Multi-layer Perceptron (MLP) approaches for probabilistic classification. NB allows for incorporation of prior knowledge into the prediction model. For example, in some embodiments, epidemiological prevalence can be added as prior probabilities to provide added robustness of identification. Some embodiments can use equal priors, i.e. equiprobable organism classes.

In some embodiments, the algorithm can apply OVO SVM to match a test melt curve to a melt curve contained in a pre-defined database. In some embodiments, a pre-defined database can include melt curves of one or more typical-pathogens, such as, for example, neonatal pathogens. In some embodiments, a melt curve anomaly detection algorithm using probabilistic classification is employed. Thus, training melt curves for each organism class can be used to build statistical models for those classes. Then the probability of a test curve belonging to each class can be calculated and this can be used as a measure for outlier detection. This approach is uniquely made possible by the novel high-throughput dHRM format described herein, where thousands of training curves are generated per run to robustly model each organism class.

Classification can, in some embodiments, be accomplished by combining the NB model with a decision rule to choose the most probable class as the label for a test curve using the maximum a posteriori (MAP) rule. In some embodiments, LR can be used to model the training data and compare classification performance to that of NB. LR model coefficients can be initially estimated using a squared regularizing function and then solved using maximum likelihood estimation. Goodness of fit can be measured by calculating the deviance of the model. In some embodiments, a non-linear MLP model can be constructed using the same training data and can have multiple layers of neurons that each use a non-linear logistic activation function. Back propagation can be used for training and can minimize the cross-entropy loss function to generate probability estimates for whether a test curve belongs to each organism class. The classification accuracy of each approach described above can be optimized with parameter tuning and tested using LOO, k-fold, and bootstrap cross validation on a given database of organisms. The best performer can be used to explore anomaly detection methods, such as for detecting unknown pathogens. In some anomaly detection embodiments, the Shannon entropy (SE) approach can be applied. The SE is a measure of the uncertainty in the posterior probabilities of a test curve, which can be calculated using the best performing probabilistic classification model described above. Higher magnitudes of SE are associated with more uncertainty in the classification decision made, which enables finding empirical thresholds on the entropy to minimize erroneous classifications. In some embodiments, this can enable the algorithm to abstain from making a decision for a classification with high associated entropy and instead provide information about how close to the current classes of pathogen that the curve is. At the same time, the SE can be used to generate a confidence score for all test curves, thus providing a more informative diagnostic answer. The databases of organisms can be segmented into training organisms and mock anomaly test organisms for this purpose and again LOO, k-fold, and bootstrap cross validation can be used to determine an optimal entropy threshold giving the highest accuracy in anomaly detection. In some embodiments, greater than 99% accuracy can be achieved in the identification of non-database organisms in mock anomaly datasets.

In some embodiments, dynamic temperature warping (DTW) can be used as a method to calculate a distance-from-class measure for outlier detection. DTW is typically a measure for estimating the similarity between two temporal sequences. In some embodiments of the system, temperature sequences can replace temporal sequences. By sweeping one melt curve over the other, DTW calculates the optimal match between the sequences, by trying to explain any fluctuations in the y-axis of melt curve by warping the temperature axis. A statistical model can then be built on the DTW measure for each class to identify melt curves with DTW measures that are unlikely, according to an empirically selected threshold that minimizes Type I and II errors. In some embodiments, information theoretic techniques can be used to estimate upper bounds on the number of pathogens that can be discerned.

In some embodiments, the method can further include calculating and/or assigning a confidence score or measure to the resultant classification. Thus, confidence of the determined melt curve classification can be provided and a determination can be made whether a given melt curve classification, for example a given species identification or sub species identification, can be determined to be clinically relevant.

In some embodiments, DTW can be applied first to identify any melt curves that are highly anomalous, followed by classification using LR or Multilayer Perceptron modeled on pre-defined database, then calculation of SE as a confidence measure on the prediction. In some embodiments, uncertainty in classification can be established using the LR model. In some embodiments, the Shannon entropy can be calculated across the posterior probabilities. Misclassified melt curves have a higher entropy in comparison to the correctly classified melt curves. Thus Shannon entropy measurement of the posterior probability can be used along with the prediction class as a measure of confidence of the classification.

In some embodiments, the method can further include subjecting the sample to a first heating rate to obtain a first melt curve signature; subjecting the sample to a second heating rate to obtain a second melt curve signature; and performing a heating rate-dependent melt curve analysis using a computer model or algorithm that classifies the target nucleic acid based on the comparison to the reference melt curve, such as by using a machine learning algorithm for automated melt curve classification. In some embodiments, subjecting the sample to a first heating rate and a second heating rate includes cooling the sample and re-melting the same sample. The number of re-melt cycles that can be performed can include, e.g., at least one re-melt cycle, at least two re-melt cycles, at least five re-melt cycles, ten or fewer re-melt cylces, five or fewer re-melt cycles, or two or fewer re-melt cycles. In some instances, the number of re-melt cycles that can be performed may be limited by photobleaching effects. In some embodiments, subjecting the sample to a first heating rate and a second heating rate includes subjecting a first portion of the sample to a first heating rate to obtain a first melt curve signature, and subjecting a second portion of the sample to a second heating rate to obtain a second melt curve signature. It has surprisingly been discovered that some nucleic acid molecules exhibit heating rate-dependent melt profiles and that the rate-dependent melt profiles can be used for more precise target identification. It was previously generally thought that heating rate changes only result in shifts in melt curve $T_m$, whereas the dynamic melting characteristics of a PCR product are thought to be primarily determined by GC content, sequence length, and nucleotide order.[44,45] However, the inventors have discovered that some long amplicons are highly sensitive to melting ramp rate, which not only shifts their $T_m$, but also changes the number and size of distinct melting transitions present. The ability of the methods and systems described herein to identify a heating rate dependence of melt curve shape is in large part due to the tunability, uniformity, and throughput of the digital melt platform. For the long amplicon sequences studied, slower heating rates resulted generally in a single melt transition, whereas faster rates generated multiple melting domains. The inventors have surprisingly discovered that this response to heating rate is highly sequence dependent. Some long amplicon sequences maintained the same melt curve shape for multiple heating rates, while others do not. Thus, the response of a long amplicon to heating rate changes provides additional sequence-specific information that could enhance the specificity of melt curve-based sequence profiling. That is, where one ramp rate cannot discriminate two sequences by their melt curve, a combination of multiple ramp rates may reveal distinct melt responses. Without wishing to be bound by theory, it is believed that the mechanism underlying these differences may involve kinetic sampling of transition states. For example, slower rates would be expected to enable amplicons to sample a wider range of transition states, where shifting, re-organized binding, or secondary structure formation could effectively average out the fluorescence decay across the bulk population of amplicons. Faster rates may induce more uniform transition behavior involving abrupt local DNA "bubbles" that melt separately at a different temperature than the remainder of the sequence. Indeed, faster rates of melting have previously been associated with higher $T_m$ accuracy in homozygous melt analysis.[34] Alternatively, since heteroduplex melting has been found to be more apparent at faster heating rates, the multiple melt domains we observe at faster ramp rates may be the result of distinct heteroduplex binding transition states induced in homoduplex molecules.[34]

In some embodiments, the methods described herein may further include identifying a pathogen or pathogen marker present in the sample. As used herein, a pathogen marker can include a nucleic acid molecule or sequence derived from a living or recently deceased pathogen present in a sample. In some embodiments, the methods described herein may further include identifying a pathogen or pathogen marker present in the sample, wherein the pathogen or pathogen marker has a known nucleic acid melt-curve signature. For example, the melt curve signature obtained from processing the sample containing the pathogen or pathogen marker according to the methods described herein can match one or more reference melt curve signatures in a classification database. In some embodiments, the methods can further include identifying a pathogen or pathogen marker present in the sample, wherein the pathogen or pathogen marker has an unknown nucleic acid melt-curve signature. For example, the melt curve signature obtained from processing the sample containing the pathogen or pathogen marker according to the methods described herein may not match one or more reference melt curve signatures in a classification database. In such case, the machine learning algorithm can identify a pathogen based on anomaly detection. In some embodiments of the methods, identifying a pathogen or pathogen marker present in the sample has an error rate of less than 0.2%.

In another aspect, a method of treating a patient suspected of having sepsis, such as, for example, neonatal sepsis is provided. The method includes identifying one or more pathogens having a high probability of mediating the patient's sepsis by performing melt curve analysis by any of the methods described herein, and administering to the patient one or more antimicrobials effective against the one or more identified pathogens. For example, up to one million or more reactions, on either droplet-based or chip-based platforms can be used for single pathogen detection. The methods described herein provide rapid identification of pathogens, which can provide life-saving improvements in the timing and accuracy of treatment regimens. Further, these techniques can extend to other applications in agriculture, defense, and environmental monitoring of organisms.

EXAMPLES

The invention is further described in the following examples, which do not limit the scope of the invention described in the claims.

Example 1

Digital HRM Device Concept

Figure 1C:
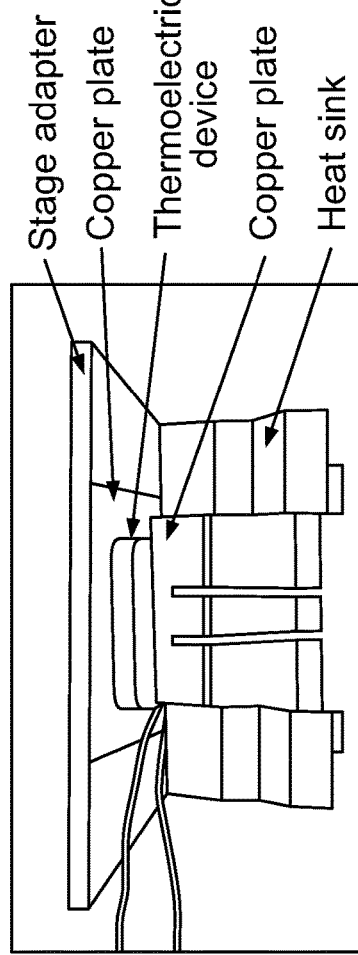
Figure 1D:
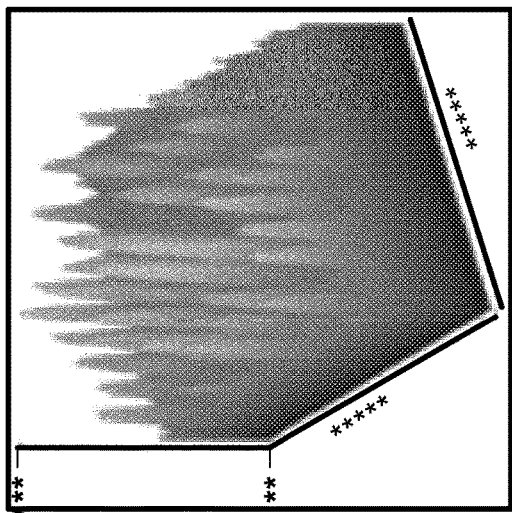

The inventors developed a proof-of-concept U-dHRM platform for the clinical application of neonatal bacteremia diagnosis. Clinically relevant bacterial loads are estimated from culture techniques to be between 1 to ~2,000 colony forming units (cfu) per blood sample (1 ml), where 76% of samples have <50 cfu[30,31]. This load requires 20,000 reactions to provide a dynamic range of detection up to 1,810 bacterial genomic DNA molecules at the single molecule level (FIG. 1(A), right). A digitizing chip fitting this scale of reactions is commercially produced for traditional endpoint dPCR applications (see Methods), and was chosen as a robust and reliable digitizing device. To identify digitized bacterial DNA, universal primers targeting the 16S rRNA gene were used. The 16S harbors conserved sequence regions flanking hypervariable regions that are unique to different genus and species of bacteria[32]. Primers targeting conserved regions generate bacteria-specific amplicons for U-dHRM profiling. Specifically, the inventors' long amplicon (~1,000 bp) 16S bulk universal FIRM assay[24] was adapted (see Methods) to enable successful digital amplification and reliable U-dHRM in each of the 725 picoliter volume reactions on-chip, a 99.995% volume reduction compared to the typical FIRM reaction format. To enable massively parallel U-dHRM across the 20,000 reactions, the inventors developed a custom high resolution heating device and imaging system. A schematic of the inventors' design is shown in FIG. 1(B). Precise chip heating was accomplished using a thermoelectric heater/cooler with Arduino controller, power supply, and heat sink. A copper plate was attached between the thermoelectric device and the dPCR chip and between the heat sink and the thermoelectric device to evenly distribute heat. A custom adapter was designed to secure the chip-heating setup onto an automated x,y stage for rapid imaging of the 20,000 reactions as four tiled images at each temperature point during the U-dHRM heat ramp. FIG. 1(C) shows an image of the integrated heating device and stage adapter. The imaging system was equipped with a 4× objective as well as red and green LED-based fluorescence channels. An image analysis program was developed to align reaction well centroids and overcome image drift during heat ramping as well as extract raw fluorescence data from each reaction simultaneously (FIG. 1(D)). A previously developed OVO SVM algorithm was adapted to classify and quantify U-dHRM curves after being trained on melt curves generated on-chip. The digital chip, chip heating device, fluorescent imaging system, control electronics, and analysis algorithms for image processing and melt curve identification were integrated to enable massively parallel U-dHRM and absolutely quantitative bacterial profiling.

System Characterization & Optimization

Figure 2A:
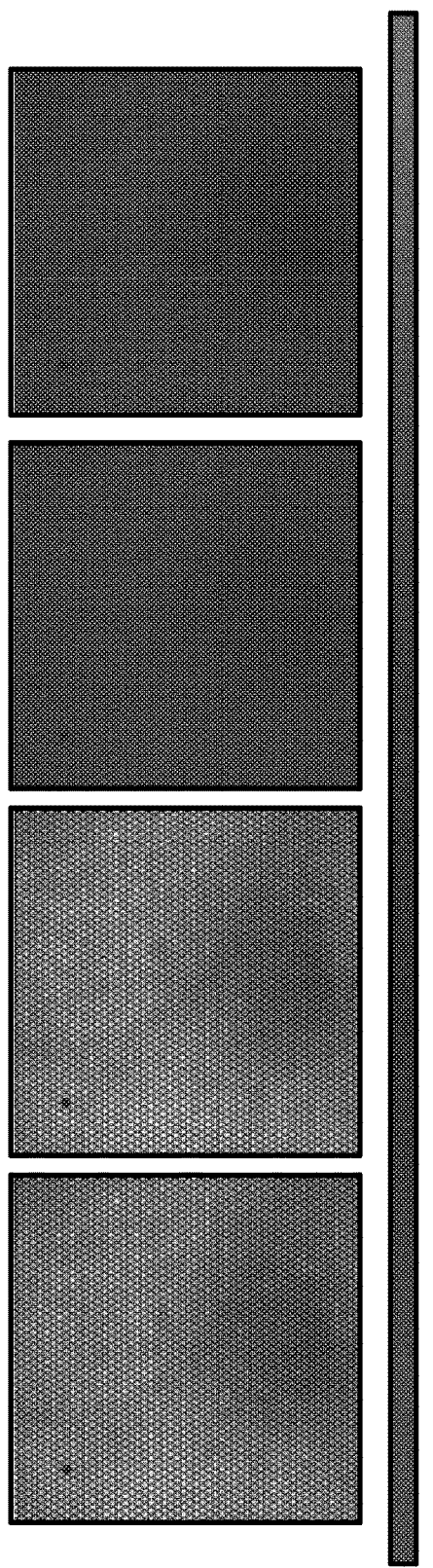
Figure 2B:
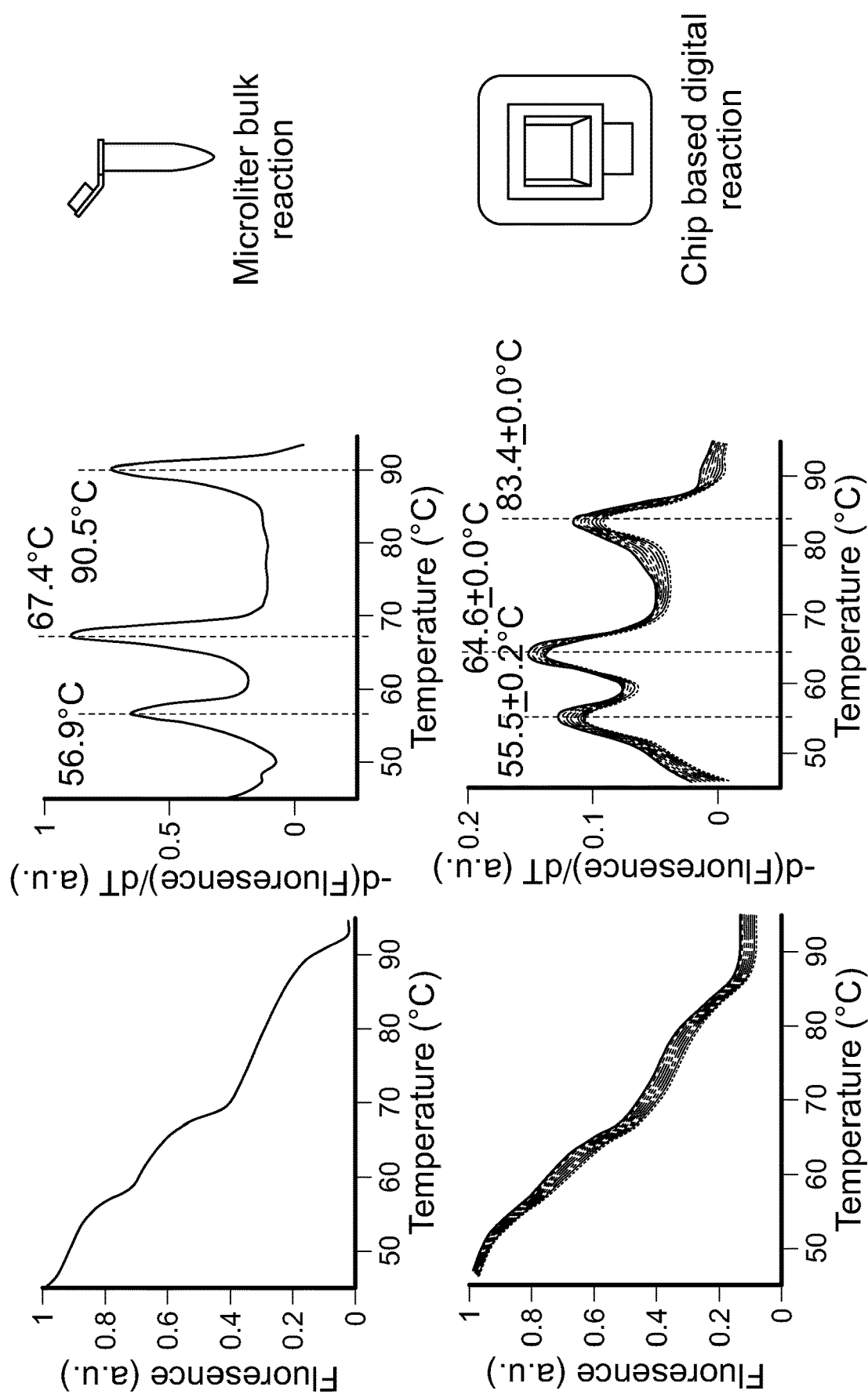
Figure 2C:
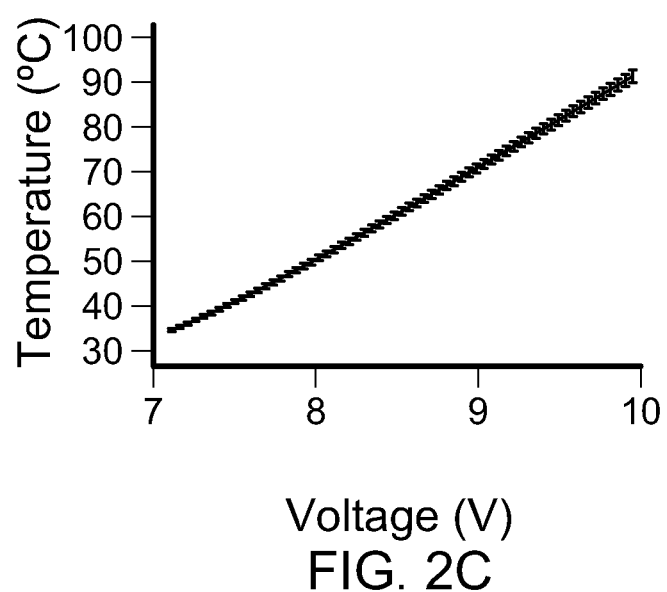

The challenge of generating high quality U-dHRM curves in picoliter-scale reactions was first approached by tuning fluorescent intercalating dye concentrations to maximize signal-to-noise ratio. An EvaGreen dye concentration of 2.5× was found to be the highest concentration that did not inhibit amplification on-chip. Next, the simultaneous imaging and heating process of melt curve generation (FIG. 2A) was tuned using three synthetic DNA sequences containing 0% GC, 12% GC, and 76% GC with different predicted melting temperatures (Tms) (FIG. 2B). The greater the GC content, the higher the temperature required to melt the DNA due to higher bond strength. After loading mixtures of these three sequences onto a chip, we performed preliminary calibrations of the inventors' device, optimizing imaging exposure time to minimize photobleaching while maintaining the highest possible signal-to-noise ratio. We also used these initial readings to develop our image analysis algorithm (see Methods). FIG. 2B shows the normalized fluorescence versus temperature and derivative melt plots for the three calibrator sequences in traditional qPCR HRM and U-dHRM formats. The temperature calibrators are predicted to melt at 57.3° C., 62.8° C., and 92.9° C. by melt curve prediction software, uMELT[10]. The average Tms given by qPCR HRM were 56.9° C., 67.4° C., and 90.5° C. respectively, while U-dHRM Tms were 55.5° C., 64.6° C., and 83.4° C. These readings indicated that further temperature ramp optimization was necessary. Improved temperature resolution was achieved by varying the heating ramp rate until a linear and repeatable relationship between voltage and temperature could be maintained throughout our temperature range of interest, 45-95° C. For highest accuracy, temperature was monitored during the ramp by placing a thermocouple inside a surrogate oil-filled chip and placing this chip next to the calibrator loaded chip. A ramp rate of 0.02° C./sec was found to give optimal linearity and repeatability of the voltage and temperature relationship, with maximum standard deviation of 1.22° C. occurring at a temperature of −91.6° C. over 5 runs (FIG. 2C).

Figure 3A:
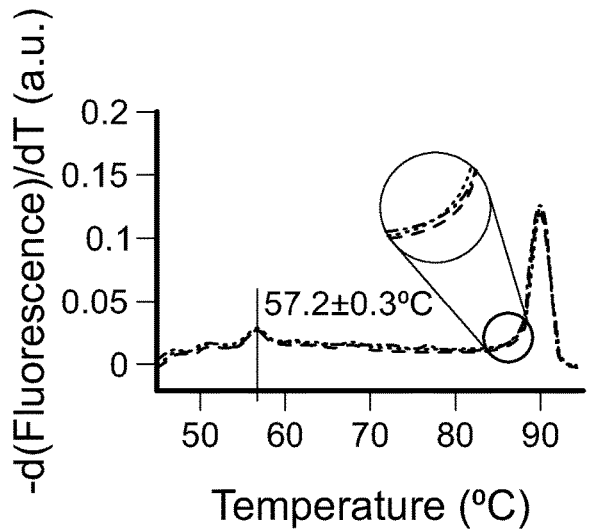
Figure 3B:
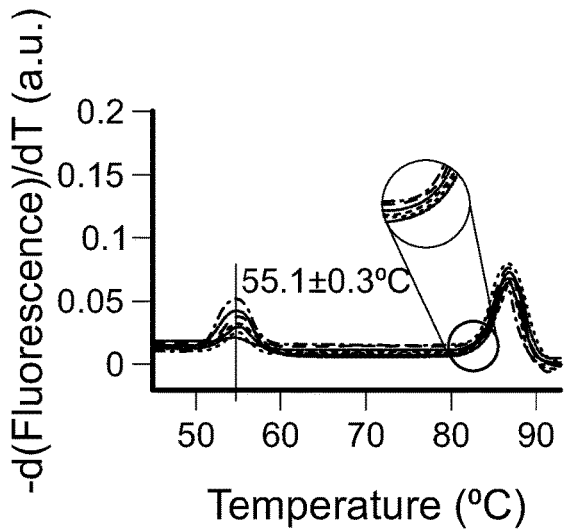
Figure 3C:
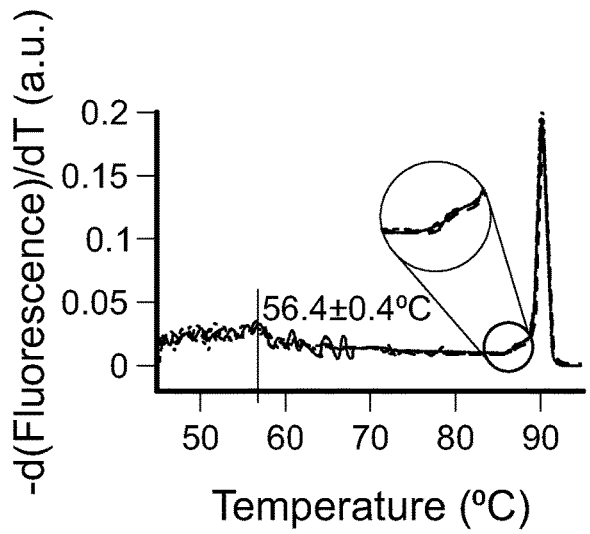
Figure 3D:
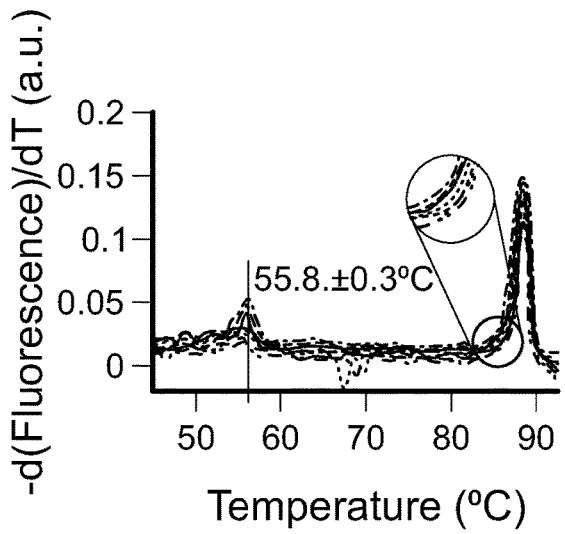
Figure 4A:
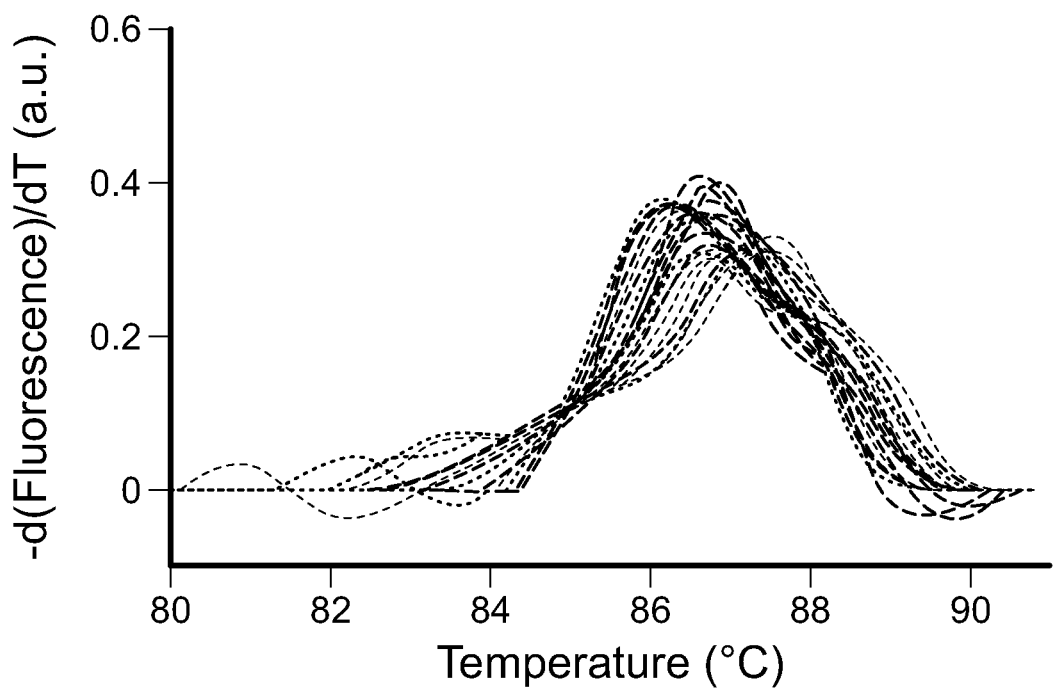
Figure 4A:
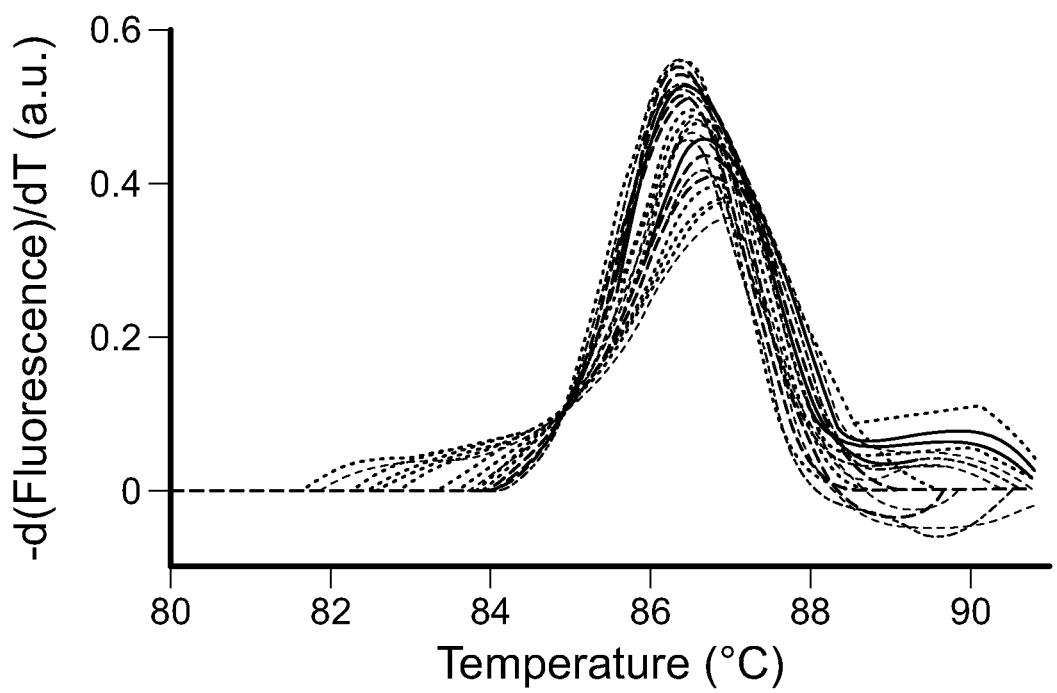

Next, bacterial DNA from clinical isolates of *Listeria monocytogenes* and *Streptococcus pneumoniae*, two common pathogens causing neonatal bacteremia[33], were used to further optimize signal-to-noise ratio and melt curve shape resolution (i.e. temperature resolution). First, HRM optimization was carried out on a standard qPCR HRM machine. In this format, melt curve shape, a key discriminating feature of bacterial 16S melt curves[24], was found to be highly dependent on imaging rate. A low imaging rate of 1 image per 0.3° C. smoothed melt curve shape features (FIG. 3A, circle), but a faster imaging rate of 1 image per 0.1° C. captured small shape differences known to be identifiable by our machine learning algorithm[24] (FIG. 3C, circle). Using the optimized chip heating ramp rate described above, we next optimized imaging rate on the standard qPCR FIRM machine and validated these settings on our U-dHRM system (FIGS. 3, B and D). The low calibrator sequence (first peak from left in FIG. 3 melt curves) was included in all amplification reactions to align curves and overcome temperature variation across reaction wells. First, the chip imaging rate was adjusted to replicate the default qPCR machine of 1 image taken every 0.3° C. Imaging the chip every 15 seconds at the optimal heat ramping rate of 0.02° C./sec on our U-dHRM platform allowed us to achieve this rate. Melt curves generated from these settings constitute the low imaging rate data in FIG. 3B. With these settings, the average peak-to-baseline ratio of the 16S amplicon derivative melt curves (after min-max normalization of raw melt data) was 0.1096±0.0024 on the qPCR HRM machine versus 0.0660±0.0034 for U-dHRM. We then increased the imaging rate on our U-dHRM system to image every 5 seconds, matching the high imaging rate of 1 image per 0.1° C. on the qPCR HRM machine (FIG. 3D). At the high imaging rate, the average peak-to-baseline ratio of the 16S amplicon derivative melt curves was 0.1759±0.0073 on the qPCR machine versus 0.1225±0.0066 for U-dHRM, demonstrating that our device achieves comparable signal-to-noise performance. Small shape differences in melt curves were also identifiable on-chip but to a lesser degree than in the standard qPCR HRM machine (FIG. 3A-D, circles). However, higher background noise on-chip caused this detail to occasionally be lost during curve processing and normalization (FIG. 4A, bottom). $T_m$ reproducibility was almost identical between the two optimized platforms, as demonstrated by the $T_m$ standard deviation of the temperature calibrator sequence (~0.3° C., FIG. 3). Because this deviation still existed under optimized conditions, temperature calibrator sequences were included in all reactions for aligning melt curves prior to further analysis.

TABLE 1

Comparison of Genomic DNA Quantification Techniques

| Bacteria | Method of Quantification | Number of Genomes/μL |
|---|---|---|
| S. pneumoniae | Absorbance | 5780 |
| | qPCR | 6554 |
| | U-dHRM total | 5460 |
| | bacterial melt curves | 1200 |
| | non-template melt curves | 4260 |
| L. monocytogenes | Absorbance | 9160 |
| | qPCR | 10839 |
| | U-dHRM total | 7580 |
| | bacterial melt curves | 2260 |
| | non-template melt curves | 5320 |

Table 1. Comparison of Genomic DNA Quantification Techniques. The concentration of genomic DNA isolated from both S. pneumoniae and L. monocytogenes was measured using an Eppendorf Biospectrometer, by qPCR standard curve method, and using U-dHRM. Total U-dHRM values are the sum of reactions identified as having specific amplification of bacterial DNA plus the reactions having off-target amplification. Reactions having no amplification, i.e. no melt curve, were classified as true negatives and make up the remainder of the 20,000 total reactions per U-dHRM chip (not represented in this table). QPCR standard curves are shown in Suppl. FIG. 2. Absorbance measurements were made on stock DNA, then the DNA was serially diluted. The calculated concentration of the dilution used on chip is reported here for each measurement modality.

We then integrated our automated OVO SVM melt curve identification approach with our U-dHRM platform to enable automated identification of bacteria based on their melt curve signatures. A training database of bacterial melt curves was generated on-chip to enable automatic melt curve identification. Bacterial DNA from L. monocytogenes and S. pneumoniae were loaded onto separate chips in excess, □ of 223 and 141, respectively, as calculated from spectrometer readings. This ensured each of the 20,000 reactions would be positive for amplification and would generate a training melt curve for the bacterial isolate. Each sample underwent U-dHRM using the optimized ramp and imaging rates described above. FIG. 4A shows the U-dHRM training curves generated on-chip for S. pneumoniae and L. monocytogenes after processing with our image analysis, normalization, and alignment algorithms (see Methods). The processed curves were entered into our OVO SVM algorithm as training data (see Methods). Leave One Out Cross Validation (LOOCV) reached a maximum classification accuracy of 99.9% within the training dataset with 1,500 training curves.

Absolute Quantification of Bacterial DNA

Figure 4B:
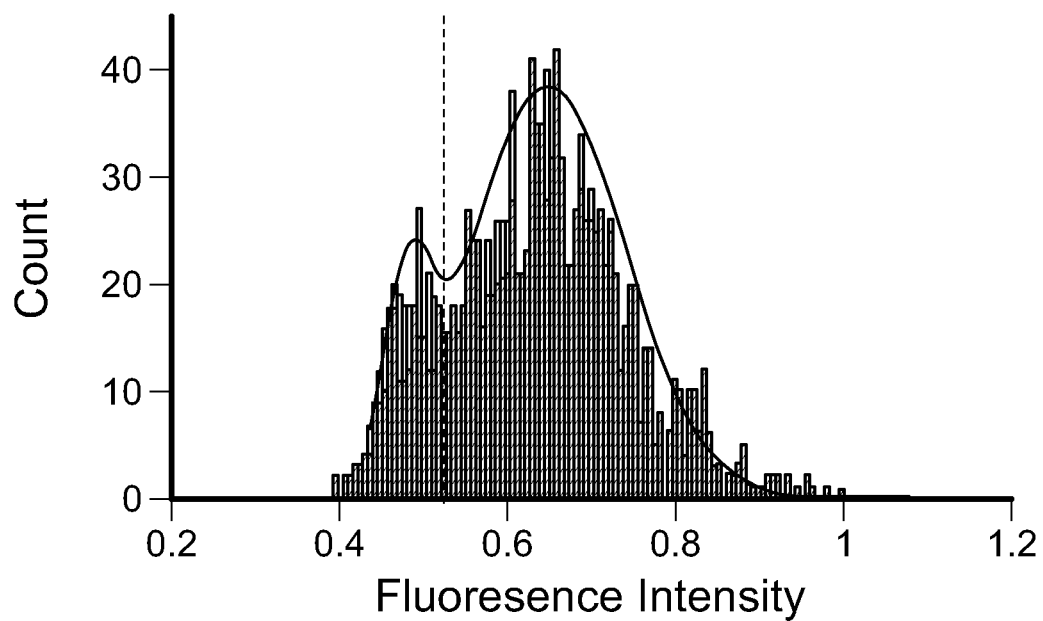
Figure 4B:
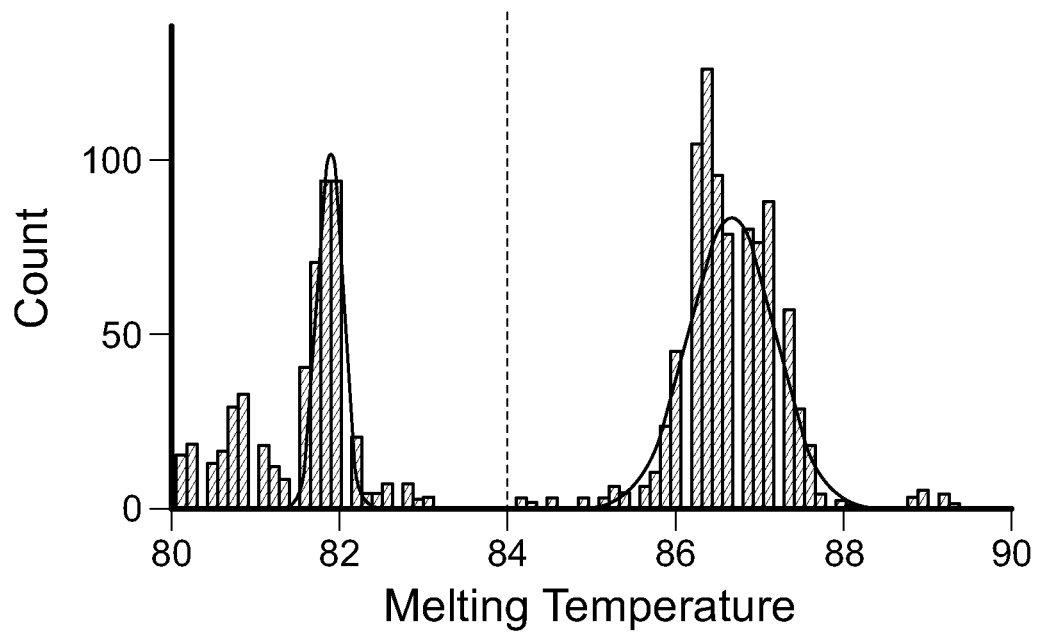
Figure 4C:
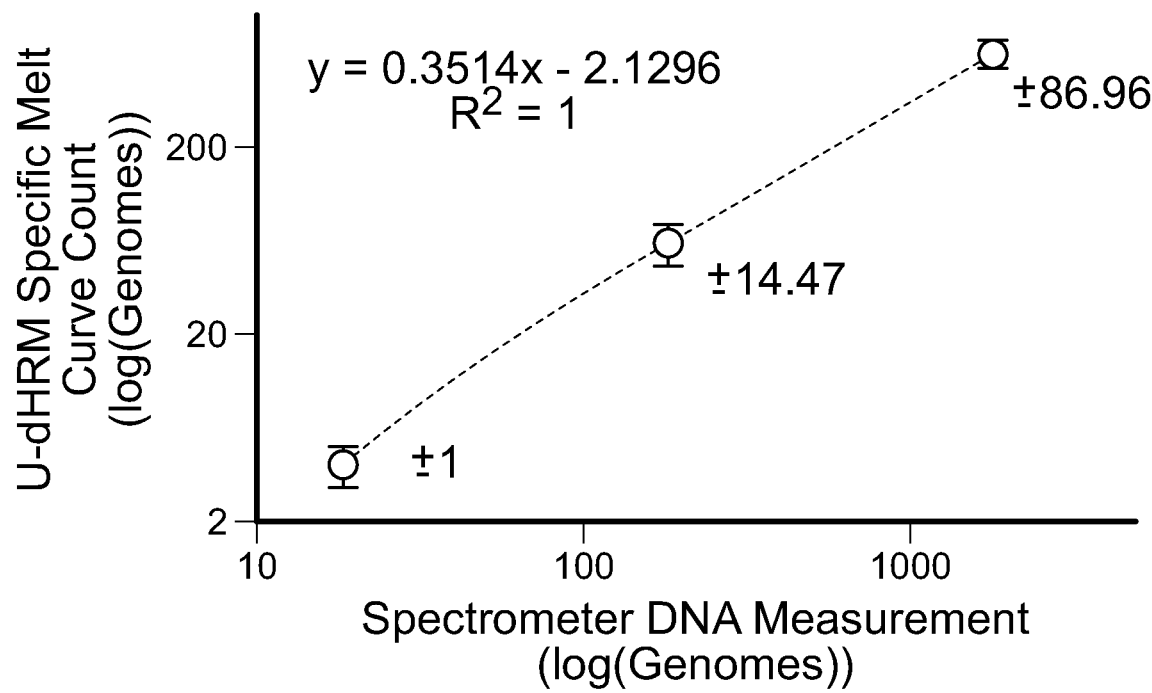
Figure 6A:
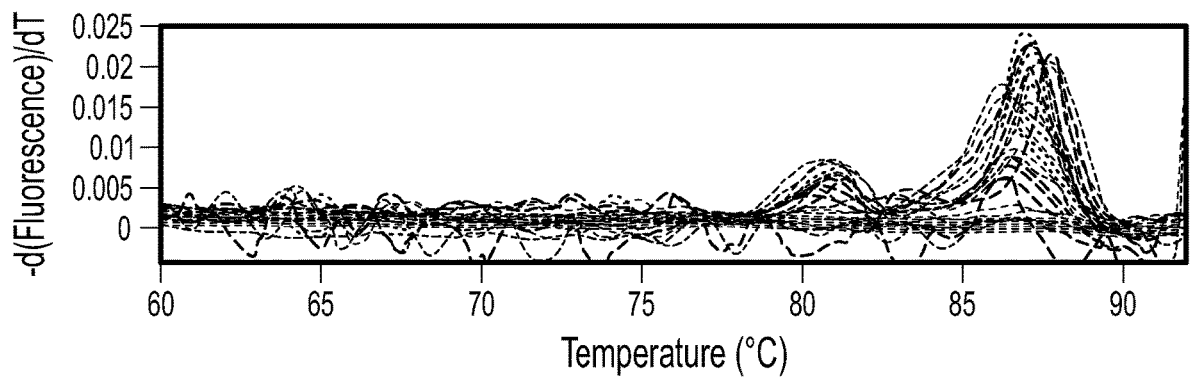
Figure 6B:
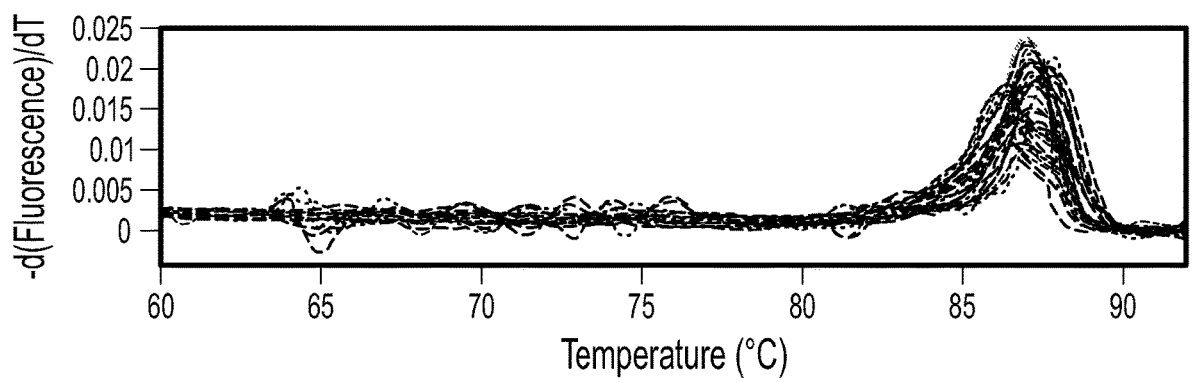
Figure 6C:
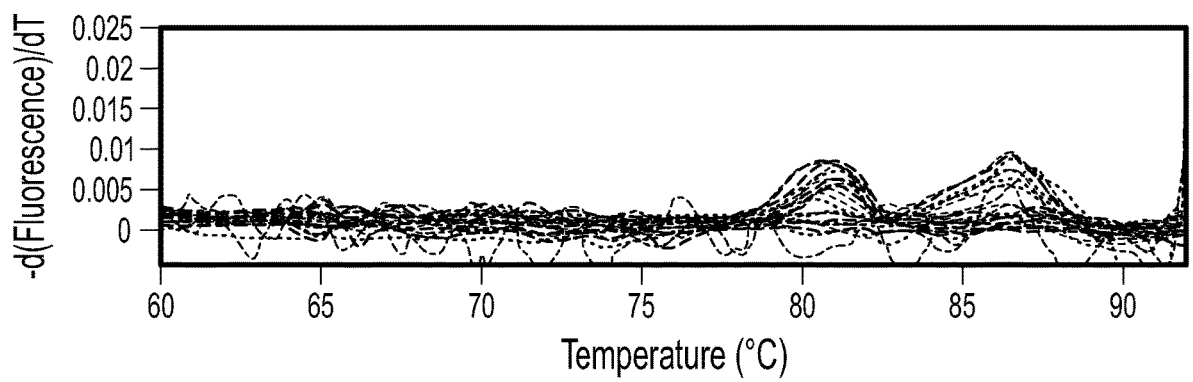

Digital quantitative power relies on the ability to specifically identify true positive amplification from non-specific background amplification. To assess the absolute quantitative power of our platform, we compared U-dHRM melt curve quantification to intercalating dye-based endpoint dPCR quantification. A chip was loaded with a monomicrobial DNA sample of L. monocytogenes according to the concentrations described in the lower panel of Table 1 and U-dHRM was conducted. Then, true positive amplification was quantified two ways. For the first quantification method, we followed the typical endpoint PCR enumeration approach (top graph in FIG. 4B), which is based on measuring the fluorescence of all wells at room temperature, fitting the distribution of well fluorescence values to a probability density function (PDF), and applying a fluorescence threshold that best separates the high intensity population (positive) from the low intensity population (negative). For the second method, we used our U-dHRM melt curve readout to identify the number of digital reactions having specific bacterial melt curves. The Tm for a bacterial amplicon, 1,000 bp long, was expected to be centered at 86.5° C., based on data collected from the overloaded training chips (FIG. 4A). To automate identification of reactions that specifically generated bacterial melt curves, we fit a PDF to the distribution of individual reaction Tm values and applied a fluorescence threshold that best separated the high Tm population (positive, specific amplification) from the low Tm population (non-specific or negative for amplification), shown in the bottom graph of FIG. 4B. This novel analysis is uniquely enabled by our platform. The melt curves identified as positive or negative by this method are shown in FIGS. 6 (a) and (b), respectively. A no template control (NTC) sample was also run on a separate chip to characterize the Tm of non-specific amplification products. The Tm of the NTC chip reactions were significantly lower than the Tm of the 1,000 bp amplicon (FIG. 6). Comparable NTC reactions carried out in a qPCR format generated a non-sense amplicon that is 200 bp or less (data not shown). This amplicon size difference is likely the reason for the significant difference in melt curve Tm between the NTC and true positive reactions. The results of the typical dPCR enumeration method and our novel melt curve enumeration method were then compared by direct visual observation (manual analysis) of the reactions. Visual melt curve observation is used frequently after qPCR to determine whether an amplification reaction was specific or non-specific. This analysis showed that the dPCR enumeration approach gave a Type I (false positive identification of reactions having non-specific melt curves) error rate of 22.6% and Type II (false negative identification of reactions having bacteria-specific melt curves) error rate of 1.19% (average across 3 chips), resulting in a lower limit of detection of ~238 genomes per chip. Our automated melt curve enumeration method based on Tm gave Type I and II error rates of 0.07% and 0.00%, respectively (average across 3 chips) compared to manual analysis, which enables a single copy detection limit. This suggests that our platform could enable general intercalating dye-based dPCR quantification to perform more reliably, even for difficult-to-optimize or partially inhibited reactions that can occur with clinical samples. We then analyzed a ten-fold dilution series of monomicrobial DNA samples of *L. monocytogenes* on-chip using the melt curve enumeration method of Tm thresholding. This showed a linear relationship across the monomicrobial DNA dilution series having an r 2 value of 1 and high measurement precision demonstrated by the low sample standard deviations at each dilution (FIG. 4C).

Figure 7A:
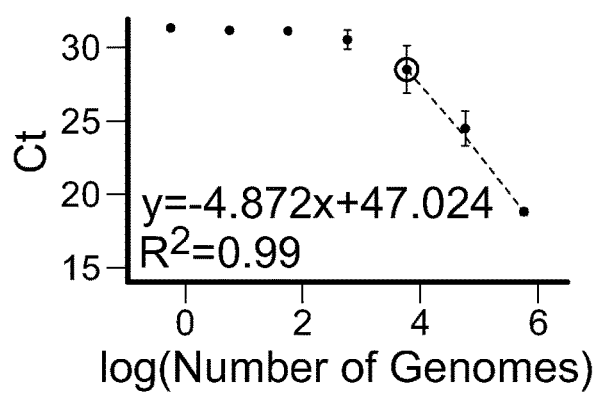
Figure 7B:
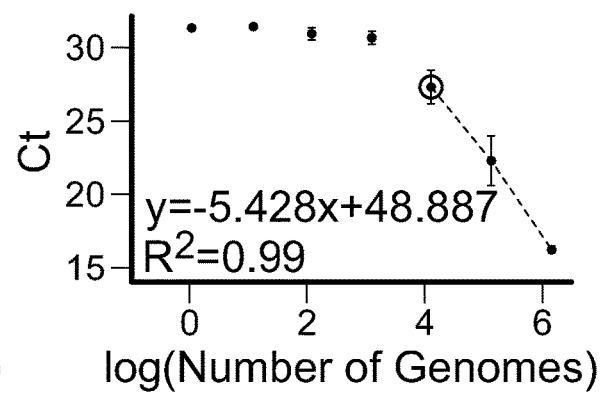

Next, we compared the number of curves quantified by our melt curve Tm enumeration method with the sample DNA concentrations calculated from spectrometer readings and qPCR standard curve methods (FIG. 7). Table 1 shows that our U-dHRM platform and melt curve enumeration method detects total DNA concentrations at similar levels as the other two technologies. However, our approach suggests that U-dHRM is able to distinguish target DNA from background amplified DNA based on melt curve $T_m$.

Identification and Quantification in Polymicrobial Samples

Figure 4D:
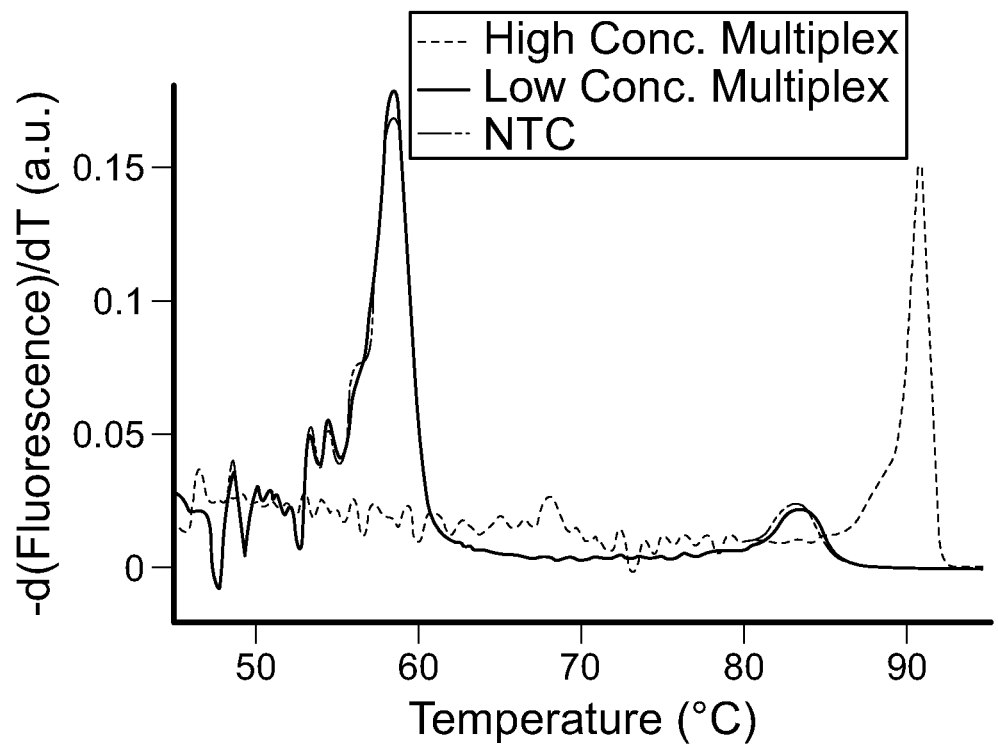
Figure 4E:
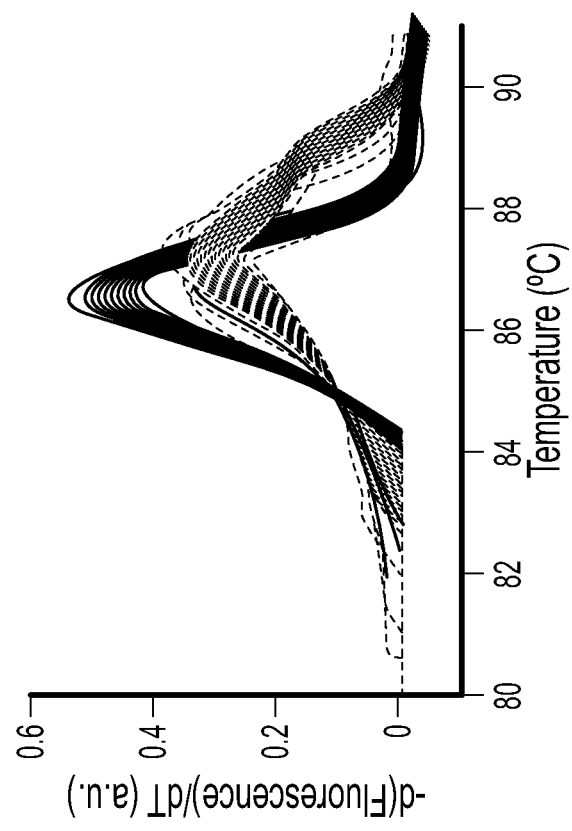
Figure 4E:
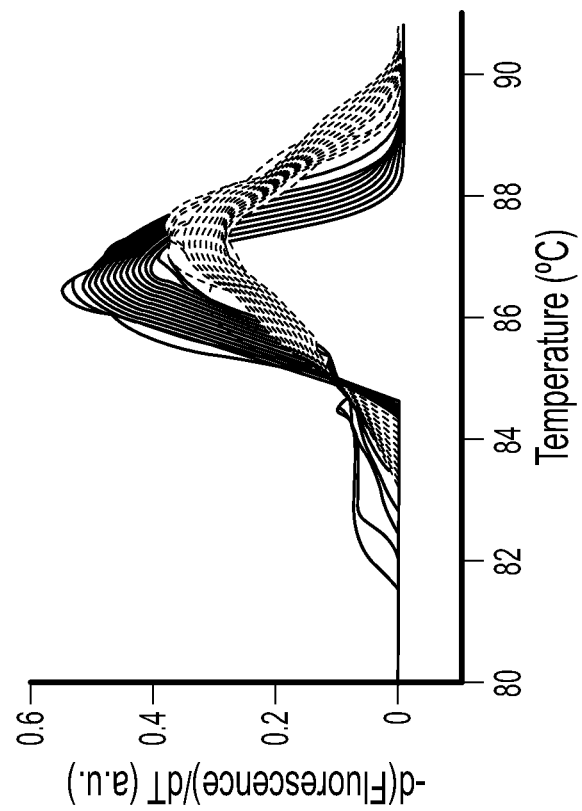

To begin to test the specificity and breadth of profiling of our U-dHRM platform, mock polymicrobial samples were generated to represent challenging detection scenarios where one organism vastly outnumbers another. Defined mixtures of *S. pneumoniae* and *L. monocytogenes* DNA were prepared at two different ratios, 1:1 and 3:1, respectively (Table 2). These mixtures were applied separately to two chips at concentrations nearing the low and high end of a typical clinical pathogen load for neonatal bacteremia (50-2,000 copies). Importantly, this dynamic range cannot be assessed by any current HRM format (FIG. 1A). The heterogeneous samples were subjected to U-dHRM followed by automated $T_m$ thresholding for true-positives and subsequent OVO SVM analysis. FIG. 4E shows the OVO SVM identified melt curves for the 1:1 and 1:3 ratios, respectively. Yellow melt curves represent those identified as *L. monocytogenes* and blue as *S. pneumoniae*. Table 2 displays the bacterial composition of the sample reported by the OVO SVM output, i.e. total number of curves classified into each bacterial identity category. The same 1:1 mixture was analyzed by qPCR HRM for comparison, (FIG. 4D). Bulk qPCR HRM fails to indicate the presence of two distinct bacterial species (blue curve) or, in cases of very low DNA input, the presence of any bacteria at all (red curve) due to overwhelming background amplification that results in a melt curve matching the NTC melt curve. This is a common problem for PCR reactions involving universal bacterial primers, since fragments of contaminating bacterial DNA are often present in reagents and liquid handling disposables[34,35]. Extensive pre-treatment of all reagents and supplies with DNase can help to improve this. However, contamination of the actual sample cannot be dealt with in the same way, and must be overcome by the detection methodology.

Detection and Quantification of Microbial DNA in Mock Clinical Samples

Figure 5A:
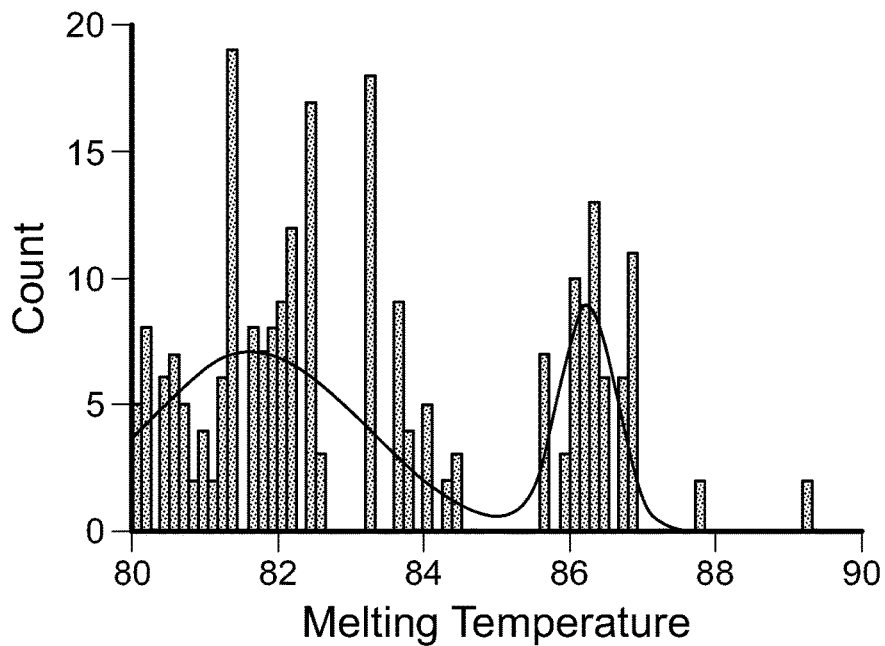
Figure 5B:
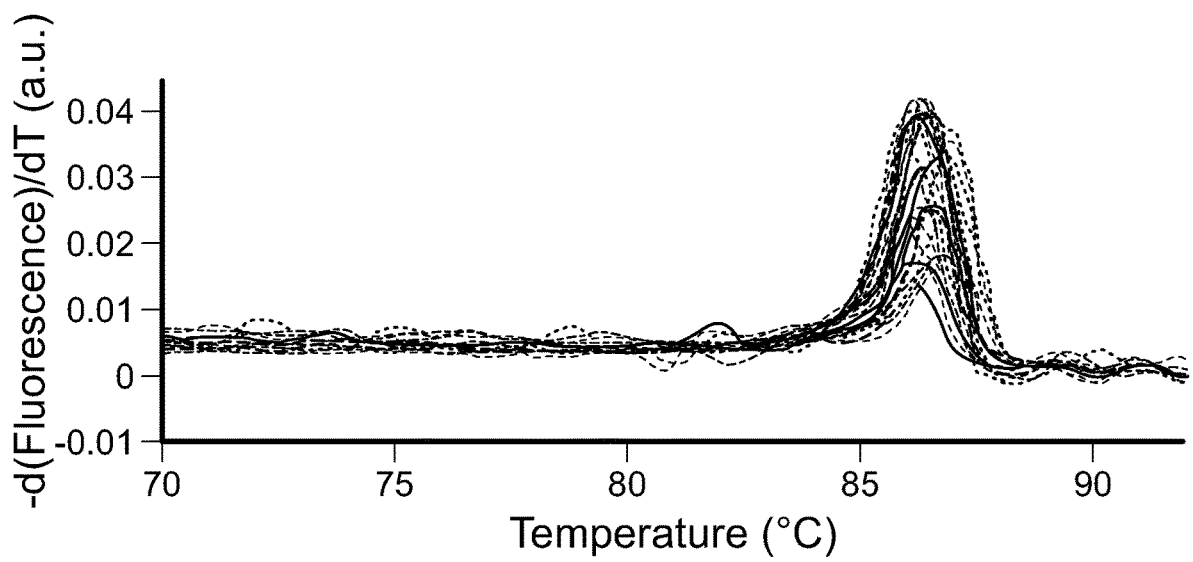
Figure 5C:
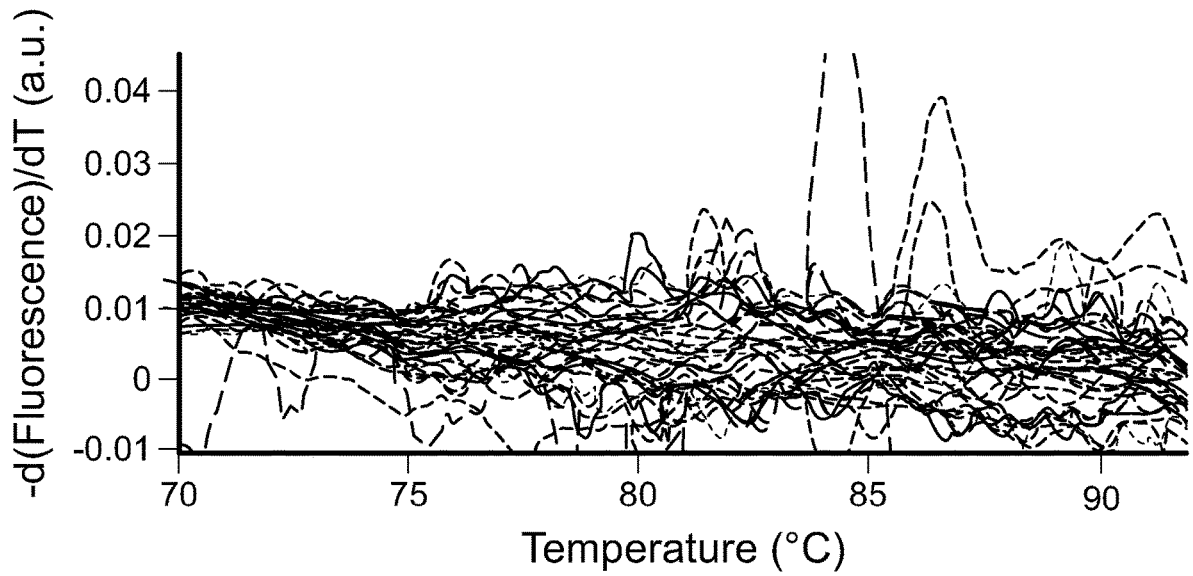
Figure 5D:
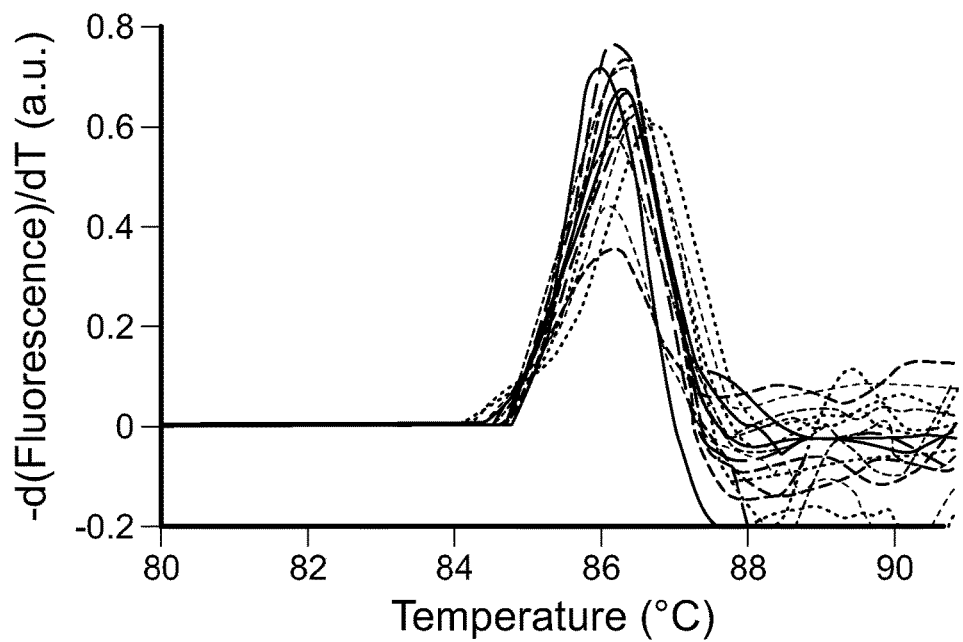

A mock experiment was conducted to test whether the large amount of human DNA associated with a clinical blood sample would inhibit U-dHRM pathogen identification. Human DNA, extracted directly from a clinical blood sample of a healthy patient, was mixed with DNA from *L. monocytogenes* in the range of a typical pathogen load (<2,000 bacterial genomes/ml blood). This mixture was loaded onto the chip and U-dHRM was performed using our integrated platform. A Tm threshold value was calculated (FIG. 5A) for separating reactions positive for bacterial amplicons (FIG. 5B) from negative reactions (FIG. 5C). This Tm threshold was higher than the one calculated previously for bacteria-only samples due to a distinct background amplification profile, presumably originating from the human DNA. Human DNA background was associated with more noise in non-specific melt curves, as shown in FIG. 5C, compared to samples that did not include human DNA (FIG. 6 (c)). This higher level of noise resulted in slight adjustments to the threshold values used to delineate background from true melt curves (FIGS. 5, B and C, also see Methods). Nonetheless, 121 *L. monocytogenes* genomes per 20,000 reactions were identified. FIG. 5D shows the bacterial melt curves identified in the mock clinical sample by our U-dHRM platform with automated analyses.

TABLE 2

Table 2. OVO SVM classification of mixed genomic DNA samples from *S. pneumoniae* and *L. monocytogenes*.

OVO SVM Classification of Mixed Genomic DNA Samples

| | | Absorbance | | U-dHRM | |
|---|---|---|---|---|---|
| Experiment | Species Mixture | Targeted Ratio of Genomes | Estimated Number of Genomes Added to Chip | Measured Number of Genomes On-Chip | Measured Ration of Genomes |
| 1 | S. pneumoniae | 1:1 | 289 | 60 | 1:1.88 |
| | L. monocytogenes | | 458 | 113 | |
| 2 | S. pneumoniae | 3:1 | 1445 | 238 | 2:1 |
| | L. monocytogenes | | 458 | 119 | |

DPCR chips were loaded with polymicrobial samples containing different proportions (ratios) of *S. pneumoniae* DNA to *L. monocytogenes* DNA to mimic challenging detection scenarios where one organism dominates a test sample. The targeted mixture ratios were created based on absorbance measurements of individual bacterial DNA concentrations using an Eppendorf Biospectrometer and then analyzed by U-dHRM and OVO SVM classification.

DISCUSSION

The integrative U-dHRM platform described herein advances HRM profiling by enabling the absolute quantification and identification of multiple genotypes in heterogeneous samples and at clinically relevant concentrations. By achieving HRM curve generation in 0.005% of the traditional HRM volume, and by massive parallelization of HRM across 20,000 reactions simultaneously, we achieve over a 200-fold increase in the dynamic range of detection compared to current HRM formats. Reduction in the size of reactions allows smaller volumes of reagents to be used while maintaining optimal reagent concentrations. Partitioning heterogeneous mixtures across 20,000 picoliter-scale reactions is also expected to overcome environmental microbial DNA contamination that may occur in real-world samples by spatially diluting, i.e. contaminating DNA and target DNA are partitioned from each other for discrimination and quantification[23]. An increased number of reactions also permits rapid generation of a large training curve database for each organism. Incorporating reference temperature calibrator sequences into each reaction helps normalizes against reaction condition variations for improved reliability. Automated melt curve identification is accomplished by removing non-specific melt curves by Tm thresholding and subsequently matching the remaining melt curves to a training database using our OVO SVM machine learning algorithm[24,26]. Together, these approaches comprise our microfluidic U-dHRM system and enable the quantitative characterization of complex samples containing multiple bacterial organisms.

Intercalating dye-based dPCR is typically used to detect a single, specific amplification product from one bacteria. Probe-based dPCR can be used to specifically identify up to four bacteria by multiplexing fluorescent probes, or a universal probe can be designed to detect the presence of bacteria non-specifically. By incorporating HRM and universal amplification into dPCR, our platform enables probe-free differentiation of multiple bacteria in a single sample. In our previous work, we showed that 37 clinically relevant organisms could be distinguished by general intercalating dye-based melt curves[24]. We anticipate that our U-dHRM platform will achieve at least this level of multiplexing and potentially more, since we were able to accomplish a signal to noise ratio and temperature resolution on-chip that matched standard qPCR HRM machines.

While a direct comparison of our U-dHRM detection method to a universal probe-based dPCR detection method was not feasible, due to different polymerase and reaction chemistry requirements, a comparison to typical intercalating dye-based dPCR techniques suggested that our platform and automated analysis approach may offer specificity and sensitivity improvements. Standard intercalating dye-based dPCR relies on thresholding total fluorescence intensity of digital reactions to determine whether they are positive or negative for amplification. Inhibitors that reduce amplification efficiency or non-specific background amplification could result in fluorescence intensities that are misclassified, giving rise to false positives and false negatives. However, melt curve analysis may offer a more reliable way to resolve these two conditions. For our reaction chemistry, we found that the typical dPCR approach of applying an intensity threshold to remove false positives left a significant number of reactions misclassified. Bacteria-specific melt curves were observed in several reactions classified as negative by this technique, and non-specific melt curves were observed in several reactions classified as positive. Our platform enabled Tm thresholding, which improved accuracy by 99% and 94%, respectively, in the Type I and II error rates based On manual observation of melt curves. Our approach could help to ensure that true single molecule sensitivity is attained for optimal lower limit of detection. One reason dPCR total fluorescence thresholding performed poorly in our study could be that we thermocycled significantly longer than most dPCR protocols recommend. A typical dPCR cycle number is kept to ~35, but we find that 70 cycles ensures full endpoint amplification from single molecules[23]. While this extended cycling improves accuracy of single-molecule target detection, it also allows off-target amplification to fluoresce more prominently in negative reactions.

Indeed, U-dHRM experiments showed evidence of two kinds of non-template amplification: non-template bacterial DNA amplification (contamination) and off-target amplification. Bacterial contamination produced distinct melt curves within the Tm range of 84-90° C. (FIG. 6 (c)). Given their high Tm, these melt curves are only likely to arise from amplification of the bacterial 16S gene long amplicon (~1 kbp). Sources of bacterial PCR contamination, which broad-based 16S amplification is highly sensitive to, include molecular biology grade water, PCR reagents, the environment, and DNA extraction kits[36]. Many studies have identified DNA polymerase preparations as the primary source of PCR contamination. The contamination of commercially available polymerase preparations is estimated at 10-1000 genomes/U enzyme[37]. Thus for our system, we would expect between 2.9 and 290 contaminating bacterial genomes per reaction, which is consistent with our observations (FIG. 6 (c)).

Figure 8:
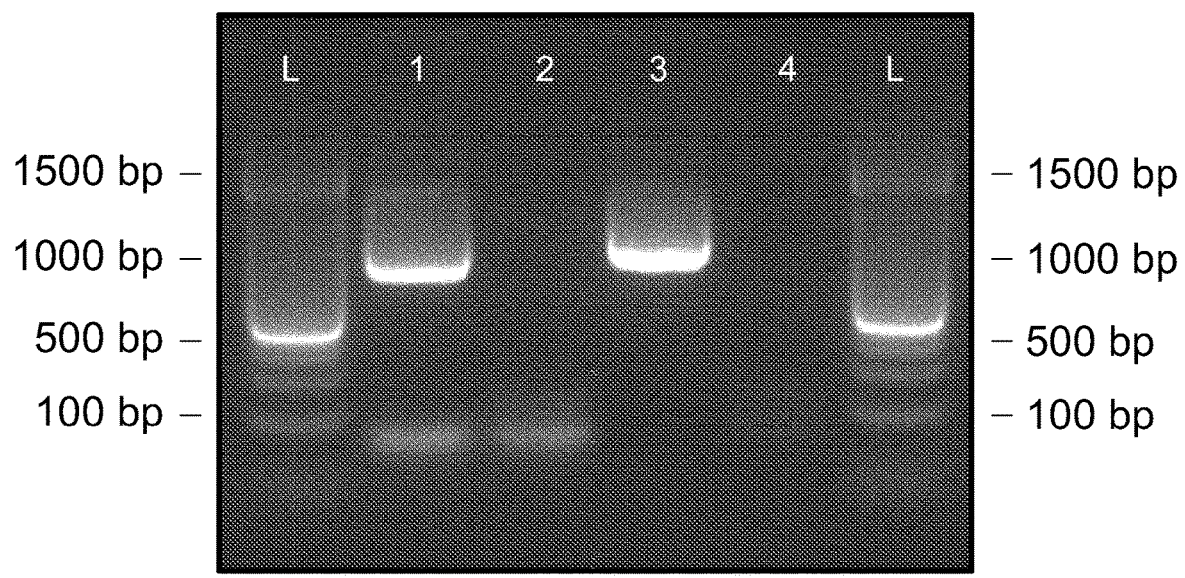

Off-target amplicons were observed to melt at lower temperatures (Suppl. FIG. 1C and FIG. 4D, Tm of ~81° C.). In U-dHRM, these products only arose in wells that were negative for bacterial DNA (FIG. 6. (b) and (c)). In qPCR, this off-target product was present in low-template and water control reactions and out-competed bacterial DNA in these conditions (FIG. 4D and FIG. 8). Based on Sanger sequencing analysis, this amplification product was non-specific (data not shown) and ~150 bp long by gel electrophoresis analysis (FIG. 8). Low reaction efficiency associated with long amplicon PCR and increased cycling time likely contributed to this non-specific amplification. An amplicon size <200 bp is ideal for qPCR. However, our goal is to discriminate numerous bacteria by their 16S sequences, where hypervariability occurs over ~1 kbp. Thus, for specific bacterial identification, we require a 1000 bp amplicon, which can reduce qPCR efficiency significantly[38,39]. In highly efficient qPCR reactions, unintended amplification products usually amplify at a lower efficiency than that of the target, and so are out-competed. However, long amplicon targets suffer from low amplification efficiency[38], allowing off-target amplification to more readily overtake target amplification when the amount of template is relatively low. This reduces the sensitivity of qPCR assays for low-level targets. Our standard curves show that we experience low amplification efficiency comparable to that reported by others in the literature (e.g. 60%, FIG. 7 (a))[39]. This explains the poor sensitivity of qPCR to low target concentrations (Suppl. FIG. 2A).

Importantly, it also highlights a strength of U-dHRM. Because digital reaction partitioning (1) reduces the effect of inhibitors, (2) reduces the effective concentration of contaminating DNA molecules that give rise to off-target amplification, and (3) allows for extended cycling to overcome low efficiency of amplification, since quantification is an endpoint measurement, it is not surprising that we achieve greater sensitivity in the dHRM format (FIG. 4C) than in a qPCR format (FIG. 7 (a)). Critically, our integration of HRM with dPCR allows for detection of target, contaminant, and off-target amplification products, and our OVO SVM approach for melt curve signature identification and quantification enables broad-based, automated identification of bacterial organisms.

However, some foreseeable limitations exist. Improvements to the temperature ramp reliability will be critical to ensure a larger database of melt curves are reliably resolved by U-dHRM. Here, calibrator sequences were used to align curves for initial Tm thresholding, but subsequently aligned to their derivative fluorescence value of 0.1 for shape comparison. This second alignment had the effect of ignoring Tm differences in bacteria-specific amplicons, and was required due to fluctuations in the temperature ramp from run-to-run. Insulation from environmental temperatures, an improved chip design with lower thermal mass, and incorporation of a PID controller are expected to overcome this issue. These improvements could also to lead to reduced background noise in the melt curve signal. This would improve our ability to resolve small changes in melt curve shapes generated on the U-dHRM platform, which are occasionally removed by our curve processing algorithms due to background noise.

The capabilities of our microfluidic U-dHRM system could impact infectious disease detection applications like neonatal bacteremia, where speed, breadth of detection, and sensitivity are critical factors. Clinical microbiology relies on lengthy culture-based assays to diagnose bacteremia, which has a high mortality rate that increases with every hour a patient goes undiagnosed and imprecisely treated. Polymicrobial bacteremia is associated with an even higher mortality rate than monomicrobial infection, highlighting the need to detect multiple organisms sensitively, and simultaneously. Immediate conservative treatment with broad-spectrum intravenous antibiotic therapy is typically initiated without any diagnostic information, leading to inaccurate and overtreatment as well as misuse of multiple antibiotics giving rise to the emergence of drug resistant pathogens. The ability to identify bacterial organisms in a blood sample within hours could change clinical practice by providing diagnostic information in time to alter treatment decisions. Retrospective studies also suggest that absolute quantification of bacterial genomic load in patients may be useful to assess severity of infection and to predict prognosis[4]. The detection of microbial DNA in clinical samples is typically challenged by the excess of human DNA compared to pathogen DNA, which can contribute to PCR reaction inhibition[4,40-42]. DPCR has been shown to decrease the impact of inhibitory substances[43]. Likewise, we find that U-dHRM detection of microbial DNA in mock blood samples is not inhibited by high human DNA background or inhibitors carried over in the DNA extraction from blood. This suggests that our device could have exciting implications in the clinical setting. Future work will focus on optimizing and validating our U-dHRM technology on patient-derived clinical samples.

Finally, computational approaches for anomaly detection are being explored by our group to identify bacterial melt curves that are not represented in our database. Currently, a 16S amplicon that melts above the Tm threshold will be automatically classified by our OVO SVM as the organism to which the melt curve is most closely matched. For undefined samples, where significantly more organisms may arise and unexpected emerging pathogens could be present, it will be crucial to identify whether a melt curve is a poor match to the database curves. Indeed, other groups have discovered new species of bacteria by observing alterations in bulk HRM curves by eye 29. Automation of this ability would represent a significant advancement for HRM profiling technology and is under development by our group.

Materials and Methods

High-Content U-dHRM Chip

In order to achieve high-content digital partitioning, the sample is loaded into a commercially available QuantStudio 3D Digital PCR 20K Chip v2 (Applied Biosystems, Foster City, CA). The chip contains 20,000 picoliter-scale wells manufactured from silicon with a hydrophilic treatment that allows high efficiency sample loading. A PCR-grade oil is deposited onto the loaded chip to prevent sample evaporation during cycling. The chip is sealed with an adhesive lid containing an optical window, which allows for imaging and the generation of melt curves. We chose to use a commercially manufactured chip for performance reliability. We coupled the dPCR chip to our custom designed master mix. The master mix is optimized to consistently amplify full length ~1,000 bp templates of the 16S gene, hypervariable regions V1-V6, and produce high fluorescence signal intensity for melt curve analysis while maintaining optimal surface tension for easy loading. An MJ Research PTC-200 Thermal Cycler (MJ Research Waltham, MA) is used for endpoint amplification. The thermal cycler is tilted at a 30-degree angle to collect the bubbles generated at high temperatures in the PCR-oil. These bubbles are trapped in an air pocket located outside of the chip's sample region, preventing sample evaporation from the small volume reactions.

Bacterial DNA Isolation and PCR

Wizard Genomic DNA Purification Kit (Promega Corporation, Madison, WI) was used to isolate DNA from an overnight culture of bacteria, and diluted in PCR water to the desired concentration. Absorbance measurements were made on stock DNA at concentrations within the working range of the spectrophotometer. Then, the DNA was serially diluted, and the expected concentration of the dilution used for dHRM was reported in the Tables and Figures for direct comparison of the different measuring modalities. The optimum PCR master mix for chip amplification, contained in a 14.5 µL reaction, was found to be 1×Phusion HF Buffer containing 1.5 mM MgCl2 (Thermo Fisher Scientific, Waltham, MA), 0.15 uM forward primer 5'-GYGGCG-NACGGGTGAGTAA-3' (SEO ID NO: 4) (Integrated DNA Technologies, Coralville, IA), 0.15 uM reverse primer 5'-AGCTGACGACANCCATGCA-3' (SEO ID NO: 5) (Integrated DNA Technologies, Coralville, IA), 0.2 mM dNTPs (Invitrogen, Carlsbad, CA), 2.5× EvaGreen (Biotium, Freemont, CA), 2×ROX (Thermo Fisher Scientific, Waltham, MA), 0.02 U/µL of Phusion HotStart Polymerase (Thermo Fisher Scientific, Waltham, MA), 1 µL of sample, and ultra pure PCR water (Quality Biological Inc., Gaithersburg, MD) to bring the total volume to 14.5 µL. The dPCR chip was cycled on a flatbed thermocycler with the following cycle: an initial enzyme activation (98° C., 30 s), followed by 70 cycles (95° C., 30 s, 59° C., 30 s, 72° C., 60 s). Temperature calibrator sequences with varying GC content used for system optimization are as follows: 0% GC
   (TTAAATTATAAAATATTTATAATATTAAT-
      TATATATATATAAATATAATA-C3 (SEQ ID NO: 1)),
   12% GC
   (TTAATTATAAAGGTATTTATAATATTGAATTATA-
      CATATCTAATATAATC-C3), (SEQ ID NO: 3) and
   76% GC (GCGCGGCCGGCACCCGAGACTCT-
GAGCGGCTGCTGGAGGTGCGGAAGCG
GAGGGGCGGG-C3 (SEQ ID NO: 2))[23].

Chip Heating Device

The U-dHRM device consists of a thermoelectric heating/cooling device (TE Technology, Unc. Traverse City, MI) controlled via an Arduino-based interface that uses pulse width modulation (PWM) to generate a temperature ramp (FIGS. 1, B and C). The thermoelectric device is in direct contact with a copper plate onto which the dPCR chips coated with a thin layer of thermal paste are clamped. This allows for even heat distribution and optimal surface contact. On the reverse side of the thermoelectric chip, an aluminum heat sink is attached to enable fast excessive heat dissipation. A type K thermocouple (OMEGA Engineering, Stamford, CT) is used to measure the temperature for each image taken during the temperature ramping. The thermocouple is fixed inside a surrogate chip, which is attached alongside the sample chip to the copper plate. The temperature readings are acquired by the microscope imaging software (Nikon MS-Elements) and are embedded in the image file metadata for offline analysis. The complete chip-heating setup is placed in a custom designed 3D printed stage adapter to securely mount the device on the microscope for imaging.

Fluorescent Imaging

Fluorescent imaging is accomplished using a Nikon Eclipse Ti platform customized for our dHRM system. A Nikon Plan/Fluor 4× objective with a numerical aperture of 0.13 and a working distance of 16.5× minimizes the number of images and time required to scan the entire chip. A Lumencor SPECTRA X LED Light Engine capable of producing 3-4 W of visible light from 380 nm to 680 nm is used as a light source. Images of the loading control dye, ROX, and melt curve intercalating dye, EvaGreen, are captured with 488/561 nm and 405/488 nm excitation/emission filters using an exposure time of 100 milliseconds. Images are captured every five seconds using a Hamamatsu digital camera, C11440 ORCA-Flash4.0. NIS-Elements software is programmed to automatically image the chip as the heating device ramps using the following workflow: define the capture settings for the ROX and EvaGreen channels, set the stage area to the chip's sample area, generate points within that stage area to image, and run time lapse to image each location for every time point. A Prior Scientific NanoScanZ (Rockland, MA) motorized stage is used to scan and image the entire chip automatically via the software. For every image, the microscope automatically records the temperature registered by our temperature probe within the metadata of the image. This allows for continuous scanning of the chip and recording of the fluorescence intensity in each well while concurrently heating the chip to generate 20,000 melt curves.

Image Analysis & SVM

Fluorescence and Tm thresholding for negative reaction removal Two approaches to thresholding reaction fluorescence for the identification and removal of negative reactions were compared. The typical dPCR approach of thresholding total reaction fluorescence was accomplished by first plotting a histogram in MATLAB of the total fluorescence intensities at room temperature of all chip reactions. The probability density function (PDF) for a mixture of two normal distributions was then applied to identify negative and positive reaction distributions. A threshold was identified at the lowest point of intensity where the two distributions intersected (FIG. 4B, top). This was performed for each sample type (i.e. DNA extracted from pure bacterial culture versus mock blood sample) to identify the appropriate threshold given unique background distributions.

A second approach was developed to identify a Tm threshold that separated off-target amplified reactions from true positives more accurately. First, raw melt curves were converted to derivative melt curves. On fully loaded chips where all reactions were positive (2 training chips) all reactions contained 16S amplicons, which were observed to melt with an average Tm of 89° C. On digitized chips (3 chips, testing data), off-target amplicons were observed to melt at much lower temperatures, average Tm of 81° C., while positive 16S amplicons melted reproducibly in the same range as the training chips. For thresholding analysis, the maximum peak height (Tm) above −d(Fluorescence)/dT=0.01 was found for each derivative melt curve between the range of 75° C. and 93° C. Then a histogram of the Tms was plotted in MATLAB, and the PDF for a mixture of two normal distributions was applied (FIG. 4B, bottom). Finally, the Tm threshold was chosen at the minima between the two distributions. Reactions melting below this Tm threshold were identified as negatives, while those melting above the threshold were identified as positives. The Tm threshold for samples of DNA extracted from pure bacterial cultures was identified and held constant at 84° C.

Melt Curve Data Generation

In order to generate melt curves from the acquired fluorescent images of the dPCR chip, we implement an automated image processing algorithm in MATLAB. The algorithm generates a binary mask for each temperature point to identify the centroid corresponding to each digital reaction well in the field. Then records the pixel intensity of the 441 neighboring pixels from the images of both the EvaGreen channel and the ROX channel. Each well's average pixel intensity is plotted against the measured temperature to generate the raw melt curve. Each melt curve is normalized to the ROX channel to account for any differences due to unequal loading. The Tm threshold described above is then applied to remove negative reactions and all incorrectly identified centroids. A Gaussian filter is then used to smooth the curves and the derivative is taken with respect to temperature to obtain -dF/dT. Finally, the curves are aligned via a temperature independent melt curve alignment at 0.1-dF/dT. This allowed the differences in melt curve shape to be maximized for later identification using a previously developed OVO SVM algorithm[24]. Briefly, an OVO SVM creates a maximal margin separating hyperplane between two data classes (i.e. melt curve signatures) using the Least Squares Method (linear kernel). OVO SVMs were created for all binary combinations of organisms with the training data generated from melt curves of known origin. During classification, a scoring method is applied and the most frequently called classification is chosen as the final melt curve identity.

Clinical Blood Sample Purification and Analysis

DNA from a clinical blood sample, which was known to be negative for bacterial infection, was extracted and purified using a High Pure PCR Template Preparation Kit (Roche Diagnostics Corporation, Indianapolis, IN). The purified blood DNA was eluted in a 204 volume. DNA of *L. monocytogenes* was isolated using the protocol described above in the methods section. Approximately 2,000 genomes of *L. monocytogenes* were added to the purified blood extraction. The maximum amount of the blood and bacterial DNA mixture (8.63 µL) was added to the PCR master mix. The final mass ratio of human DNA to bacterial DNA on chip was 12,172:1. The master mix was then loaded onto the chip and U-dHRM was performed following amplification cycles. The full chip was imaged as four tiles. Changes were made to the Tm thresholding script to account for the increased and oscillatory noise introduced by the blood DNA extract. First, the peak height for the derivative melt curve was raised to -dF/dT=0.015 to threshold noisier non-specific melt curves from true bacterial amplicons. Second, a lower threshold for melt curve troughs was added at −0.004-dF/dT, which aided in removing highly oscillatory and anomalous curves.

Cell Culture

Clinically isolated *S. pneumoniae* and *L. monocytogenes* were grown separately overnight in Luria-Bertani (LB) broth. Sterile conditions were used to ensure uncontaminated growth of each bacteria.

Example 2

Tunable Platform
System Design

Figure 10:
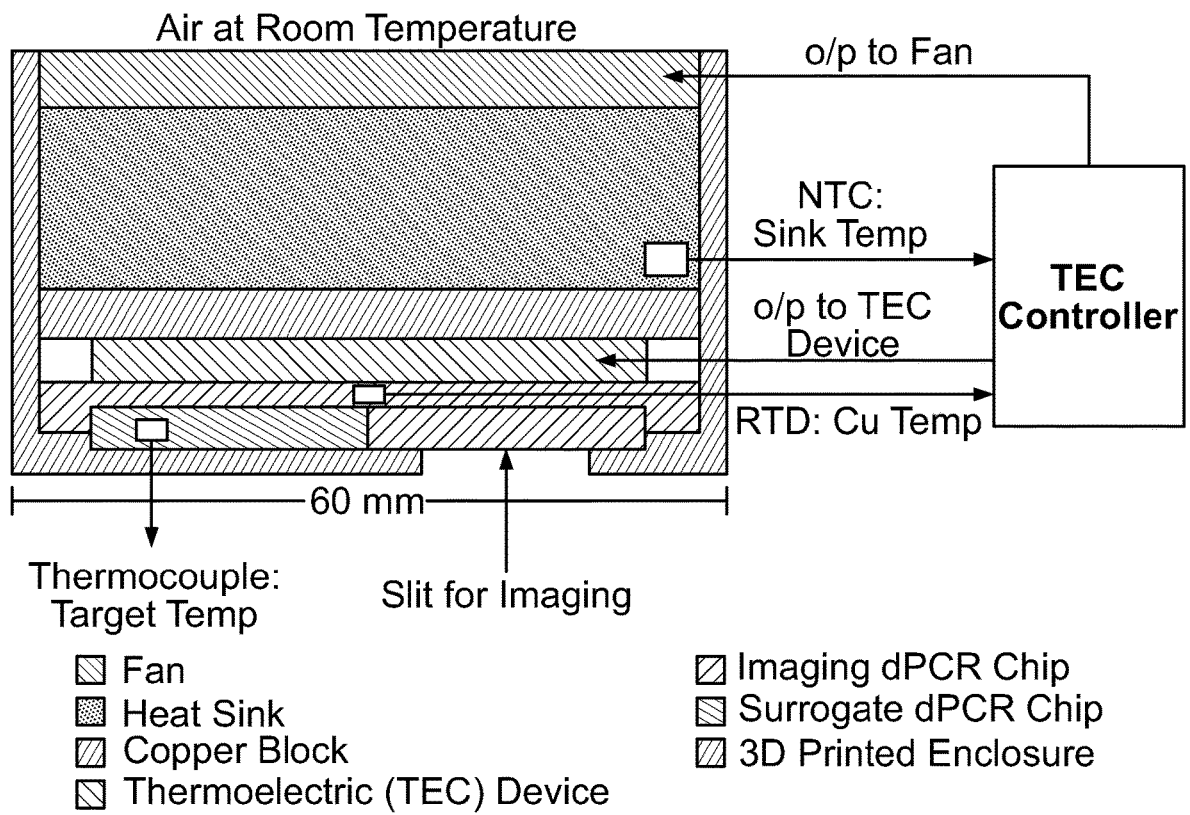
FIG. 10 is a cross sectional schematic of a U-dHRM platform.
Figure 11A:
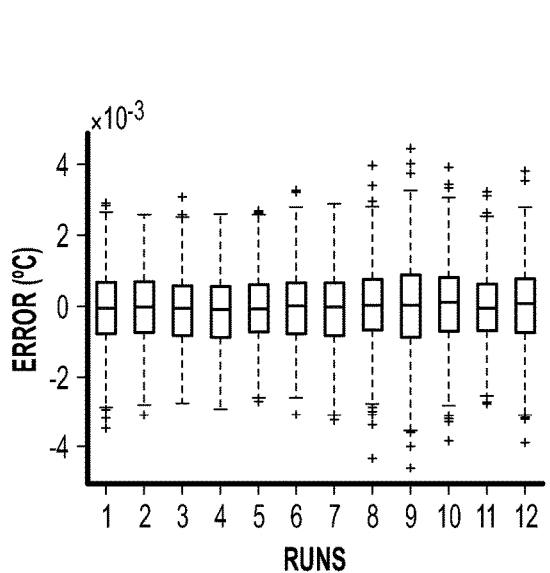
Figure 11B:
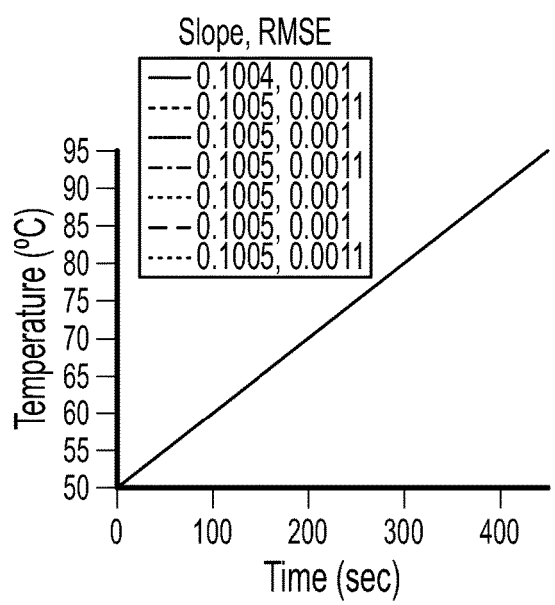

To optimize the heat ramp control of the microfluidic chip for identification of sequence-specific melt curve signatures, the thermal control system of the above described digital high resolution melt platform was redesigned. Previously, the chip was housed in a copper block, which was heated or cooled by a thermoelectric (TEC) device. To precisely control the TEC, a proportional-integral-derivative (PID) controller was added with temperature feedback from the copper block. The feedback was provided by a highly accurate resistance temperature detector (RTD) sensor that was embedded in the middle of the copper block. As described previously, a thin layer of thermal grease was added between the chip, copper block, and the TEC device to ensure efficient heat transfer. Heating dissipation from the reverse side of TEC was enhanced by attaching a fan to the aluminum heat sink. The speed of the fan was also controlled by the PID controller, commensurate with the sink temperature, using a negative temperature coefficient thermistor (NTC). The addition of the fan improved the ability to precisely heat to higher temperatures and allowed rapid cooling of the chip back to room temperature, decreasing the wait-time between two consecutive runs. The use of an off-the-shelf digital PCR chip did not allow placement of a temperature probe inside the chip in use. Therefore, to ensure that the thermal control achieved for the copper block efficiently transferred to the chip, a surrogate chip with a temperature sensing thermocouple embedded at its center was placed next to the test chip on the copper block. The entire chip-heating device assembly was held in place inside a custom designed 3D printed stage adaptor to securely mount the device on a microscope for imaging (FIG. 9, FIG. 10). While the copper block was independently controlled by standalone software, the proxy temperature measurement from the surrogate chip was synchronized with fluorescent imaging by the microscope control software (NIS-Elements). However, synchronizing imaging with temperature measurement required the use of an MS-Elements compatible temperature acquisition system (Tokai Hit Co., Japan) using a K-type thermocouple probe. This integrated imaging and temperature acquisition system limited the resolution of temperature measurement to 0.1° C. with a temperature sampling rate of ~0.2 Hz irrespective of the imaging rate. Therefore, the strategy was to precisely control the copper block temperature, establish a repeatable relationship between the copper block-embedded RTD and the surrogate chip-embedded thermocouple, and then use the integrated thermocouple temperature data and fluorescence imaging data to plot melting curves. Thermal Profile Characterization The PID controller provided temperature control of the copper block as per the desired ramp rate of 0.1° C./s. The maximum difference in the expected block temperature and observed temperature recorded using the RTD embedded within the block was measured as 0.004° C. (FIG. 11A). Across all runs, the expected ramp rate of 0.1° C./s was observed with maximum root mean squared error (RMSE) of 0.001° C. (FIG. 11B). This confirmed that precise temperature control of the copper block was achieved by our new heating system.

Figure 12A:
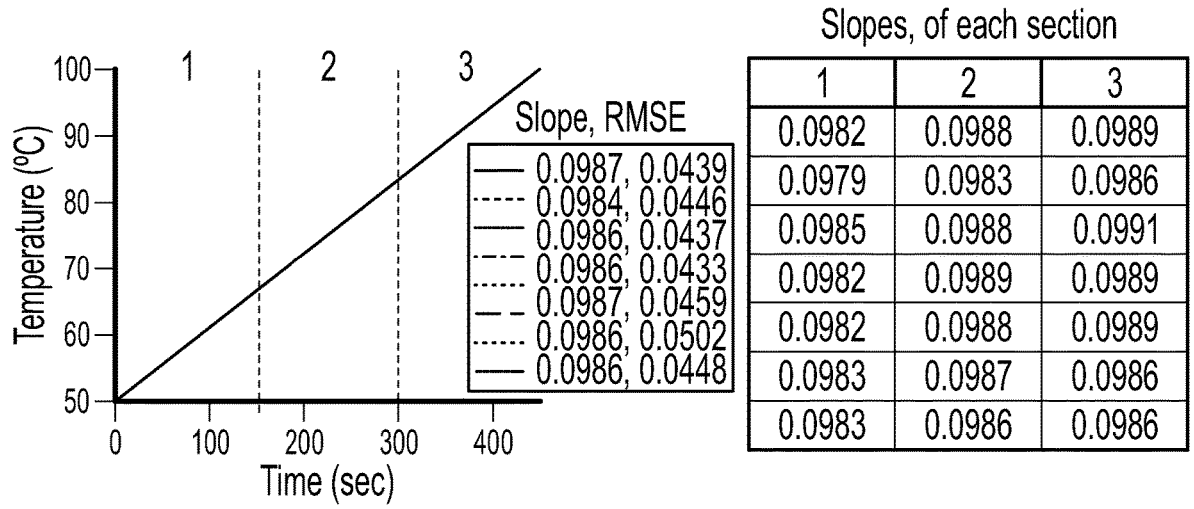
Figure 12B:
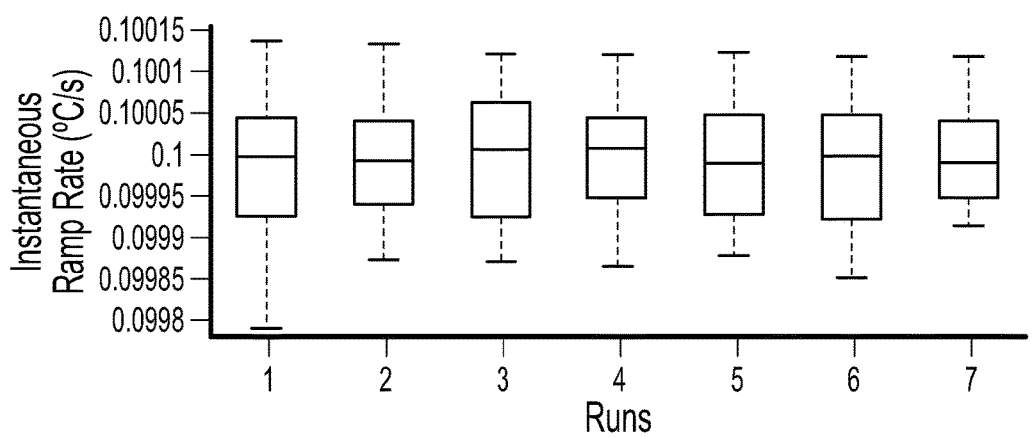

Next, the relationship between the block temperature and surrogate digital chip temperature was investigated. FIG. 12 shows temperature ramp measurements taken using the surrogate chip-embedded thermocouple for the same runs as depicted in FIG. 11A for the copper block-embedded RTD. Across all runs, the thermocouple measured a ramp rate of approximately 0.98° C./s on the chip, as compared to 0.1° C./s measured with the RTD in the block. The relationship between the thermocouple and RTD was highly repeatable across seven runs (FIG. 11B and FIG. 12A). To test the linearity of the slope, different temperature ranges of the thermocouple readings were analyzed and the slope was found to be consistent. This justified the use of a straight-line fit for the thermocouple data, revealing a maximum RMSE of 0.05° C. across runs (FIG. 12A). Instantaneous heating rates on the chip were also analyzed and showed no significant deviation ($R^2=1$) from linearity due to heat transfer losses from block to chip (FIG. 12B). Thus, the design achieved precise and linear heating control on the digital PCR chip within the accuracy and precision limits of the temperature acquisition system.

Melt Characterization with Temperature Calibrator Sequences

Figure 13A:
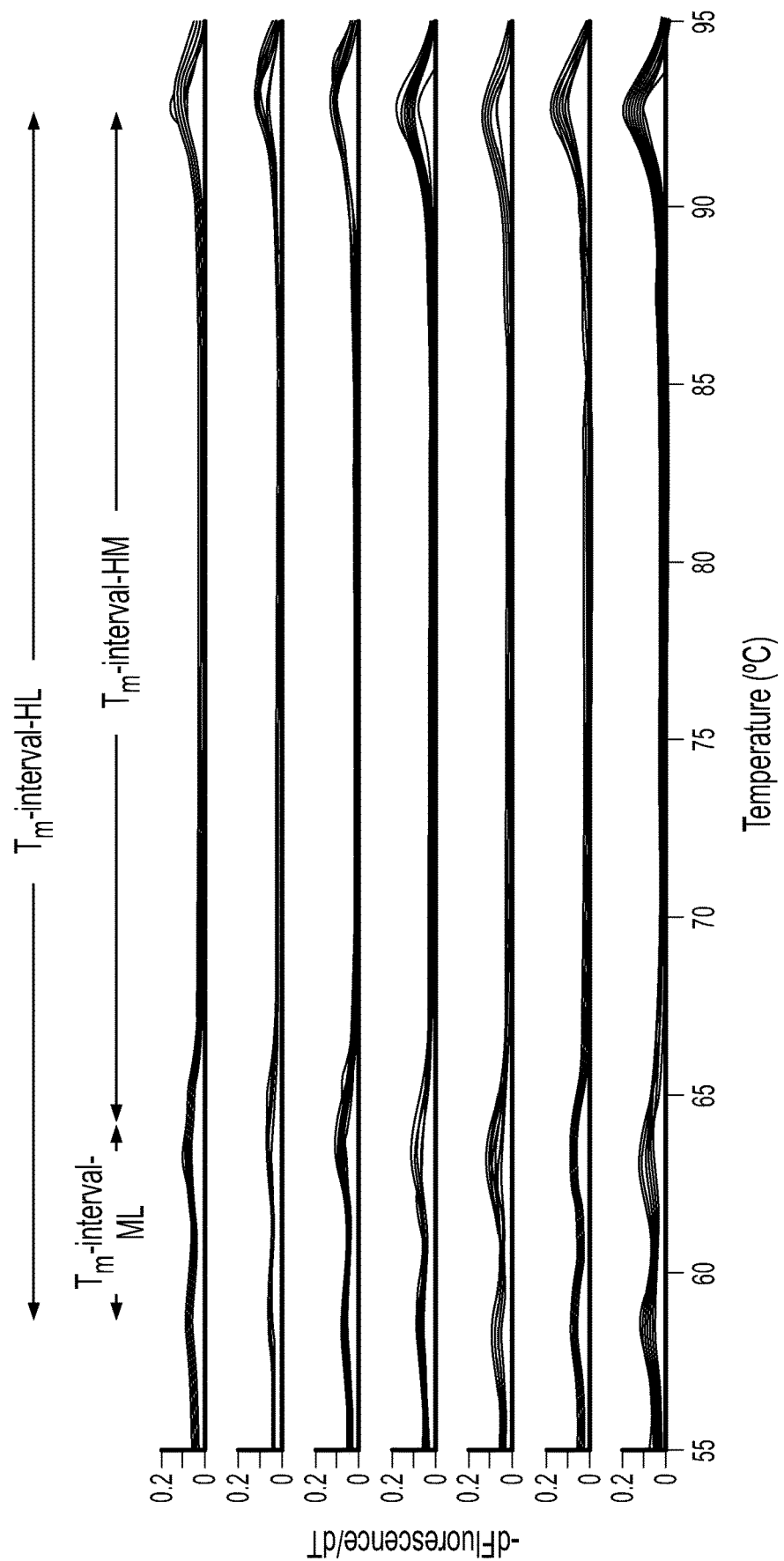

In theory, if heat ramping is linear and heat transfer is efficient, any inaccuracies in the absolute temperatures measured during the melting process could be reliably removed using temperature calibrator sequences. Such control DNA oligos of known $T_m$ can be included in all reactions and designed so that they melt outside of the amplicon's melting temperature range[47]. As long as the heat ramping rate is linear and of a constant slope, the distance between the calibrator $T_m$ and the amplicon $T_m$ is reliably maintained. Therefore, temperature offset errors occurring from run-to-run or well-to-well because of imperfections in temperature control or uniformity can be removed by simply shifting each melt curve to align the calibrator $T_m$ peaks to their correct melting temperature. Therefore, to further characterize the reliability of melting behavior on the chip, we used three synthetic oligo sequences with predicted $T_m$ ranging from ~57-93° C. to generate melt curve data for run-to-run and well-to-well variability analysis. These temperature calibrator sequences varied in GC content and length to achieve a high(~92.9° C.), mid(~62.8° C.) and low(~57.3° C.) melting temperatures. For this analysis, melt curves were generated on-chip at a heating rate of 0.1° C./s across seven replicate runs over several days. FIG. 13A shows plots of derivative melt curves across the seven runs.

Run-to-Run Variation.

First, we applied a peak detection algorithm to the derivative melt curves (FIG. 13A) to find the $T_m$ melting peaks in a +/−3° C. region around the predicted $T_m$ for each calibrator sequences (uMelt[30]: $T_m$-low 57.3° C., $T_m$-mid 62.8° C., and $T_m$-high 92.9° C.). Then, we calculated the difference between the $T_m$ of each calibrator to characterize run-to-run variations in linearity. Linearity differences among runs would be expected to produce stretching or compression of the melting curves along the temperature axis that would change the interval between $T_m$ peaks. However, if linearity is consistent, calibrator $T_m$ peaks can be shifted to match their predicted values to overcome offset errors. Thus, the high, mid, and low $T_m$-intervals were calculated as the difference between $T_m$-high and $T_m$-low ($T_m$-interval-HL), $T_m$-high and $T_m$-mid ($T_m$-interval-HM), and lastly $T_m$-mid and $T_m$-low ($T_m$-interval-ML). The mean of these $T_m$-intervals within runs is shown in FIG. 13B. To compare across runs, we calculated the standard deviation of these mean $T_m$-intervals. The $T_m$-intervals varied across runs with a standard deviation less than 0.1° C. for all the three intervals, showing run-to-run-repeatability within the accuracy and precision limits of the combined temperature acquisition system (see System Design) and imaging system. Next, to quantify the spread of the data across runs, we calculated the median absolute deviation (MAD) for the difference of the $T_m$-intervals of each well to the mean $T_m$-interval that is representative of the chip. FIG. 13C shows similar magnitudes of spread in well-to-well variation across runs. These run-to-run variability results are within the expected error limits of the system. However, the spread was slightly higher in magnitude for the $T_m$-interval-ML data. This is further analyzed as part of the well-to-well variation in the next section.

Well-to-Well Variation.

Once we established that the repeatability of $T_m$-intervals between runs were within expected error limits of the system, we sought to characterize the intra-run variability. This variability does not depend on the heat ramp, but rather the thermal gradient, loading differences, and evaporation anomalies across the chip. Interestingly, when we then investigated variability in $T_m$ peak values across the chip by plotting the difference of the $T_m$ peaks of each well to the corresponding mean $T_m$ for the chip, we found a lower intra-run variability in $T_m$-High as compared to $T_m$-Mid and $T_m$-Low (FIG. 14A). The largest median absolute deviation for $T_m$-High was 0.1° C., in comparison to the higher values of 0.13° C., and 0.14° C. observed for $T_m$-Mid and $T_m$-Low, respectively. Scatter plots for the difference in $T_m$-High and $T_m$-Mid from their representative mean-$T_m$ values for each chip revealed higher variability in the $T_m$-Mid (FIG. 14B). Further, $T_m$-Low behaved similar to $T_m$-Mid (FIG. 16). To investigate the location of wells with higher variability, we plotted the difference of $T_m$ of each well from the mean value (FIG. 14C). This showed higher variability in $T_m$-Low and $T_m$-Mid as compared to $T_m$-High throughout the chip reactions, with the majority of outliers (>+/−2.7 SD) located around the edges and corners of the digital chip. Analysis of the ROX reference dye intensity across the chip also revealed wells with significantly lower intensity located at the edges and corners (FIG. 17); however, this pattern was not highly correlated with the $T_m$ variability (FIG. 14C). These results suggest that the high calibrator sequence is inherently less susceptible to variability in melting than the low and the mid calibrator sequences, and further that there is a spatial dependence of variability coinciding with the well location on the chip.

Ramp Rate Dependence of Melt Curves

Having fully characterized the reliability of our melting device hardware and validated its performance biochemically, we next sought to investigate the dependence of the melt curve characteristics on ramp rate. Since our goal is to use melt curves to profile heterogeneous samples for multiple genotypes, we wanted to understand whether ramp rates could be optimized to enhance the effect of sequence differences on melt curve features. As a model genotyping task, we performed these experiments with bacterial DNA amplified from the 16S rRNA gene that included the hypervariable regions 1-6 (~1 kb in length). We chose *Acinetobacter*, *Moraxella*, and *Salmonella* genomic DNA as our templates because we have previously observed that their 16S sequences melt uniquely with either one or two transitions at ramp rate of 0.1° C./s in bulk qPCR reactions[23,24].

First, we generated 16S amplicons on 3 independent chips for each bacterium. These chips were then used to generate melt curves at ramp rates of 0.01° C./s, 0.05° C./s, 0.1° C./s and 0.2° C./s. We adjusted our imaging settings to maintain 0.1° C. resolution in fluorescence measurement by matching the imaging rate to heating rate (Table 3). To ensure that our thermal control was accurate for varying ramp rates, we observed the temperature profile in the proxy chip and in the copper block. These profiles were similar to what was seen for a ramp rate of 0.1° C./s, reported above. The slopes of the block temperature and fitted chip temperature were repeatable across all ramp rates, and there were negligible deviations in instantaneous rates throughout the runs (copper block and surrogate chip behavior for all ramp rates are shown in FIG. 18 and FIG. 19).

TABLE 3

Corresponding heating and imaging rates.

| Heat Ramp Rate (° C./s) | Imaging Frequency (Hz) |
|---|---|
| 0.01 | 0.1 |
| 0.05 | 0.5 |
| 0.1 | 1 |
| 0.2 | 2 |

Figure 15A:
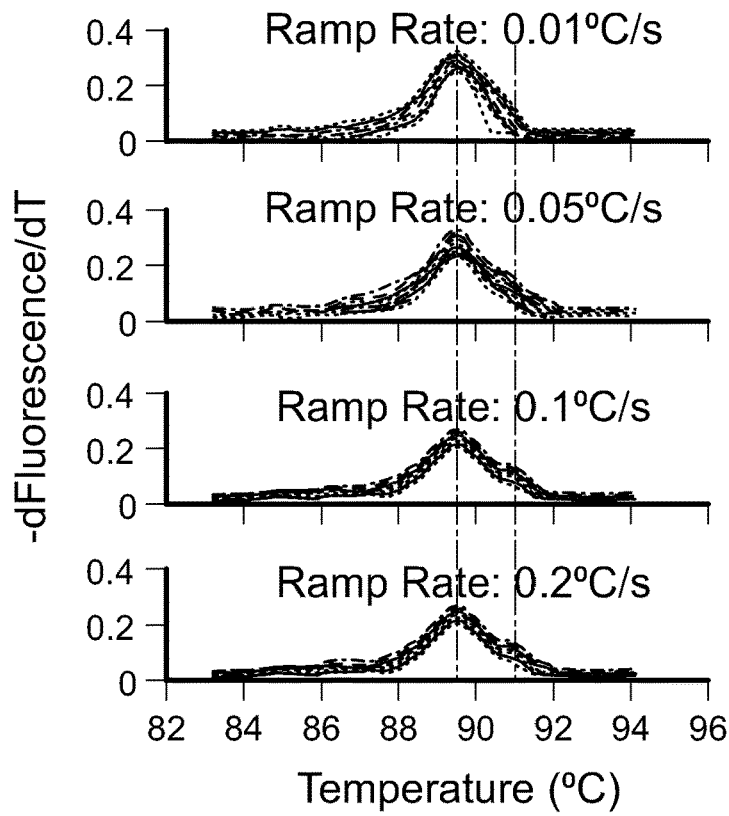
Figure 15B:
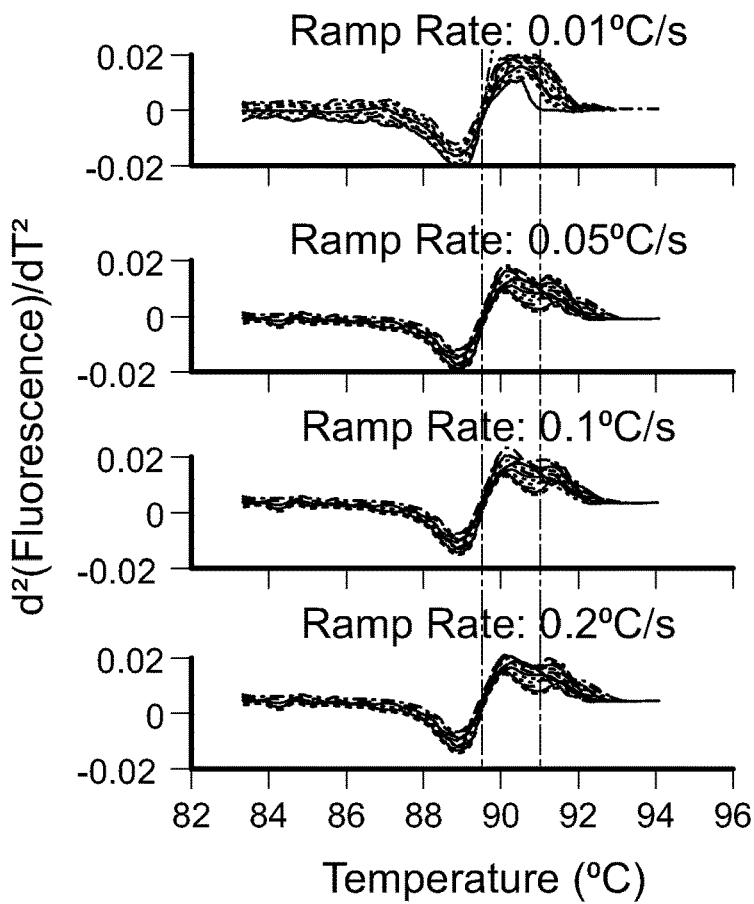
Figure 15C:
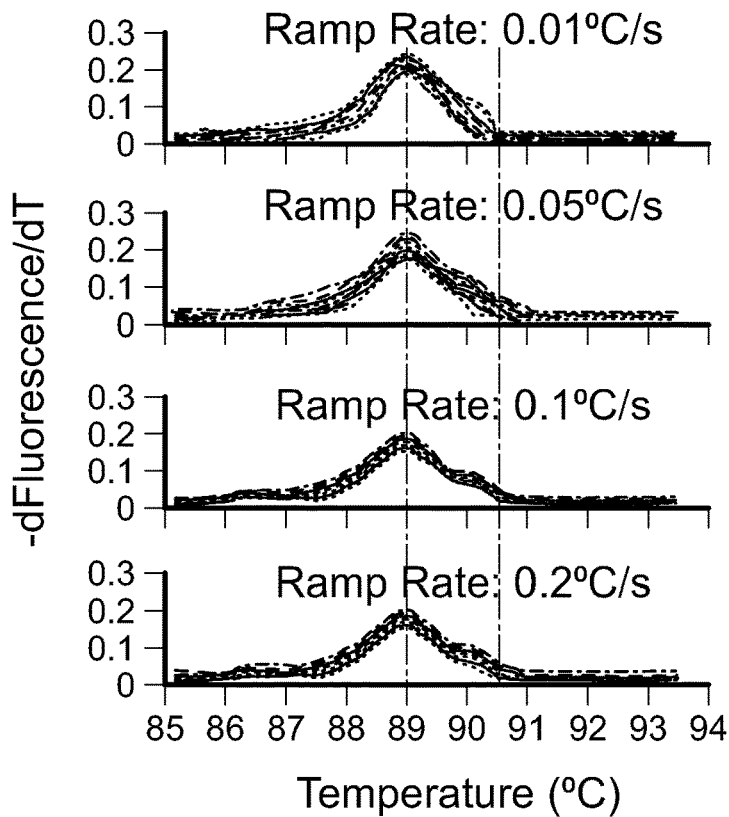
Figure 15D:
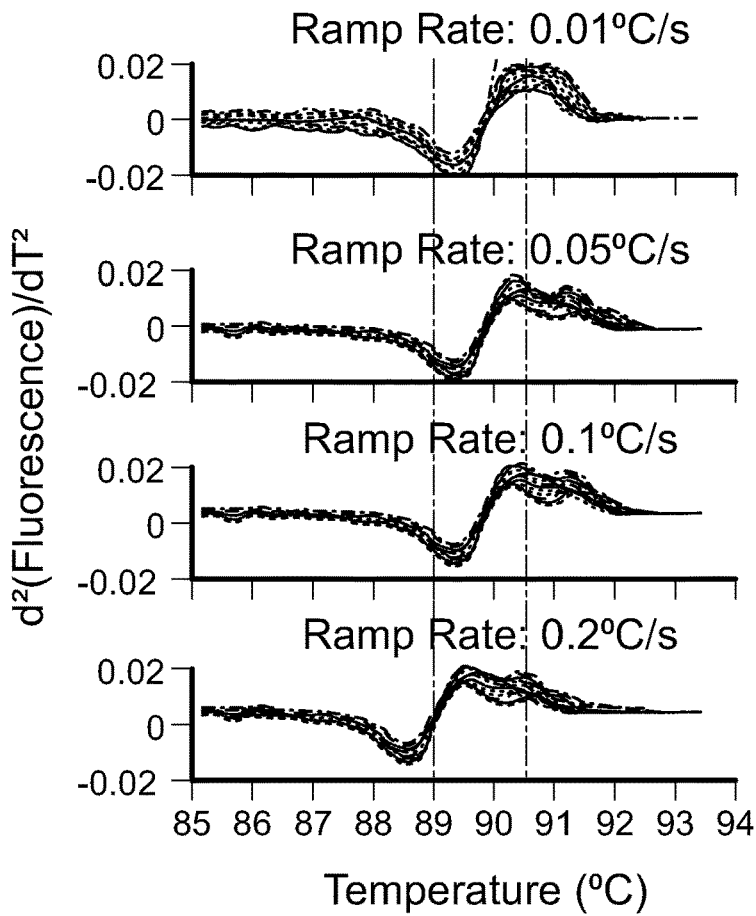
Figure 15E:
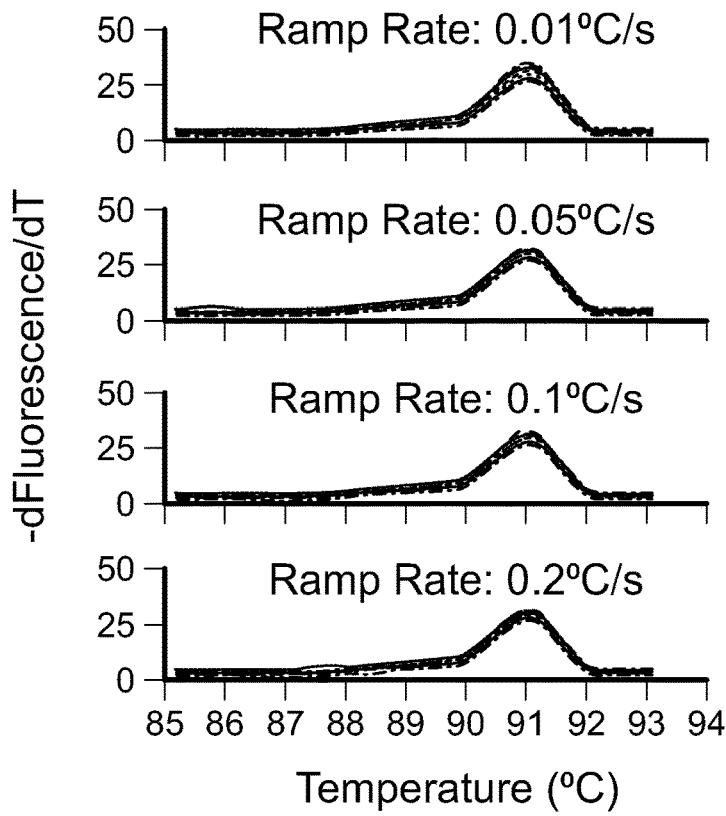
Figure 15F:
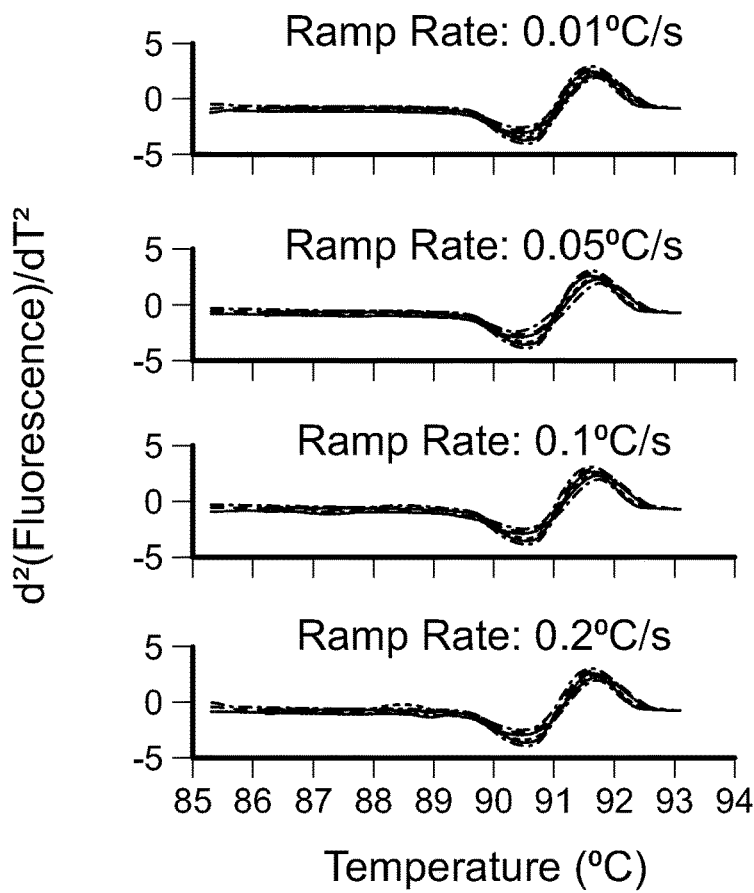

The 16S amplicons for *Acinetobacter baumanii* revealed multiple melt domains for higher ramp rates of 0.1° C./s and 0.2° C./s. However, a single melting domain was observed for 0.01° C./sec as seen in FIG. 15A. The second derivatives of the melt curves further highlight the difference in curve shape at different rates (FIG. 15B). Similar rate dependent melting (RDM) behavior was seen with *Moraxella catarrhalis* (FIGS. 15C and D.) However, *Salmonella enterica* serovar Heidelberg amplicons showed no significant RDM (FIGS. 15E and F), and neither did *Salmonella enterica* serovars *Enteritidis* and *Typhimurium* for 2 chips (FIG. 20). Statistically significant differences in curve shape (skewness) were observed for *A. baumanii* (p<0.005) between the melt rates of 0.01° C./s and 0.2° C./s but not for *S. enterica* Heidelberg (p=0.6). Interestingly, our previously published machine learning algorithm for automated melt curve genotyping was able to differentiate between melt curves generated at 0.01° C./s and 0.2° C./s for *A. baumanii* with ~97% accuracy, but failed to do so for *S. enterica* Heidelberg (~60% accuracy). The sequence specificity of the RDM phenomenon could be an additional feature used for melt-based sequence identification.

DISCUSSION

We have successfully designed and characterized a high resolution digital melt platform. Our design achieves highly repeatable temperature profiles for a range of melt rates and commensurate imaging frequencies. The run-to-run errors we observed were similar to the expected theoretical error limits of our system, approximately 0.14° C. Precision in temperature control is an important factor in being able to resolve melt curves. However, imaging systems can contribute to melt errors as well. The resolution of our imaging system is one image per 0.1° C. Thus, the minimum total RMSE error due to imaging (+/−0.05) and heating (+/−0.05) for our system is expected to be +/−0.07° C. These error limits can be improved with the development of a custom optical system with integrated and tunable image and temperature acquisition capabilities. Such design improvements would allow us to integrate a chip temperature probe with better accuracy and resolution into the imaging system. This, in addition to increasing our sampling rate for fluorescent data acquisition, would enhance the device's ability to resolve smaller $T_m$ differences. Beyond hardware limitations, other potential sources of variation could arise due to interactions in AT-GC content and the length of amplicons[9,48], slight differences in salt environments[48,49] or DNA concentrations[47,50-51], concentration and stability of DNA saturating dye[52] and reference ROX dye[53], pipetting errors, differential evaporation across reactions, and data processing methods[54].

The reliability and performance of our heating and hardware system enabled us to identify and characterize other sources of melt variation. Understanding well-to-well variation across the chip is crucial for absolute load quantification and sequence profiling at single genome sensitivity. We observed that wells producing outlier $T_m$ peaks are typically present at the corners and along the edges of the chip, as shown in FIG. 14B. These outliers could represent reactions where evaporation has altered the chemistry of the reaction, specifically the concentration of ions, which can shift $T_m$[48,49]. Analysis of the ROX reference dye intensity across the chip revealed a somewhat similar pattern of outliers with significantly lower intensity located at the edges and corners. It is known that thermal cycling and heating causes the ROX dye to become insoluble in water and precipitate out of solution, which leads to a slight drop in fluorescence at high temperatures. But this cannot account for the spatial pattern we observed, which was present even before heating. During melting, we did note a drop in ROX fluorescence and variations from well-to-well. This could introduce errors during the processing of the image data, since we normalize EvaGreen dye intensity to ROX as a loading control and to account for localized errors due to air bubbles released at high temperatures. In the future, we may benefit from either using other more thermally stable referencing dye, or including mathematical methods for error correction.

As compared to conventional PCR, the smaller reaction volumes of digital PCR could be expected to lead to larger variations in $T_m$ due to evaporation. On the other hand, the small form factor of the digital chip is expected to maintain a more uniform thermal gradient across the chip, leading to smaller variations in $T_m$. A previously published study reported $T_m$ differences ranging from 0.35° C. to 1.24° C. across 32-96 well plate melt instruments with standard deviations of 0.018° C. to 0.274° C.[44]. In comparison, after excluding the outliers due to evaporation at the corners and edges of our chips, differences in the high temperature calibrator $T_m$ on our digital melt platform were observed to vary from 0.22° C. to 0.6° C. This represents a significant improvement in heating uniformity compared to the standard well-plate format. Even with evaporation outliers included, median absolute deviation ranging from 0.05° C. to 0.1° C. and standard deviation of 0.06° C. to 0.13° C. were observed across the chip, which is less than that of the well-plate format. Optimizing for loading errors and evaporation would be expected to further improve performance. For example, the application of oil onto the loaded reaction wells could be sensitive to timing and amount deposited, and automation would ensure that the corner wells are covered as quickly as the central wells to minimize evaporation.

Our observation that the $T_m$-Low and $T_m$-Mid for the temperature calibrator sequences were more variable than the $T_m$-High calibrator is somewhat expected. Unfortunately, our high-throughput platform revealed that the $T_m$ variations of these low and mid calibrators were large enough to prevent their utility for melt curve normalization across runs. It is important to note that their variability was not correlated within individual wells or regions, indicating that it is not a function of location on the chip or differences in reaction conditions from well-to-well. Kinetic binding rates of DNA are known to vary based on GC content, as association rates of GC-rich oligomers are higher than rates of AT-rich equivalents[55]. Here, the low and mid calibrators have lower GC content (0% and 12% respectively) and are also shorter in length compared to the high calibrator (76% GC). DNA dissociation rates are also known to increase exponentially with temperature[55,56]. Further, physical models of DNA melting behavior predict that AT duplexes go through several cycles of hydrogen bond breakage and reformation, often involving an overall shift by one or more bases along the helix, before fully and finally disassociating. In contrast, the corresponding GC duplexes usually come apart only once[57]. Taken together, this suggests that it may be possible to design more reliable low and mid temperature calibrators by using very short GC-rich sequences.

It is generally thought that heating rate changes only result in shifts in melt curve $T_m$, whereas the dynamic melting characteristics of a PCR product are thought to be primarily determined by GC content, sequence length, and nucleotide order[44,45]. However, our study revealed that some long amplicons are highly sensitive to melting ramp rate, which not only shifts their $T_m$, but also changes the number and size of distinct melting transitions present. Our ability to identify a heating rate dependence of melt curve shape is in large part due to the tunability, uniformity, and throughput of the digital melt platform. For the long amplicon sequences, we studied, slower heating rates resulted generally in a single melt transition, whereas faster rates generated multiple melting domains. Interestingly, though, this response to heating rate was highly sequence dependent. Some long amplicon sequences maintained the same melt curve shape for multiple heating rates, while others do not. Thus, the response of a long amplicon to heating rate changes provides additional sequence-specific information that could enhance the specificity of melt curve-based sequence profiling. That is, where one ramp rate cannot discriminate two sequences by their melt curve, a combination of multiple ramp rates may reveal distinct melt responses. The mechanism underlying these differences may involve kinetic sampling of transition states. For example, slower rates would be expected to enable amplicons to sample a wider range of transition states, where shifting, re-organized binding, or secondary structure formation could effectively average out the fluorescence decay across the bulk population of amplicons. Faster rates may induce more uniform transition behavior involving abrupt local DNA "bubbles" that melt separately at a different temperature than the remainder of the sequence. Indeed, faster rates of melting have previously been associated with higher $T_m$ accuracy in homozygous melt analysis[47]. Alternatively, since heteroduplex melting has been found to be more apparent at faster heating rates, the multiple melt domains we observe at faster ramp rates may be the result of distinct heteroduplex binding transition states induced in homoduplex molecules[47].

In conclusion, our novel digital melt analysis platform with well-controlled and well-characterized heating across 20,000 reactions advances the concept of digital melt curve-based sequence profiling and could also support fundamental studies of DNA dissociation kinetics.

Materials and Methods

Sample Preparation for Temperature Calibrator Sequences

Three temperature calibrator sequences with varying GC content and known melting temperatures were used to optimize the heating of our system: 0% GC (TTAAATTATAAAATATTTATAATATTAAT-TATATATATATAAATATAATA-C3 (SEQ ID NO: 1)), 12% GC (TTAATTATAAAGGTATTTATAATATTGAATTATA-CATATCTAATATAATC-C3), (SEQ ID NO: 3) and 76% GC (GCGCGGCCGGCACCCGAGACTCT-GAGCGGCTGCTGGAGGTGCGGAAGCG GAGGGGCGGG-C3 (SEQ ID NO: 2)) (Integrated DNA Technologies, Coralville, IA). The master mix containing the three temperature calibrators was created as follows: 1× Phusion HF Buffer containing 1.5 mM MgCl2 (Thermo Fisher Scientific, Waltham, MA), 4 µM of equal mixtures of the three temperature calibrator sequences, 1× ROX (Bio-Rad Laboratories, Hercules, CA), 2× EvaGreen (Biotium, Freemont, CA) and Ultra Pure PCR water (Quality Biological Inc., Gaithersburg, MD) to bring the total volume to 15 µL. A volume of 14.5 µL of the 15 µl, master mix was then loaded onto a commercially available dPCR chip containing 20,000 picoliter-sized reaction wells, the QuantStudio™ 3D Digital PCR 20K Chip V2 (Applied Biosystems, Foster City, CA), as described in Ortiz et al. The chips were filled with a PCR-grade oil, Quant-Studio™ 3D Digital PCR Immersion Fluid (Applied Biosystems, Foster City, CA), to prevent sample evaporation during thermocycling and sealed with an adhesive lid which contained an optical window for imaging (included in 3D Digital PCR 20K Chip V2 Kit, Applied Biosystems, Foster City, CA).

Sample Preparation for Bacterial Samples

Bacterial gDNA was isolated from an overnight culture of bacteria using the Wizard Genomic DNA Purification Kit (Promega Corporation, Madison, WI). The stock DNA concentration was determined by the biospectrometer absorbance readings. Next, the desired DNA concentration was achieved through serial dilutions and added to the master mix which contained the following concentrations: 1× Phusion HF Buffer containing 1.5 mM MgCl2 (Thermo Fisher Scientific, Waltham, MA), 0.15 µM forward primer 5'-GyGGCGNACGGGTGAGTAA-3' (SEO ID NO: 4) (Integrated DNA Technologies, Coralville, IA), 0.15 µM reverse primer 5'-AGCTGACGACANCCATGCA-3' (SEO ID NO: 5) (Integrated DNA Technologies, Coralville, IA), 0.2 mM dNTPs (Invitrogen, Carlsbad, CA), 2.5× EvaGreen (Biotium, Freemont, CA), 2×ROX (Thermo Fisher Scientific, Waltham, MA), 2×ROX (Bio-Rad Laboratories, Hercules, CA), 0.02 U/µL Phusion HotStart Polymerase (Thermo Fisher Scientific, Waltham, MA), 0.3 µM temperature calibrator sequence with 0% GC-content (see above) and Ultra Pure PCR water (Quality Biological Inc., Gaithersburg, MD) to bring the total volume to 15 µL. A reaction volume of 14.5 µL was spread onto the dPCR chip (see above). A flatbed thermocycler was used to amplify the hypervariable regions, V1 to V6, of the 16S rRNA gene using the following PCR cycle: 1 cycle of 98° C. for 60 s; 70 cycles of 95° C. for 15s, 58° C. for 30s, 72° C. for 60s.

Cell Culture

Clinically isolated *Moraxella*, *Acintobacter*, and *Salmonella Enterica* were grown separately overnight in Luria-Bertani (LB) broth. Sterile conditions were used to ensure uncontaminated growth of each bacteria.

Chip Heating Device

The thermoelectric heating/cooling (TEC) device was purchased from TE Technology, Inc. (Traverse City, MI). The Proportional-Integral-Derivative (PID) controller was purchased from Meerstetter Engineering GmbH (Rubigen, Switzerland). RTD (Class 1/3B) and thermocouple (K type) sensors were purchased from Heraeus (Hanau, Germany) and OMEGA Engineering (Stamford, CT), respectively. Medium to high amount to thermal paste gave the most repeatable results (data not shown).

Fluorescent Imaging

Nikon Eclipse Ti (Nikon, Tokyo, Japan) platform is customized to accomplish imaging for the dHRM system, as described in our earlier work. Fluorescent images are captured with a melt curve intercalating dye, EvaGreen, and a control dye, ROX, at 488/561 nm and 405/488 nm excitation/emission filters, respectively, with an exposure time of 100 ms at a LED intensity of 40%. The microscope is interfaced with Hamamatsu digital camera, C11440 ORCA-Flash4.0 for image acquisition at a rate commensurate with the heat ramp. The imaging rate is adjusted based on the heat ramping to maintain a resolution of 0.1° C. between images (Table 1). NIS-Elements software is programmed to automatically image the chip as the heating device ramps by running a time lapse to image for every specified time point. For every image, the microscope automatically records the temperature of the surrogate chip registered by the thermocouple temperature probe within the metadata of the image. For this experiment, we used Nikon Plan/Fluor 4× objective with a numerical aperture of 0.13 and a working distance of 16.5×, to image a corner of the chip. Hence, every section of the chip was imaged as a part of separate run with simultaneous heating of the entire chip. This allowed us to maximize the number of runs/data per chip to characterize our heating system. For an ideal use case, as described in our previous publication, we can sweep imagining location to image the entire chip for all runs.

Image Analysis

Melt curve data generation. First the acquired fluorescence images are aligned using a template matching plugin in ImageJ. Then, melt curves are then generated using an automated image processing algorithm implemented in MATLAB. The algorithm applies median filter to remove salt and pepper noise in the images. It then generates a binary mask for each well on the chip and tracks them on all images. Pixels within 80% of the detected well radius are recorded and averaged to generate the fluorescence value in both ROX and EvaGreen channels for the specified well. The fluorescence values are tracked for each well across all images to generate curves for both EvaGreen and ROX channels. Filter (EvaGreen) curves generated are normalized against filter (ROX) values to account for any localized errors/noise due to bubbles in the chip or any abrupt change in ambient light as described in our previous publication[24].

Temperature Measure

Imaging software records the temperature corresponding to each image from the surrogate chip. However, the temperature acquisition rate is limited to an approximate 0.20 Hz. Line fitting is performed using the unique temperature, time pair acquisitions to estimate temperature for each acquired image for faster imaging rates (FIG. 21). A melt curve for each well is plotted against this estimated temperature. The negative derivative is taken with respect to temperature. Normalization and smoothing is performed as described in previous publications. To studying rate dependence of melt curves, bacterial melt curves generated were aligned the curves to their $T_m$.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1 Song, L. et al. Direct detection of bacterial genomic DNA at sub-femtomolar concentrations using single molecule arrays. Anal Chem 85, 1932-1939, doi:10.1021/ac303426b (2013).
2 Patel, R. MALDI-TOF MS for the diagnosis of infectious diseases. Clin Chem 61, 100-111, doi:10.1373/clinchem.2014.221770 (2015).
3 Frey, K. G. et al. Comparison of three next-generation sequencing platforms for metagenomic sequencing and identification of pathogens in blood. BMC genomics 15, 96, doi:10.1186/1471-2164-15-96 (2014).
4 Lisboa, T., Waterer, G. & Rello, J. We should be measuring genomic bacterial load and virulence factors. Critical care medicine 38, S656-662, doi:10.1097/CCM.0b013e3181f2453a (2010).
5 Pasic, M. D., Samaan, S. & Yousef, G. M. Genomic medicine: new frontiers and new challenges. Clin Chem 59, 158-167, doi:10.1373/clinchem.2012.184622 (2013).
6 Pritchard, C. C., Cheng, H. H. & Tewari, M. MicroRNA profiling: approaches and considerations. Nat Rev Genet 13, 358-369, doi:10.1038/nrg3198 (2012).
7 Blainey, P. C. The future is now: single-cell genomics of bacteria and archaea. FEMS microbiology reviews 37, 407-427, doi:10.1111/1574-6976.12015 (2013).
8 Erali, M., Palais, R. & Wittwer, C. SNP genotyping by unlabeled probe melting analysis. Methods in molecular biology (Clifton, NJ) 429, 199-206, doi:10.1007/978-1-60327-040-3_14 (2008).
9 Reed, G. H. & Wittwer, C. T. Sensitivity and Specificity of Single-Nucleotide Polymorphism Scanning by High-Resolution Melting Analysis. Clinical Chemistry 50, 1748-1754, doi:10.1373/clinchem.2003.029751 (2004).
10 Dwight, Z., Palais, R. & Wittwer, C. T. uMELT: prediction of high-resolution melting curves and dynamic melting profiles of PCR products in a rich web application. doi:10.1093/bioinformatics/btr065 (2011).
11 Chakravorty, S. et al. Genotypic susceptibility testing of Mycobacterium tuberculosis isolates for amikacin and kanamycin resistance by use of a rapid sloppy molecular beacon-based assay identifies more cases of low-level drug resistance than phenotypic Lowenstein-Jensen testing. J Clin Microbiol 53, 43-51, doi:10.1128/jcm.02059-14 (2015).
12 El-Hajj, H. H. et al. Use of sloppy molecular beacon probes for identification of mycobacterial species. J Clin Microbiol 47, 1190-1198, doi:10.1128/jcm.02043-08 (2009).
13 den Dunnen, J. T., Vossen, R. H. A. M., Aten, E. & Roos, A. High-Resolution Melting Analysis (HRMA)-More Than Just Sequence Variant Screening. Hum Mutat 30, 860-866 (2009).
14 Mohamed Suhaimi, N. A. et al. Non-invasive sensitive detection of KRAS and BRAF mutation in circulating tumor cells of colorectal cancer patients. Molecular oncology 9, 850-860, doi:10.1016/j.molonc.2014.12.011 (2015).
15 Athamanolap, P., Shin, D. J. & Wang, T. H. Droplet Array Platform for High-Resolution Melt Analysis of DNA Methylation Density. Journal of laboratory automation 19, 304-312, doi:10.1177/2211068213507923 (2013).
16 Castresana, J. S. et al. Detection of methylation in promoter sequences by melting curve analysis-based semiquantitative real time PCR. Bmc Cancer 8 (2008).
17 Gürtler, V., Grandob, D., Mayalla, B. C., Wanga, J. & Ghaly-Deriasa, S. A novel method for simultaneous Enterococcus species identification/typing and van genotyping by high resolution melt analysis. Journal of Microbiological Methods 90, 167-181 (2012).
18 Hjelmsø, M. H. et al. High Resolution Melt analysis for rapid comparison of bacterial community composition. Applied and Environmental Microbiology, doi:10.1128/aem.03923-13 (2014).
19 Hardick, J. et al. Identification of Bacterial Pathogens in Ascitic Fluids from Patients with Suspected Spontaneous Bacterial Peritonitis by Use of Broad-Range PCR (16S PCR) Coupled with High-Resolution Melt Analysis. Journal of Clinical Microbiology 50, 2428-2432, doi:10.1128/JCM.00345-12 (2012).
20 Jeng, K. et al. Application of a 16S rRNA PCR—High-Resolution Melt Analysis Assay for Rapid Detection of Salmonella bacteremia. Journal of Clinical Microbiology 50, 1122-1124, doi:10.1128/JCM.05121-11 (2012).
21 Masek, B. J. et al. Sensitive detection and serovar differentiation of typhoidal and nontyphoidal Salmonella enterica species using 16S rRNA Gene PCR coupled with high-resolution melt analysis. J Mol Diagn 16, 261-266, doi:10.1016/j.jmoldx.2013.10.011 (2014).
22 Yang, S. et al. Rapid identification of biothreat and other clinically relevant bacterial species by use of universal PCR coupled with high-resolution melting analysis. J Clin Microbiol 47, 2252-2255, doi:10.1128/jcm.00033-09 (2009).
23 Fraley, S. I. et al. Universal digital high-resolution melt: a novel approach to broad-based profiling of heterogeneous biological samples. Nucleic Acids Research 41, e175, doi:10.1093/nar/gkt684 (2013).
24 Fraley, S. I. et al. Nested Machine Learning Facilitates Increased Sequence Content for Large-Scale Automated High Resolution Melt Genotyping. Sci Rep 6, 19218, doi:10.1038/srep19218 (2016).
25 Fan, J. B., Chee, M. S. & Gunderson, K. L. Highly parallel genomic assays. Nat Rev Genet 7, 632-644, doi:10.1038/nrg1901 (2006).
26 Athamanolap, P. et al. Trainable high resolution melt curve machine learning classifier for large-scale reliable genotyping of sequence variants. PLoS One 9, e109094, doi:10.1371/journal.pone.0109094 (2014).
27 Candiloro, I. L., Mikeska, T., Hokland, P. & Dobrovic, A. Rapid analysis of heterogeneously methylated DNA using digital methylation-sensitive high resolution melting: application to the CDKN2B (p15) gene. Epigenetics & chromatin 1, 7, doi:10.1186/1756-8935-1-7 (2008).

28 Zou, H. et al. High detection rates of colorectal neoplasia by stool DNA testing with a novel digital melt curve assay. *Gastroenterology* 136, 459-470, doi:10.1053/j.gastro.2008.10.023 (2009).

29 Pritt, B. S. et al. Identification of a novel pathogenic *Borrelia* species causing Lyme borreliosis with unusually high spirochaetaemia: a descriptive study. *Lancet Infect Dis*, doi:10.1016/s1473-3099(15)00464-8 (2016).

30 Dietzman, D. E., Fischer, G. W. & Schoenknecht, F. D. Neonatal *Escherichia coli* septicemia-bacterial counts in blood. *The Journal of pediatrics* 85, 128-130 (1974).

31 Kellogg, J. A. et al. Frequency of low level bacteremia in infants from birth to two months of age. *Pediatr Infect Dis J*16, 381-385 (1997).

32 Chakravorty, S., Helb, D., Burday, M., Connell, N. & Alland, D. A detailed analysis of 16S ribosomal RNA gene segments for the diagnosis of pathogenic bacteria. *Journal of Microbiological Methods* 69, 330-339, doi:10.1016/j.mimet.2007.02.005 (2007).

33 Simonsen, K. A., Anderson-Berry, A. L., Delair, S. F. & Davies, H. D. Early-onset neonatal sepsis. *Clinical microbiology reviews* 27, 21-47, doi:10.1128/cmr.00031-13 (2014).

34 Mohammadi, T., Reesink, H. W., Vandenbroucke-Grauls, C. & Savelkoul, P. H. M. Optimization of Real-Time PCR Assay for Rapid and Sensitive Detection of Eubacterial 16S Ribosomal DNA in Platelet Concentrates. *J Clin Microbiol* 41, 4796-4798, doi:10.1128/jcm.41.10.4796-4798.2003 (2003).

35 Rothman, R. E. et al. Detection of bacteremia in emergency department patients at risk for infective endocarditis using universal 16S rRNA primers in a decontaminated polymerase chain reaction assay. *J Infect Dis* 186, 1677-1681, doi:10.1086/345367 (2002).

36 Salter, S. J. et al. Reagent and laboratory contamination can critically impact sequence-based microbiome analyses. *BMC Biol* 12, 87, doi:10.1186/s12915-014-0087-z (2014).

37 Spangler, R., Goddard, N. L. & Thaler, D. S. Optimizing Taq polymerase concentration for improved signal-to-noise in the broad range detection of low abundance bacteria. *PLoS One* 4, e7010, doi:10.1371/journal.pone.0007010 (2009).

38 Mallona, I., Weiss, J. & Marcos, E. C. pcrEfficiency: a Web tool for PCR amplification efficiency prediction. *BMC Bioinformatics* 12, 404, doi:10.1186/1471-2105-12-404 (2011).

39 Rothfuss, O., Gasser, T. & Patenge, N. Analysis of differential DNA damage in the mitochondrial genome employing a semi-long run real-time PCR approach. *Nucleic Acids Res* 38, e24, doi:10.1093/nar/gkp1082 (2010).

40 Dellinger, R. P. et al. Surviving Sepsis Campaign: international guidelines for management of severe sepsis and septic shock: 2008. *Critical care medicine* 36, 296-327, doi:10.1097/01.ccm.0000298158.12101.41 (2008).

41 McGowan, K. L., Foster, J. A. & Coffin, S. E. Outpatient pediatric blood cultures: time to positivity. *Pediatrics* 106, 251-255 (2000).

42 Opota, O., Croxatto, A., Prod'hom, G. & Greub, G. Blood culture-based diagnosis of bacteraemia: state of the art. *Clinical microbiology and infection: the official publication of the European Society of Clinical Microbiology and Infectious Diseases* 21, 313-322, doi:10.1016/j.cmi.2015.01.003 (2015).

43 Nixon, G. et al. Comparative study of sensitivity, linearity, and resistance to inhibition of digital and nondigital polymerase chain reaction and loop mediated isothermal amplification assays for quantification of human cytomegalovirus. *Anal Chem* 86, 4387-4394, doi:10.1021/ac500208w (2014).

44 Herrmann, M. G., Durtschi, J. D., Bromley, L. K., Wittwer, C. T. & Voelkerding, K. V. Amplicon DNA Melting Analysis for Mutation Scanning and Genotyping: Cross-Platform Comparison of Instruments and Dyes. *Clin. Chem.* 52, (2006).

45 Ririe, K. M., Rasmussen, R. P. & Wittwer, C. T. Product Differentiation by Analysis of DNA Melting Curves during the Polymerase Chain Reaction. *Anal. Biochem.* 245, 154-160 (1997).

46 James, M. M., Wang, L., Donnell, D., Cousins, M. M., Barlow-Mosha, L., Fogel, J. M., Towler, W. I., Agwu, A. L., Bagenda, D., Mubiru, M., Musoke, P. & Eshleman, S. H. Use of a high resolution melting assay to analyze HIV diversity in HIV-infected Ugandan children. *Pediatr. Infect. Dis. J.* 31, e222-8 (2012).

47 Gundry, C. N., Dobrowolski, S. F., Martin, Y. R., Robbins, T. C., Nay, L. M., Boyd, N., Coyne, T., Wall, M. D., Wittwer, C. T. & Teng, D. H. F. Base-pair neutral homozygotes can be discriminated by calibrated high-resolution melting of small amplicons. *Nucleic Acids Res.* 36, 3401-3408 (2008).

48 Panjkovich, A. & Melo, F. Comparison of different melting temperature calculation methods for short DNA sequences. *Bioinformatics* 21, 711-722 (2005).

49 Schildkraut, C. & Lifson, S. Dependence of the melting temperature of DNA on salt concentration. *Biopolymers* 3, 195-208 (1965).

50 von Ahsen, N., Wittwer, C. T. & Schutz, E. Oligonucleotide Melting Temperatures under PCR Conditions: Nearest-Neighbor Corrections for Mg2+, Deoxynucleotide Triphosphate, and Dimethyl Sulfoxide Concentrations with Comparison to Alternative Empirical Formulas. *Clin. Chem.* 47, (2001).

51 Wetmur, J. G. DNA Probes: Applications of the Principles of Nucleic Acid Hybridization. Crit. Rev. Biochem. Mol. Biol. 26, 227-259 (1991).

52 Mao, F., Leung, W. Y. & Xin, X. Characterization of EvaGreen and the implication of its physicochemical properties for qPCR applications. *BMC Biotechnol.* 7, 76 (2007).

53 Pfaffl, M. W., Vandesompele, J. & Kubista, M. Data analysis software. *Real-time PCR Curr. Technol. Appl.* Caister Acad. Press Norfolk, UK 65-83 (2009).

54 Li, M., Zhou, L., Palais, R. A. & Wittwer, C. T. Genotyping Accuracy of High-Resolution DNA Melting Instruments. *Clin. Chem.* 60, (2014).

55 Ouldridge, T. E., Sulc, P., Romano, F., Doye, J. P. K. & Louis, A. A. DNA hybridization kinetics: zippering, internal displacement and sequence dependence. *Nucleic Acids Res.* 41, 8886-95 (2013).

56 Morrison, L. E. & Stols, L. M. Sensitive fluorescence-based thermodynamic and kinetic measurements of DNA hybridization in solution. *Biochemistry* 32, 3095-104 (1993).

57 Drukker, K., Wu, G. & Schatz, G. C. Model simulations of DNA denaturation dynamics. *J. Chem. Phys.* 114, 579 (2001).

What is claimed is:

1. A method of profiling a sequence of a nucleic acid in a sample, the method comprising:
   combining a sample comprising a nucleic acid with
   one or more amplification primers,
   one or more DNA intercalating dyes,
   a reference dye, and
   reagents for amplifying a nucleic acid to form a reaction mixture, wherein the reagents for amplifying a nucleic acid comprise a polymerase;
   partitioning the reaction mixture into 10,000 or greater partitions, wherein each partition has a volume of 1 nL or less of the reaction mixture;
   amplifying the nucleic acid in each partition to produce an amplification product, wherein the amplification product comprises zero, one, or more amplicons;
   performing melt analysis of the amplification product in each partition, whereby a melt curve for the amplification product in each partition is produced; and
   profiling the sequence of the nucleic acid,
   wherein the step of profiling comprises: excluding one or more melt curves from a plurality of melt curves based on both: a comparison of a shape of one or more target amplification product melt curves to a plurality of melt curves from different nucleic acid sequences, and a comparison of a peak height of the one or more target amplification product melt curves to a peak height threshold, and
   wherein the excluded one or more melt curves correspond to an off-target amplification product melt curve, wherein the off-target amplification product consists of one or more of a host nucleic acid molecule, an environmental nucleic acid molecule, or a degraded nucleic acid molecule.

2. The method of claim 1, further comprising detecting reference dye and excluding noise values based on the detection of the reference dye.

3. The method of claim 1, wherein the reaction mixture further comprises a surfactant in an amount of from about 0.005% to about 0.85%.

4. The method of claim 1, wherein the one or more amplification primers are universal amplification primers.

5. The method of claim 1, wherein the reaction mixture comprises at least two unique amplification primers that are configured such that the amplification product in each partition is labeled with a fluorescent signal.

6. The method of claim 1, wherein the one or more amplification primers are configured such that one or more amplicons have a size greater than 500 base pairs.

7. The method of claim 1, wherein performing melt analysis of the amplification product in each partition comprises heating the partitions at a heating rate of 0.002° C./s to 1° C./s.

8. The method of claim 1, wherein the profiling the sequence of a target nucleic acid is automated by use of a computer model or algorithm that classifies the target nucleic acid based on the comparison to a reference melt curve or a computer model.

9. The method of claim 8, wherein the computer model or algorithm is a machine learning algorithm for automated melt curve classification.

10. The method of claim 9, wherein the machine learning algorithm uses a probabilistic classification model selected from a generative classifier and a discriminative classifier.

11. The method of claim 9, wherein the machine learning algorithm uses a probabilistic model to assign confidence scores on classification.

12. The method of claim 8, wherein the algorithm uses an entropy measure.

13. The method of claim 12, wherein the entropy measure is Shannon entropy.

14. The method of claim 1, further comprising assigning confidence scores to sequence profiles obtained from profiling the sequence of the nucleic acid.

15. The method of claim 1, wherein the melt analysis comprises adjusting an imaging rate and/or a heating rate to achieve a resolution.

16. The method of claim 15, wherein the imaging rate and/or the heating rate is adjusted to achieve a resolution from about one image per 0.005° C. to about one image per 0.1° C.

17. The method of claim 1, wherein the comparison of the peak height of the one or more target amplification product melt curves to the peak height threshold is performed prior to the comparison of the shape of the one or more target amplification product melt curves to the plurality of melt curves from different nucleic acid sequences.

18. The method of claim 17, wherein the step of profiling further comprises excluding the one or more melt curves from the plurality of melt curves based on a comparison of a melting temperature (Tm) for the amplification product in each partition to a plurality of melting temperatures from different nucleic acid sequences, and wherein the comparison of the Tm is performed after the comparison of the peak height of the one or more target amplification product melt curves to the peak height threshold.

19. A method of profiling a sequence of a nucleic acid in a sample, the method comprising:
   combining a sample comprising a nucleic acid with
   one or more amplification primers,
   one or more DNA intercalating dyes,
   a reference dye, and
   reagents for amplifying a nucleic acid to form a reaction mixture, wherein the reagents for amplifying a nucleic acid comprise a polymerase;
   partitioning the reaction mixture into 10,000 or greater partitions, wherein each partition has a volume of 1 nL or less of the reaction mixture;
   amplifying the nucleic acid in each partition to produce an amplification product, wherein the amplification product comprises zero, one, or more amplicons;
   performing melt analysis of the amplification product in each partition, whereby a melt curve for the amplification product in each partition is produced;
   profiling the sequence of the nucleic acid, wherein the step of profiling comprises: excluding one or more melt curves from a plurality of melt curves based on both: a comparison of a shape of one or more target amplification product melt curves to a plurality of melt curves from different nucleic acid sequences, and a comparison of a peak height of the one or more target amplification product melt curves to a peak height threshold,
   wherein the excluded one or more melt curves correspond to an off-target amplification product melt curve, wherein the off-target amplification product consists of one or more of a host nucleic acid molecule, an environmental nucleic acid molecule, or a degraded nucleic acid molecule; and
   performing a second melt analysis of the amplification product in each partition, whereby a second melt curve for the amplification product in each partition is produced.

20. A method of profiling a sequence of a nucleic acid in a sample, the method comprising:
- combining a sample comprising a nucleic acid with
  - one or more amplification primers,
  - one or more DNA intercalating dyes,
  - a reference dye, and
  - reagents for amplifying a nucleic acid to form a reaction mixture, wherein the reagents for amplifying a nucleic acid comprise a polymerase;
- partitioning the reaction mixture into 10,000 or greater partitions, wherein each partition has a volume of 1 nL or less of the reaction mixture;
- amplifying the nucleic acid in each partition to produce an amplification product, wherein the amplification product comprises zero, one, or more amplicons;
- performing melt analysis of the amplification product in each partition by subjecting the sample to a first heating rate to obtain a first melt curve signature for the amplification product in each partition;
- subjecting the sample to a second heating rate to obtain a second melt curve signature for the amplification product in each partition; and
- performing a heating rate-dependent melt curve analysis using a computer model or algorithm that excludes one or more melt curve signatures from a plurality of melt curve signatures based on both: a comparison of a shape of one or more target amplification product melt curve signatures to a plurality of melt curve signatures from different nucleic acid sequences, and a comparison of a peak height of the one or more target amplification product melt curve signatures to a peak height threshold,
- wherein the excluded one or more melt curve signatures correspond to an off-target amplification product melt curve signature, wherein the off-target amplification product consists of one or more of a host nucleic acid molecule, an environmental nucleic acid molecule, or a degraded nucleic acid molecule; and
- wherein the computer model or algorithm classifies a nucleic acid based on the comparison of one or both of the first and second melt curve signatures to a reference melt curve signature.

* * * * *